United States Patent
Schreiber et al.

(10) Patent No.: US 10,189,908 B2
(45) Date of Patent: Jan. 29, 2019

(54) CHIMERIC ANTIGEN RECEPTORS RECOGNIZING CANCER-SPECIFIC TN GLYCOPEPTIDE VARIANTS

(71) Applicant: THE UNIVERSITY OF CHICAGO, Chicago, IL (US)

(72) Inventors: Hans Schreiber, Chicago, IL (US); Christian Idel, Chicago, IL (US); Boris Engels, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 62 days.

(21) Appl. No.: 15/115,536

(22) PCT Filed: Feb. 5, 2015

(86) PCT No.: PCT/US2015/014673
§ 371 (c)(1),
(2) Date: Jul. 29, 2016

(87) PCT Pub. No.: WO2015/120187
PCT Pub. Date: Aug. 13, 2015

(65) Prior Publication Data
US 2017/0166652 A1 Jun. 15, 2017

Related U.S. Application Data

(60) Provisional application No. 61/936,304, filed on Feb. 5, 2014.

(51) Int. Cl.
*C07K 16/30* (2006.01)
*A61K 39/00* (2006.01)

(52) U.S. Cl.
CPC .... *C07K 16/3092* (2013.01); *A61K 2039/505* (2013.01); *C07K 2317/56* (2013.01); *C07K 2317/622* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,450,150 A | 5/1984 | Sidman | |
| 4,946,778 A | 8/1990 | Ladner et al. | |
| 5,225,539 A | 7/1993 | Winter | |
| 5,403,484 A | 4/1995 | Ladner et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,585,089 A | 12/1996 | Queen et al. | |
| 5,639,641 A | 6/1997 | Pedersen et al. | |
| 5,693,761 A | 12/1997 | Queen et al. | |
| 5,693,762 A | 12/1997 | Queen et al. | |
| 5,702,892 A | 12/1997 | Mulligan-Kehoe | |
| 5,714,352 A | 2/1998 | Jakobovits | |
| 5,780,279 A | 7/1998 | Matthews et al. | |
| 5,821,047 A | 10/1998 | Garrard et al. | |
| 5,824,520 A | 10/1998 | Mulligan-Kehoe | |
| 5,837,500 A | 11/1998 | Ladner et al. | |
| 5,855,885 A | 1/1999 | Smith et al. | |
| 5,858,657 A | 1/1999 | Winter et al. | |
| 5,871,907 A | 2/1999 | Winter et al. | |
| 5,969,108 A | 10/1999 | McCafferty et al. | |
| 6,057,098 A | 5/2000 | Buechler et al. | |
| 6,225,447 B1 | 5/2001 | Winter et al. | |
| 6,265,150 B1 | 7/2001 | Terstappen et al. | |
| 6,699,843 B2 | 3/2004 | Pietras et al. | |
| 8,440,798 B2 | 5/2013 | Clausen et al. | |
| 2002/0197266 A1 | 12/2002 | Debinski | |
| 2003/0077676 A1 | 4/2003 | Denardo et al. | |
| 2003/0077826 A1 | 4/2003 | Edelman et al. | |
| 2005/0282233 A1 | 12/2005 | Eriksson et al. | |
| 2006/0167230 A1 | 7/2006 | Koga et al. | |
| 2014/0271582 A1 | 9/2014 | Forman et al. | |
| 2014/0271635 A1 | 9/2014 | Brogdon et al. | |
| 2014/0274909 A1 | 9/2014 | Orentas et al. | |
| 2014/0286973 A1 | 9/2014 | Powell, Jr. | |
| 2014/0301993 A1 | 10/2014 | Powell, Jr. et al. | |
| 2014/0322183 A1 | 10/2014 | Milone et al. | |
| 2014/0322212 A1 | 10/2014 | Brogdon et al. | |
| 2014/0322275 A1 | 10/2014 | Brogdon et al. | |
| 2014/0369977 A1 | 12/2014 | Zhang et al. | |
| 2017/0166652 A1* | 6/2017 | Schreiber | C07K 16/3092 |

FOREIGN PATENT DOCUMENTS

| | | | |
|---|---|---|---|
| DE | 3218121 A1 | 11/1983 | |
| EP | 0 058 481 A1 | 8/1982 | |
| EP | 0 133 988 A2 | 3/1985 | |
| EP | 0 239 400 A2 | 9/1987 | |
| EP | 2814846 A1 | 12/2014 | |
| GB | 2188638 A | 10/1987 | |

(Continued)

OTHER PUBLICATIONS

Adjei et al., Pulmonary delivery of peptide drugs: effect of particle size on bioavailability of leuprolide acetate in healthy male volunteers, *Pharm. Res.*, 7(6):565-9 (1990).

(Continued)

*Primary Examiner* — Michael D Burkhart
(74) *Attorney, Agent, or Firm* — Marshall, Gerstein & Borun LLP

(57) ABSTRACT

Disclosed are binding proteins, or fragments thereof, that specifically binds to a cancer-specific glycosylation variant of a protein and to a second epitope on the same protein, to a different protein presented on the same cell, or to a different protein presented on a different cell, such as an encoded polypeptide binding to both a cancer cell and an activated T cell. Also disclosed are polynucleotides encoding such binding proteins, including polynucleotides comprising codon-optimized coding regions and polynucleotides comprising coding regions that are not codon-optimized for expression in a particular host cell. Also disclosed are methods of making the encoded polypeptide and methods of using the polypeptide to treat, prevent or ameliorate the symptom of a disease such as cancer.

18 Claims, 16 Drawing Sheets
Specification includes a Sequence Listing.

(56) References Cited

FOREIGN PATENT DOCUMENTS

| WO | WO-99/040942 A1 | 8/1999 |
|---|---|---|
| WO | WO-2000/032218 A1 | 6/2000 |
| WO | WO-2004/033036 A2 | 4/2004 |
| WO | WO-2005/087812 A1 | 9/2005 |
| WO | WO-2007/133747 A2 | 11/2007 |
| WO | WO-2007/141411 A1 | 12/2007 |
| WO | WO-2008/130158 A1 | 10/2008 |
| WO | WO-2014/011988 A2 | 1/2014 |
| WO | WO-2014/153270 A1 | 9/2014 |
| WO | WO-2014/179759 A1 | 11/2014 |
| WO | WO-2014/180306 A1 | 11/2014 |
| WO | WO-2014/184143 A1 | 11/2014 |
| WO | WO-2014/186469 A2 | 11/2014 |
| WO | WO-2014/190273 A1 | 11/2014 |
| WO | WO-2014/208760 A1 | 12/2014 |

OTHER PUBLICATIONS

Akita et al., Developmental expression of a unique carbohydrate antigen, Tn antigen, in mouse central nervous tissues, *J. Neurosci. Res.*, 65:595-603 (2001).
Amann Metal., Therapeutic window of MuS110, a single-chain antibody construct bispecific for murine EpCAM and murine CD3, *Cancer Res.*, 68:143-51 (2008).
Ando et al., Mouse-human chimeric anti-Tn IgG1 induced antitumor activity against Jurkat cells in vitro and in vivo, *Biol. Pharm. Bull.*, 31:1739-44 (2008).
Apostolopoulos et al., A glycopeptide in complex with MHC class I uses the GalNAc residue as an anchor, *Proc. Natl. Acad. Sci. USA*, 100:15029-34 (2003).
ASHP Handbook on Injectable Drugs, Toissel, 4th ed., pp. 622-630 (1986).
Baeuerle et al., BiTE: Teaching antibodies to engage T-cells for cancer therapy, *Curr. Opin. Mol. Ther.*, 11:22-30 (2009).
Barderas et al., High expression of IL-13 receptor α2 in colorectal cancer is associated with invasion, liver metastasis, and poor prognosis, *Can. Res.*, 72:2780-90 (2012).
Blixt et al., A high-throughput 0-glycopeptide discovery platform for seromic profiling, *J. Proteome Res.*, 9:5250-61 (2010).
Blixt et al., Analysis of Tn antigenicity with a panel of new IgM and IgG1 monoclonal antibodies raised against leukemic cells, *Glycobiology*, 22:529-42 (2012).
Blixt et al., Autoantibodies to aberrantly glycosylated MUC1 in early stage breast cancer are associated with a better prognosis, *Breast Can. Res.*, 13:R25 (2011).
Bos et al., CD4+ T-cell help in the tumor milieu is required for recruitment and cytolytic function of CD8+ T lymphocytes, *Cancer Res.*, 70:8368-77 (2010).
Brentjens et al., Eradication of systemic B-cell tumors by genetically targeted human T lymphocytes co-stimulated by CD80 and interleukin-15, *Nat. Med.*, 9:279-86 (2003).
Brien et al., Protection by immunoglobulin dual-affinity retargeting antibodies against dengue virus, *J. Virol.*, 87: 7747-53 (2013).
Brischwein et al., MT110: a novel bispecific single-chain antibody construct with high efficacy in eradicating established tumors, *Mol. Immunol.*, 43:1129-43 (2006).
Brooks et al., Antibody recognition of a unique tumor-specific glycopeptide antigen., *Proc. Natl. Acad. Sci. USA*, 107:10056-61 (2010).
Carpenito et al., Control of large, established tumor xenografts with genetically retargeted human T cells containing CD28 and CD137 domains, *Proc. Natl. Acad. Sci. USA*, 106:3360-5 (2009).
Cioffi et al., EpCAM/CD3-Bispecific T-cell engaging antibody MT110 eliminates primary human pancreatic cancer stem cells, *Clin. Can. Res.*, 18:465-74 (2012).
Cloosen et al., Expression of tumor-associated differentiation antigens, MUC1 glycoforms and CEA, in human thymic epithelial cells: implications for self-tolerance and tumor therapy, *Cancer Res.*, 67:3919-26 (2007).

Cole et al., The EBV—Hybridoma Technique and its Application to Human Lung Cancer, *Monoclonal Antibodies and Cancer Therapy*, 77-96 (1985).
Cote et al., Generation of human monoclonal antibodies reactive with cellular antigens, *Proc. Natl. Acad. Sci. USA*, 80:2026-30 (1983).
Coulie et al., A mutated intron sequence codes for an antigenic peptide recognized by cytolytic T lymphocytes on a human melanoma, *Proc. Natl. Acad. Sci. USA*, 92:7976-80 (1995).
Dausset et al., Acquired hemolytic anemia with polyagglutinability of red blood cells due to a new factor present in normal human serum (Anti-Tn), *Blood*, 14:1079-93 (1959).
Davila et al., How do CARs work?: Early insights from recent clinical studies targeting CD19, *Oncoimmunology*, 1:1577-83 (2012).
Deluca et al., Parental Drug Delivery Systems Pharmaceutics and Pharmacy Practice, J. B. Lippincott Company, Philadelphia, PA, Banker and Chalmers, eds., pp. 238-250 (1982).
Donner et al., Randomization by cluster. Sample size requirements and analysis, *Am. J. Epidemiol.*, 114:906-14 (1981).
Dubey et al., The immunodominant antigen of an ultraviolet-induced regressor tumor is generated by a somatic point mutation in the DEAD box helicase p68, *J. Exp. Med.*, 185:695-705 (1997).
Epstein-Brash et al., Prolonged duration local anesthesia with minimal toxicity, *Proc. Natl. Acad. Sci. USA.*, 106(17):7125-30 (2009).
Fong, Minutes of the Recombinant DNA Advisory Committee, Jun. 19, 2012. In Recombinant DNA Advisory Committee. U.S. Department of Health and Human Services, National Institutes of Health, Bethesda, MD. 1-34 (2012).
Fournier et al., Bispecific antibodies and trispecific immunocytokines for targeting the immune system against cancer: preparing for the future, *BioDrugs*, 27:35-53 (2013).
Fu et al., Loss of intestinal core 1-derived 0-glycans causes spontaneous colitis in mice, *J. Clin. Invest.*, 121:1657-66 (2011).
Fuller-Pace, DExD/H box RNA helicases: multifunctional proteins with important roles in transcriptional regulation, *Nucleic Acids Res.*, 34:4206-15 (2006).
GenBank Accession No. DQ381544.1, Mus musculus mAb3F2 immunoglobulin gamma heavy chain mRNA, partial cds, dated Feb. 1, 2007.
GenBank Accession No. DQ381549.1, Mus musculus mAb5C2 immunoglobulin kappa light chain mRNA, partial cds, dated Feb. 1, 2007.
Gold et al., Aptamers As Therapeutic and Diagnostic Agents, *Rev. Molec. Biotechnol.*, 74:5-13 (2000).
Guba et al.,. A primary tumor promotes dormancy of solitary tumor cells before inhibiting angiogenesis, *Cancer Res.*, 61:5575-9 (2001).
Gupta et al., Stochastic state transitions give rise to phenotypic equilibrium in populations of cancer cells, *Cell*, 146:633-44 (2011).
Harlow et al.(eds.), Antibodies: A Laboratory Manual, CSH Press (1988).
Haskard et al., The production of human monoclonal autoantibodies from patients with rheumatoid arthritis by the EBV-hybridoma technique, *J. Immunol. Methods*, 74(2):361-7 (1984).
Hirohashi et a., Blood group A cross-reacting epitope defined by monoclonal antibodies NCC-LU-35 and -81 expressed in cancer of blood group 0 or B individuals: its identification as Tn antigen, *Proc. Natl. Acad. Sci. USA*, 82:7039-43 (1985).
Huse et al., Generation of a large combinatorial library of the immunoglobulin repertoire in phage lambda, *Science*, 246, 1275-81 (1989).
International Preliminary Report on Patentability, PCT/US2015/014673, dated Aug. 9, 2015.
International Search Report and Written Opinion, PCT/US2015/014673, dated May 21, 2015.
Janeway et al., Immunobiology, 5th Edition, Garland Publishing, New York, (1996).
Johnson et al., Effector cell recruitment with novel Fv-based dual-affinity re-targeting protein leads to potent tumor cytolysis and in vivo B-cell depletion, *J. Mol. Biol.*, 399:436-49 (2010).
Jones et al., Replacing the complementarity-determining regions in a human antibody with those from a mouse, *Nature*, 321:522-5 (1986).

(56) References Cited

OTHER PUBLICATIONS

Ju et al., A unique molecular chaperone Cosmc required for activity of the mammalian core 1 beta 3-galactosyltransferase, *Proc. Natl. Acad. Sci. USA*, 99:16613-8 (2002).
Ju et al., Human tumor antigens Tn and sialyl Tn arise from mutations in Cosmc, *Cancer Res.*, 68:1636-46 (2008).
Ju et al., Protein glycosylation: chaperone mutation in Tn syndrome, *Nature*, 437:1252 (2005).
Ju et al., The Tn antigen-structural simplicity and biological complexity, *Angew. Chem. Int. Ed. Engl.*, 50:1770-91 (2011).
Kabat et al., Sequences of proteins of immunological interest, U.S. Department of Health and Human Services, (1983).
Kalos et al., T cells with chimeric antigen receptors have potent antitumor effects and can establish memory in patients with advanced leukemia, Sci. Transl. Med., 3:95ra73 (2011).
Karpovsky et al., Production of target-specific effector cells using hetero-cross-linked aggregates containing anti-target cell and anti-Fc gamma receptor antibodies, *J. Exp. Med.*, 160:1686-701 (1984).
Kawashima et al., Pulmonary delivery of insulin with nebulized DL-lactide/glycolide copolymer (PLGA) nanospheres to prolong hypoglycemic effect, *J. Controlled Release*, 62(1-2):279-87 (1999).
Koehler et al., Continuous cultures of fused cells secreting antibody of predefined specificity, *Nature*, 256:495-7 (1975).
Kortt et al., Dimeric and trimeric antibodies: high avidity scFvs for cancer targeting, *Biomol. Eng.*, 18:95-108 (2001).
Kosbor et al., The production of monoclonal antibodies from human lymphocytes, *Immunol. Today*, 4:72 (1983).
Kudo et al., Molecular cloning and characterization of a novel UDP-Gal:GalNAc(alpha) peptide beta 1,3-galactosyltransferase (C1Gal-T2), an enzyme synthesizing a core 1 structure of 0-glycan, *J. Biol. Chem.*, 277:47724-31 (2002).
Langer et al., Biocompatibility of polymeric delivery systems for macromolecules, *J. Biomed. Mater. Res.*, 15:167-277 (1981).
Langer, Controlled release of macromolecules, *Chem. Tech.*, 12:98-105 (1982).
Lanitis et al., Redirected antitumor activity of primary human lymphocytes transduced with a fully human anti-mesothelin chimeric receptor, *Mol. Ther.*, 20:633-43 (2012).
Li et al., Resolving conflicting data on expression of the Tn antigen and implications for clinical trials with cancer vaccines, *Mol. Cancer Ther.*, 8:971-79 (2009).
Liddy et al., Monoclonal TCR-redirected tumor cell killing, *Nat. Med.*, 18(6):980-7 (2012).
Liu et al., Bacterial glycosidases for the production of universal red blood cells, *Nat. Biotechnol.*, 25:454-64 (2007).
Liu et al., Densely Granulated Murine NK Cells Eradicate Large Solid Tumors, *Cancer Res.*, 72:1964-74 (2012).
Liu et al., Pulmonary delivery of free and liposomal insulin, *Pharm. Res.*, 10(2): 228-232 (1993).
Louis et al., Antitumor activity and long-term fate of chimeric antigen receptor-positive T cells in patients with neuroblastoma, *Blood*, 118:6050-6 (2011).
Martin, KabatMan—Query the Kabat Sequence Datatabase (http://www.rubic.rdg.ac.uk/abs/).
McAleese et al., RECRUIT-TandAbs: harnessing the immune system to kill cancer cells, Future Oncol., 8:687-95 (2012).
Milone et al., Chimeric receptors containing CD137 signal transduction domains mediate enhanced survival of T cells and increased antileukemic efficacy in vivo., *Mol. Ther.*, 17:1453-64. (2009).
Monach et al., A unique tumor antigen produced by a single amino acid substitution, *Immunity*, 2:45-59. (1995).
Moore et al., Application of dual affinity retargeting molecules to achieve optimal redirected T-cell killing of B-cell lymphoma, *Blood*, 117:4542 (2011).
Moreau et al., Acquired hemolytic anemia with polyagglutinability of erythrocytes by a new factor present in normal blood, *Bull. Mem. Soc. Med. Hop. Paris*, 73:569-87 (1957).
Morgan et al., Cancer Regression and Neurological Toxicity Following Anti-MAGE-A3 TCR Gene Therapy, *J. Immunother.*, 36:133-51 (2013).
Morgan et al., Case report of a serious adverse event following the administration of T cells transduced with a chimeric antigen receptor recognizing ERBB2, *Mol. Ther.*, 18:843-51 (2010).
Morrison et al., Chimeric human antibody molecules: mouse antigen-binding domains with human constant region domains, *Proc. Natl. Acad. Sci.*, 81:6851-5 (1984).
Mukherjee et al., MUCI-specific immune therapy generates a strong anti-tumor response in a MUCI-tolerant colon cancer model, *Vaccine*, 25:1607-18 (2007).
Nakamura et al., Modification of hematopoietic stem/progenitor cells with CD19-specific chimeric.antigen receptors as a novel approach for cancer immunotherapy, *Human Gene Therapy*, 24:824-39 (2013).
Napoletano et al., Tumor-associated Tn-MUC1 glycoform is internalized through the macrophage galactose-type C-type lectin and delivered to the HLA class I and II compartments in dendritic cells, *Cancer Res.*, 67:8358-67 (2007).
Narni-Mancinelli et al., Fate mapping analysis of lymphoid cells expressing the NKp46 cell surface receptor, *Proc. Natl. Acad. Sci. USA*, 108:18324-9 (2011).
Neeson et al., Ex vivo culture of chimeric antigen receptor T cells generates functional CD8+ T cells with effector and central memory-like phenotype, *Gene Ther.*, 17:1105-16 (2010).
Neuberger et al., Recombinant antibodies possessing novel effector functions, *Nature*, 312:604-8 (1984).
Ninkovic et al., Identification of 0-glycosylated decapeptides within the MUC1 repeat domain as potential MHC class I (A2) binding epitopes, *Mol. Immunol.*, 47:131-40 (2009).
Orlandi et al., Cloning immunoglobulin variable domains for expression by the polymerase chain reaction, *Proc. Natl. Acad. Sci.*, 86:3833-37 (1989).
Owens et al., The genetic engineering of monoclonal antibodies, *J. Immunol. Meth.*, 168:149-65 (1994).
Parkhurst et al., T cells targeting carcinoembryonic antigen can mediate regression of metastatic colorectal cancer but induce severe transient colitis, *Mol. Ther.*, 19:620-6 (2011).
Pedersen et al., Comparison of surface accessible residues in human and murine immunoglobulin Fv domains. Implication for humanization of murine antibodies, *J. Mol. Biol.*, 235:959-73 (1994).
Pedersen et al., Seromic profiling of colorectal cancer patients with novel glycopeptide microarray, *Int. J. Can.*, 128:1860-71 (2011).
Philip et al., Inflammation as a tumor promoter in cancer induction, *Semin. Can. Biol.*, 14:433-9 (2004).
Porter et al., Chimeric antigen receptor-modified T cells in chronic lymphoid leukemia, *N. Engl. J. Med.*, 365:725-33 (2011).
Portner et al., T and NK cells of B cell NHL patients exert cytotoxicity against lymphoma cells following binding of bispecific tetravalent antibody CD19 × CD3 or CD19 × CD16, *Can. Immunol. Immunother.*, 61:1869-75 (2012).
Qian et al., Pulmonary delivery of a GLP-1 receptor agonist, *Int. J. Pharm.*, 366:218-20 (2009).
Qian et al., Sustained release subcutaneous delivery of BMS-686117, a GLP-1 receptor peptide agonist, via a zinc adduct, *Int. J. Pharm.*, 374:46-52 (2009).
Reiter et al., Engineering interchain disulfide bonds into conserved framework regions of Fv fragments: improved biochemical characteristics of recombinant immunotoxins containing.disulfide-stabilized Fv, *Protein Engineering*, 7:697-704 (1994).
Remington's Pharmaceutical Sciences, 18th edition, A. R. Gennaro, ed., Mack Publishing Company (1990).
Reusch et al., A novel tetravalent bispecific TandAb (CD30/CD16A) efficiently recruits NK cells for the lysis of CD30+ tumor cells, *MAbs*, 6:728 (2014).
Riechmann et al., Reshaping human antibodies for therapy, Nature, 332:323-7 (1988).
Roder et al., The EBV-hybridoma technique, Methods Enzymol., 121:140-67 (1986).
Rossi et al., A new class of bispecific antibodies to redirect T cells for cancer immunotherapy, *MAbs*, 6:381-91 (2014).
Sadelain et al., The promise and potential pitfalls of chimeric antigen receptors, *Curr. Opin. Immunol.*, 21:215-23 (2009).

(56) References Cited

OTHER PUBLICATIONS

Sambrook et al. (eds.), Molecular Cloning, A Laboratory Manual, 3rd Edition, Cold Spring Harbor Laboratory Press, New York (2001).
Schietinger et al., A mutant chaperone converts a wild-type protein into a tumor-specific antigen, *Science*, 314:304-8 (2006).
Schietinger et al., Bystander killing of cancer requires the cooperation of CD4(+) and CD8(+) T cells during the effector phase, *J. Exp. Med.*, 207:2469-77 (2010).
Schlereth et al., Eradication of tumors from a human colon cancer cell line and from ovarian cancer metastases in immunodeficient mice by a single-chain Ep-CAM-/CD3-bispecific antibody construct, *Cancer Res.*, 65:2882-9 (2005).
Schlereth et al., Potent inhibition of local and disseminated tumor growth in immunocompetent.mouse models by a bispecific antibody construct specific for Murine CD3, *Can. Immunol. Immunother.*, 55:785-96 (2006).
Schreiber et al., Inflammation and Cancer. In Inflammation: Basic Principles and Clinical.Correlates. J.I. Gallin, and R. Snyderman, editors. Lippincott Williams & Wilkins, Philadelphia, 1117-29 (1999).
Schreiber et al., Spleen cells from young but not old immunized mice eradicate large established cancers, *Clin. Can. Res.*, 18:2526-33 (2012).
Schreiber, Cancer Immunology. In Fundamental Immunology. W.E. Paul, editor Lippincott-Williams & Wilkins, Philadelphia, PA. 1200-34 (2013).
Sidman et al., Controlled release of macromolecules and pharmaceuticals from synthetic polypeptides based on glutamic acid, *Biopolymers*, 22:547-56 (1983).
Sorensen et al., Chemoenzymatically synthesized multimeric Tn/STn MUC1 glycopeptides elicit cancer-specific anti-MUC1 antibody responses and override tolerance, *Glycobiology*, 16:96-107 (2006).
Spiotto et al., Increasing tumor antigen expression overcomes "ignorance" to solid tumors via crosspresentation by bone marrow-derived stromal cells, *Immunity*, 17:737-47. (2002).
Springer et a., Blood group MN antigens and precursors in normal and malignant human breast glandular tissue, *J. Natl. Cancer. Inst.*, 54:335-9. (1975).
Springer et al., Blood group MN specific substances and precursors in normal and malignant human breast tissuesm, *Naturwissenschaften*, 61:457-8. (1974).
Springer, Origin of anti-Thomsen-Friedenreich (T) and Tn agglutinins in man and in White Leghorn chicks, *Br. J. Haematol.*, 47:453-60 (1981).
Springer, Suicide Gene Therapy, Methods and Review, *Meth. Molec. Med.*, (2004).
Springer, T and Tn, general carcinoma autoantigens, *Science*, 224:1198-206 (1984).
Steentoft et al., Characterization of an immunodominant cancer-specific 0-glycopeptide epitope in murine podoplanin (OTS8), *Glycoconj. J.*, 27:571-82 (2010).
Steentoft et al., Mining the 0-glycoproteome using zinc-finger nuclease-glycoengineered SimpleCell lines, *Nat. Meth.*, 8:977-82 (2011).
Stone et al., A sensitivity scale for targeting T cells with chimeric antigen receptors (CARs) and bispecific T-cell Engagers (BiTEs), *Oncoimmunol.*, 1:863-73 (2012).
Suzuki et al., Modulation of microRNA processing by p53, *Nature*, 460:529-33 (2009).
Takeda et al., Construction of chimaeric processed immunoglobulin genes containing mouse variable and human constant region sequences, *Nature*, 314: 452-4 (1985).
Tarp et al., Identification of a novel cancer-specific immunodominant glycopeptide epitope in the MUC1 tandem repeat, *Glycobiology*, 17:197-209 (2007).
Taupier et al., Nonrandom escape of tumor cells from immune lysis due to intraclonal fluctuations in antigen expression, *Cancer Res.*, 43:4050-56 (1983).
Titus et al., Human T cells targeted with anti-T3 cross-linked to antitumor antibody prevent tumor growth in nude mice, *J. Immunol.*, 138:4018-22 (1987).
Todorovska et al., Design and application of diabodies, triabodies and tetrabodies for cancer targeting, *J. Immunol. Meth.*, 248:47-66 (2001).
Van Elssen et al., Expression of aberrantly glycosylated Mucin-1 in ovarian cancer, *Histopathology*, 57:597-606 (2010).
Verhoeyen et al., Reshaping human antibodies: grafting an antilysozyme activity, *Science*, 239:1534-6 (1988).
Vlad et al., Complex carbohydrates are not removed during processing of glycoproteins by dendritic cells: processing of tumor antigen MUC1 glycopeptides for presentation to major histocompatibility complex class II-restricted T cells, *J. Exp. Med.*, 196:1435-46 (2002).
Wandall et al., Cancer biomarkers defined by autoantibody signatures to aberrant 0-glycopeptide epitopes, *Cancer Res.*, 70:1306-13 (2010).
Wang et al., Cosmc is an essential chaperone for correct protein 0-glycosylation, *Proc. Natl. Acad. Sci. USA*, 107:9228-33 (2010).
Ward et al., Tumor antigens defined by cloned immunological probes are highly polymorphic and are not detected on autologous normal cells, *J. Exp. Med.*, 170:217-32 (1989).
Welinder, et al., A new murine IgG1 anti-Tn monoclonal antibody with in vivo anti-tumor activity, *Glycobiology*, 21:1097-107 (2011).
Wen et al., A systematic analysis of experimental immunotherapies on tumors differing in size and duration of growth, *Oncoimmunol.*, 1:172-8 (2012).
Winter et al., Man-made antibodies, *Nature*, 349:293-9 (1991).
Wolfel et al., A p16INK4a-insensitive CDK4 mutant targeted by cytolytic T lymphocytes in a human melanoma, *Science*, 269:1281-4 (1995).
Xia et al., Defective angiogenesis and fatal embryonic hemorrhage in mice lacking core 1-derived 0-glycans, *J. Cell. Biol.*, 164:451-9 (2004).
Yang et al., Phosphorylations of DEAD box p68 RNA helicase are associated with cancer development and cell proliferation, *Mol. Can. Res.*, 3:355-63 (2005).
Yu, The oncofetal Thomsen-Friedenreich carbohydrate antigen in cancer progression, *Glycoconj. J.*, 24:411-20 (2007).
Zhang et al., IFN-gamma- and TNF-dependent bystander eradication of antigen-loss variants in established mouse cancers, *J. Clin. Invest.*, 118:1398-404 (2008).
Zhao et al., A herceptin-based chimeric antigen receptor with modified signaling domains leads to enhanced survival of transduced T lymphocytes and antitumor activity, *J. Immunol.*, 183:5563-74 (2009).

\* cited by examiner

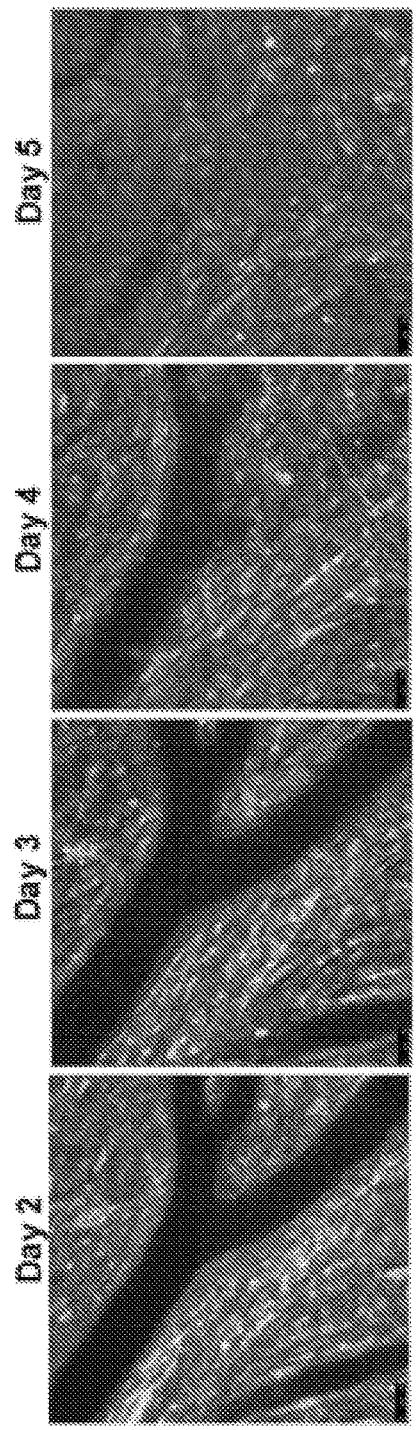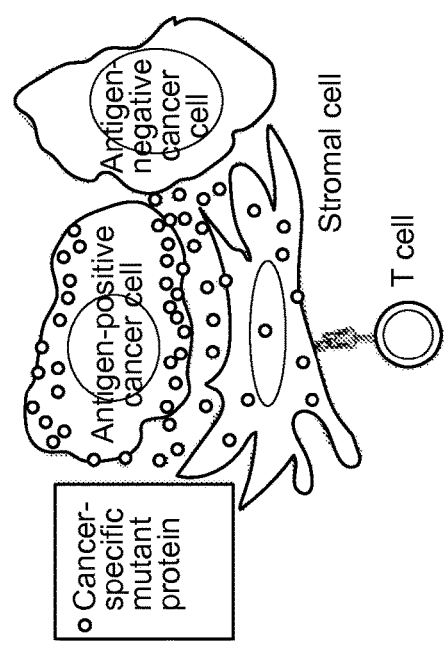
FIGURE 9

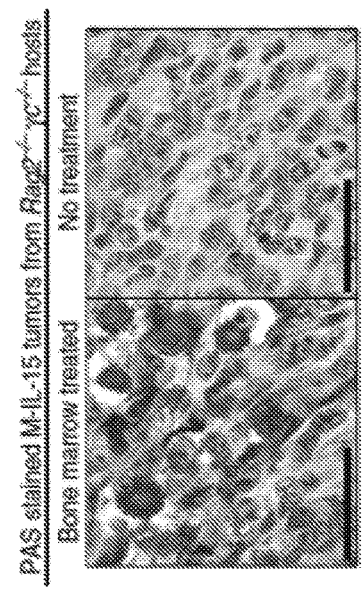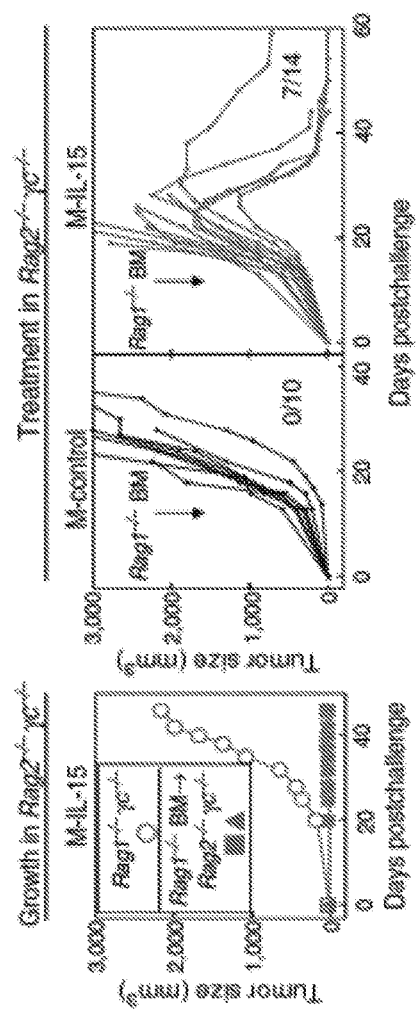
FIGURE 10A  FIGURE 10B  FIGURE 10C

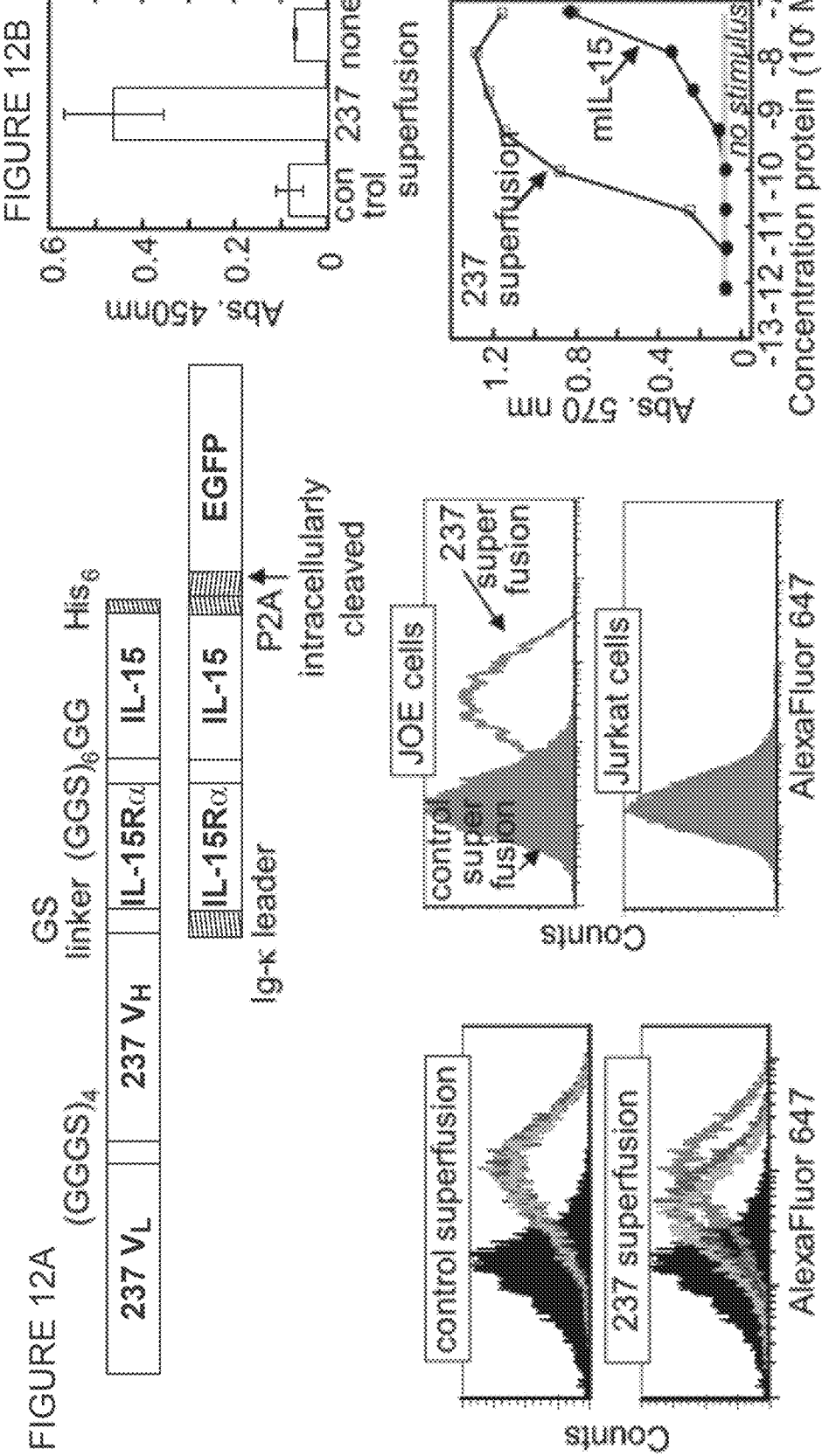

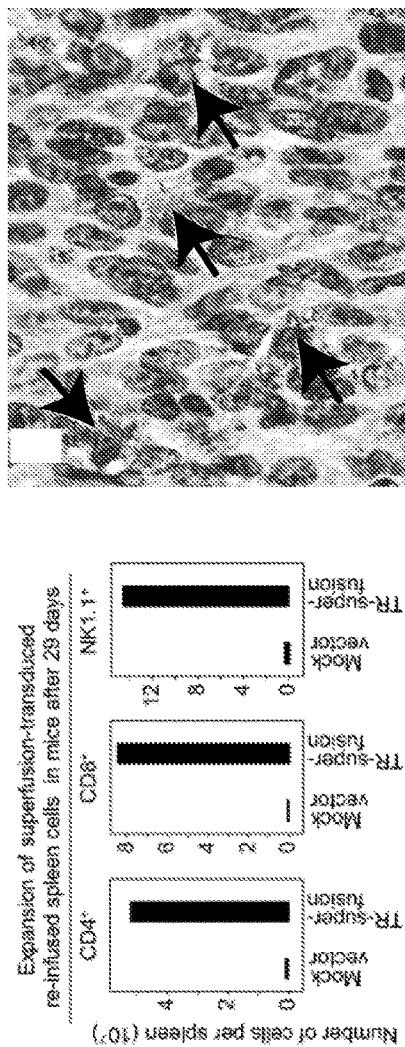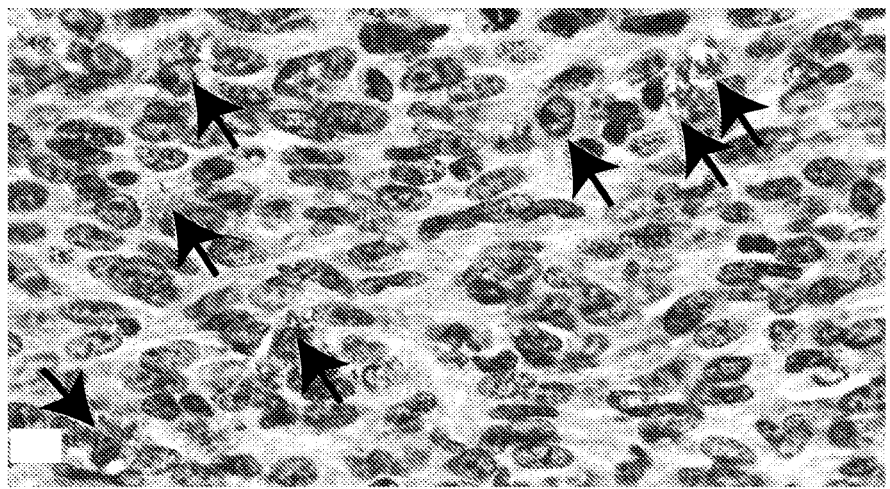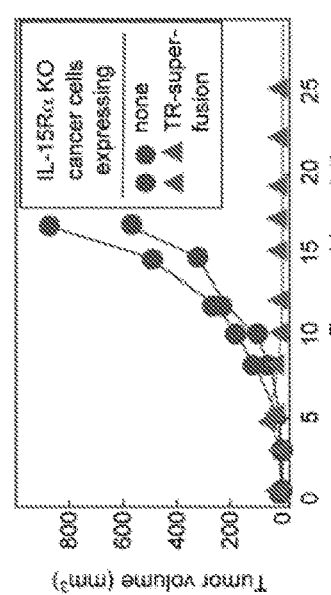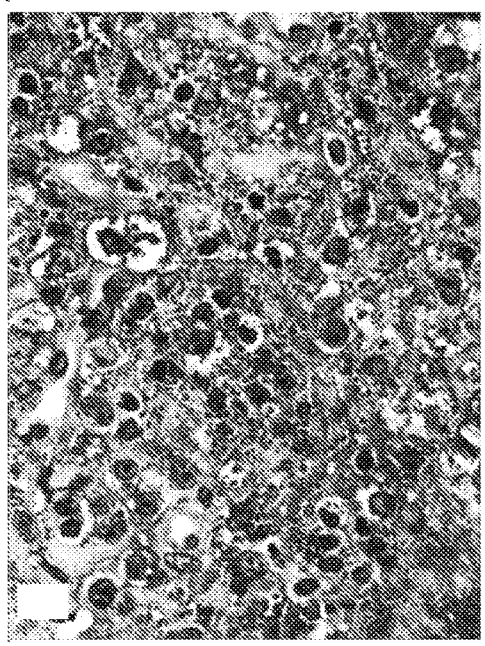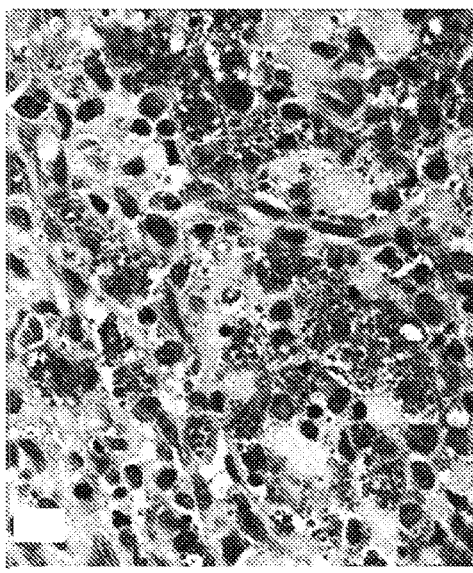
FIGURE 13A
FIGURE 13B
FIGURE 13C
FIGURE 13D
FIGURE 13E

SEQUENCE LISTING

```
<160> NUMBER OF SEQ ID NOS: 29

<210> SEQ ID NO 1
<211> LENGTH: 57
<212> TYPE: DNA
<213> ORGANISM: Artificial Sequence
<220> FEATURE:
<223> OTHER INFORMATION: 5E5 signal sequence, optimized

<400> SEQUENCE: 1
atggaatggt cttgggtgtt cctgttcttc ctgagcgtga ccaccggcgt gcacagc      57

<210> SEQ ID NO 2
<211> LENGTH: 57
<212> TYPE: DNA
<213> ORGANISM: Mus musculus
<220> FEATURE:
<221> NAME/KEY: misc_feature
<223> OTHER INFORMATION: 5E5 signal sequence, original

<400> SEQUENCE: 2
atggaatgga gctgggtctt tctcttcttc ctgtcagtaa ctacaggtgt ccactcc      57

<210> SEQ ID NO 3
<211> LENGTH: 348
<212> TYPE: DNA
<213> ORGANISM: Artificial Sequence
```

```
<220> FEATURE:
<223> OTHER INFORMATION: 5E5 heavy chain, optimized

<400> SEQUENCE: 3
caggtgcagc tgcagcagtc tgatgccgag ctcgtgaagc ctggcagcag cgtgaagatc      60
agctgcaagg ccagcggcta caccttcacc gaccacgcca tccactgggt caagcagaag    120
cctgagcagg gcctggaatg gatcggccac ttcagccccg gcaacaccga catcaagtac    180
aacgacaagt tcaagggcaa ggccaccctg accgtggaca aagcagcag caccgcctac    240 atgcagctga acagcctgac cagcgaggac agcgccgtgt acttctgcaa gaccagcacc    300 ttcttttttcg actactgggg ccagggcaca accctgacag tgtctagc               348

<210> SEQ ID NO 4
<211> LENGTH: 348
<212> TYPE: DNA
<213> ORGANISM: Mus musculus
<220> FEATURE:
<221> NAME/KEY: misc_feature
<223> OTHER INFORMATION: 5E5 heavy chain, original

<400> SEQUENCE: 4
caggttcagc tgcagcagtc tgacgctgag ttggtgaaac ctgggtcttc agtgaagata     60
tcctgcaagg cttctggcta caccttcact gaccatgcta ttcactgggt gaagcagaag   120
cctgaacagg gcctggaatg gattggacat ttttctcccg gaaatactga tattaagtac   180
aatgacaagt tcaagggcaa ggccacactg actgtagaca atcctccag cactgcctac   240 atgcagctca acagcctgac atctgaggat tctgcagtgt atttctgtaa aacgagtacg   300
tttttctttg actactgggg ccaaggcacc actctcacag tctcctca               348

<210> SEQ ID NO 5
<211> LENGTH: 339
<212> TYPE: DNA
<213> ORGANISM: Artificial Sequence
<220> FEATURE:
<223> OTHER INFORMATION: 5E5 light chain, optimized

<400> SEQUENCE: 5
gaactcgtga tgacccagag ccccagctct ctgacagtga cagccggcga gaaagtgacc     60
atgatctgca gtcctcccca gagcctgctg aactccggcg accagaagaa ctacctgacc   120
tggtatcagc agaaacccgg ccagccccc aagctgctga tcttttgggc cagcacccgg   180
gaaagcggcg tgcccgatag attcacaggc agcggctccg gcaccgactt taccctgacc   240
atcagctccg tgcaggccga ggacctggcc gtgtattact gccagaacga ctacagctac   300
cccctgacct tcggagccgg caccaagctg gaactgaag                         339

<210> SEQ ID NO 6
<211> LENGTH: 339
<212> TYPE: DNA
<213> ORGANISM: Mus musculus
<220> FEATURE:
<221> NAME/KEY: misc_feature
<223> OTHER INFORMATION: 5E5 light chain, original

<400> SEQUENCE: 6
gagctcgtca tgacccagtc tccatcctcc ctgactgtga cagcaggaga gaaggtcact     60
atgatctgca gtccagtca gagtctatta acagtggaa tcaaaagaa ctacttgacc      120 tggtaccagc agaaaccagg gcagcctcct aaactttga tcttctgggc atcaacaagg   180
```

```
gagtctgggg tccctgatcg cttcacaggc agtggatctg aacagattt cactctcacc      240 atcagcagtg tacaggctga agacctggca gtttattact gtcagaatga ttatagttat      300
ccgctcacgt tcggtgctgg gaccaaactg gagctgaaa                              339

<210> SEQ ID NO 7
<211> LENGTH: 789
<212> TYPE: DNA
<213> ORGANISM: Artificial Sequence
<220> FEATURE:
<223> OTHER INFORMATION: 5E5 construct

<400> SEQUENCE: 7
atggaatggt cttgggtgtt cctgttcttc ctgagcgtga ccaccggcgt gcacagccag       60
gtgcagctgc agcagtctga tgccgagctc gtgaagcctg gcagcagcgt gaagatcagc      120
tgcaaggcca gcggctacac cttcaccgac acgccatcc actgggtcaa gcagaagcct       180
gagcagggcc tggaatggat cggccacttc agccccggca acaccgacat caagtacaac      240
gacaagttca agggcaaggc cacgctgacc gtggacagaa gcagcagcac cgcctacatg      300
cagctgaaca gcctgaccag cgaggacagc gccgtgtact tctgcaagac cagcaccttc      360
tttttcgact actggggcca gggcacaacc ctgacagtgt ctagcggcgg aggcggatct      420
ggcggcggag gatctggggg aggcggctct gaactcgtga tgacccagag ccccagctct      480
ctgacagtga cagccggcga aaagtgacc atgatctgca gtcctcccca gagcctgctg      540
aactccggcg accagaagaa ctacctgacc tggtatcagc agaaacccgg ccagcccccc      600
aagctgctga tcttttgggc cagcacccgg gaaagcggcg tgcccgatag attcacaggc      660
agcggctccg gcaccgactt taccctgacc atcagctccg tgcaggccga ggacctggcc      720
gtgtattact gccagaacga ctacagctac cccctgacct tcggagccgg caccaagctg      780
gaactgaag                                                              789

<210> SEQ ID NO 8
<211> LENGTH: 57
<212> TYPE: DNA
<213> ORGANISM: Artificial Sequence
<220> FEATURE:
<223> OTHER INFORMATION: 3H4 signal sequence, optimized

<400> SEQUENCE: 8
atgggctggt cctgcatcat cctgtttctg gtggccacag ccaccggcgt gcacagc          57

<210> SEQ ID NO 9
<211> LENGTH: 342
<212> TYPE: DNA
<213> ORGANISM: Artificial Sequence
<220> FEATURE:
<223> OTHER INFORMATION: 3H4 heavy chain, optimized

<400> SEQUENCE: 9
caggtgcagc tggaagaatc tggccctggc ctggtggccc ctagccagag cctgagcatc       60
acatgcaccg tgtccggctt ctccctgacc tcctatggcg tgtcatgggt gcgacagcct      120
ccaggcaagg gcctggaatg gctgggagtg atttggggcg acggcagcac caactaccac      180
agcgccctga tcagcagact gagcatctcc aaggacaaca gcaagagcca ggtgttcctg      240
aagctgaaca gcctgcagac cgacgacaca gccacatatt actgcgccaa gggcggctac      300
ttcgactact ggggccaggg cacaaccctg accgtgtcta gt                         342
```

```
<210> SEQ ID NO 10
<211> LENGTH: 342
<212> TYPE: DNA
<213> ORGANISM: Mus musculus
<220> FEATURE:
<221> NAME/KEY: misc_feature
<223> OTHER INFORMATION: 3H4 heavy chain, original

<400> SEQUENCE: 10
caggtgcagc tcgaggagtc aggacctggc ctggtggcgc cctcacagag cctgtccatc      60
acatgcactg tctcagggtt ctcattaacc agctatggtg taagctgggt tcgccagcct     120
ccaggaaagg gtctggagtg gctgggagta atatggggtg acgggagcac aaattatcat     180
tcagctctca tatccagact gagcatcagc aaggataact ccaagagcca agttttctta     240
aaactgaaca gtctgcaaac tgatgacaca gccacgtact actgtgccaa agggggtac     300 tttgactact ggggccaagg caccactctc acagtctcct ca                        342

<210> SEQ ID NO 11
<211> LENGTH: 318
<212> TYPE: DNA
<213> ORGANISM: Artificial Sequence
<220> FEATURE:
<223> OTHER INFORMATION: 3H4 light chain, optimized

<400> SEQUENCE: 11
cagattgtgc tgacacagag ccccgccatc atgagcgcta gccctggcga gaaagtgacc      60
atcacctgta gcgccagcag cagcgtgtcc tacatgcact ggttccagca gaagcccggc     120
accagcccca agctgtggat ctacagcacc agcaacctgg ccagcggcgt gcccgctaga     180
ttttctggca gcggctctgg caccagctac agcctgacca tcagcagaat ggaagccgag     240
gacgccgcca cctactactg ccagcagaga agcagctacc ccttcacctt cggcagcggc     300
accaagctgg aaatcaag                                                   318

<210> SEQ ID NO 12
<211> LENGTH: 318
<212> TYPE: DNA
<213> ORGANISM: Mus musculus
<220> FEATURE:
<221> NAME/KEY: misc_feature
<223> OTHER INFORMATION: 3H4 light chain, original

<400> SEQUENCE: 12
caaattgttc tcacccagtc tccagcaatc atgtctgcat ctccagggga gaaggtcacc      60
ataacctgca gtgccagctc aagtgtaagt tacatgcact ggttccagca gaagccaggc     120
acttctccca aactctggat ttatagcaca tccaacctgg cttctggagt ccctgctcgc     180
ttcagtggca gtggatctgg gacctcttac tctctcacaa tcagccgaat ggaggctgaa     240
gatgctgcca cttattactg ccagcaaagg agtagttacc cattcacgtt cggctcgggg     300
acaaagttgg aaataaaa                                                   318

<210> SEQ ID NO 13
<211> LENGTH: 762
<212> TYPE: DNA
<213> ORGANISM: Artificial Sequence
<220> FEATURE:
<223> OTHER INFORMATION: 3H4 construct
```

-continued

<400> SEQUENCE: 13

```
atgggctggt cctgcatcat cctgtttctg gtggccacag ccaccggcgt gcacagccag    60
attgtgctga cacagagccc cgccatcatg agcgctagcc ctggcgagaa agtgaccatc   120
acctgtagcg ccagcagcag cgtgtcctac atgcactggt ccagcagaa gcccggcacc   180
agccccaagc tgtggatcta cagcaccagc aacctggcca gcggcgtgcc cgctagattt   240
tctggcagcg gctctggcac cagctacagc ctgaccatca gcagaatgga agccgaggac   300
gccgccacct actactgcca gcagagaagc agctacccct tcaccttcgg cagcggcacc   360
aagctggaaa tcaagggcgg aggcggatct ggcggcggag gatctggggg aggcggctct   420
caggtgcagc tggaagaatc tggccctggc ctggtggccc ctagccagag cctgagcatc   480
acatgcaccg tgtccggctt ctccctgacc tcctatggcg tgtcatgggt gcgacagcct   540
ccaggcaagg gcctggaatg gctgggagtg atttggggcg acggcagcac caactaccac   600
agcgccctga tcagcagact gagcatctcc aaggacaaca gcaagagcca ggtgttcctg   660
aagctgaaca gcctgcagac cgacgacaca gccacatatt actgcgccaa gggcggctac   720
ttcgactact ggggccaggg cacaaccctg accgtgtcta gt                      762
```

<210> SEQ ID NO 14
<211> LENGTH: 45
<212> TYPE: DNA
<213> ORGANISM: Artificial Sequence
<220> FEATURE:
<223> OTHER INFORMATION: Linker

<400> SEQUENCE: 14

```
ggcggaggcg gatctggcgg cggaggatct ggggaggcg gctct                     45
```

<210> SEQ ID NO 15
<211> LENGTH: 19
<212> TYPE: PRT
<213> ORGANISM: Artificial Sequence
<220> FEATURE:
<223> OTHER INFORMATION: 5E5 signal peptide

<400> SEQUENCE: 15

Met Glu Trp Ser Trp Val Phe Leu Phe Phe Leu Ser Val Thr Thr Gly
1               5                   10                  15

Val His Ser

<210> SEQ ID NO 16
<211> LENGTH: 116
<212> TYPE: PRT
<213> ORGANISM: Artificial Sequence
<220> FEATURE:
<223> OTHER INFORMATION: 5E5 heavy chain

<400> SEQUENCE: 16

Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
                20                  25                  30

Ala Ile His Trp Val Lys Gln Lys Pro Glu Gln Gly Leu Glu Trp Ile
            35                  40                  45

Gly His Phe Ser Pro Gly Asn Thr Asp Ile Lys Tyr Asn Asp Lys Phe
        50                  55                  60

Lys Gly Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Gly Thr Thr Leu
            100                 105                 110

Thr Val Ser Ser
        115

<210> SEQ ID NO 17
<211> LENGTH: 113
<212> TYPE: PRT
<213> ORGANISM: Artificial Sequence
<220> FEATURE:
<223> OTHER INFORMATION: 5E5 light chain

<400> SEQUENCE: 17

Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 18
<211> LENGTH: 19
<212> TYPE: PRT
<213> ORGANISM: Artificial Sequence
<220> FEATURE:
<223> OTHER INFORMATION: 3H4 signal peptide, optimized

<400> SEQUENCE: 18

Met Gly Trp Ser Cys Ile Ile Leu Phe Leu Val Ala Thr Ala Thr Gly
1               5                   10                  15

Val His Ser

<210> SEQ ID NO 19
<211> LENGTH: 114
<212> TYPE: PRT
<213> ORGANISM: Artificial Sequence
<220> FEATURE:
<223> OTHER INFORMATION: 3H4 heavy chain

<400> SEQUENCE: 19

Gln Val Gln Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

```
Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Gly Tyr Phe Asp Tyr Trp Gly Gln Gly Thr Thr Leu Thr Val
            100                 105                 110

Ser Ser

<210> SEQ ID NO 20
<211> LENGTH: 106
<212> TYPE: PRT
<213> ORGANISM: Artificial Sequence
<220> FEATURE:
<223> OTHER INFORMATION: 3H4 light chain

<400> SEQUENCE: 20

Gln Ile Val Leu Thr Gln Ser Pro Ala Ile Met Ser Ala Ser Pro Gly
  1               5                  10                  15

Glu Lys Val Thr Ile Thr Cys Ser Ala Ser Ser Ser Val Ser Tyr Met
                 20                  25                  30

His Trp Phe Gln Gln Lys Pro Gly Thr Ser Pro Lys Leu Trp Ile Tyr
             35                  40                  45

Ser Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                 85                  90                  95

Phe Gly Ser Gly Thr Lys Leu Glu Ile Lys
            100                 105

<210> SEQ ID NO 21
<211> LENGTH: 15
<212> TYPE: PRT
<213> ORGANISM: Artificial Sequence
<220> FEATURE:
<223> OTHER INFORMATION: Linker

<400> SEQUENCE: 21

Gly Gly Gly Gly Ser Gly Gly Gly Gly Ser Gly Gly Gly Gly Ser
  1               5                  10                  15

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Ser Ile Tyr Arg Tyr Tyr Gly Leu
  1               5

<210> SEQ ID NO 23
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 23
gcggccgcca cc                                                          12
```

```
<210> SEQ ID NO 24
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 24 ctcgag                                                                     6

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide linker

<400> SEQUENCE: 25

Glu Glu Gly Glu Phe Ser Glu Ala Arg
1               5

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide linker

<400> SEQUENCE: 26

Ala Lys Thr Thr Pro Pro Lys Leu Glu Glu Gly Glu Phe Ser Glu Ala
1               5                   10                  15

Arg Val

<210> SEQ ID NO 27
<211> LENGTH: 21
<212> TYPE: PRT
<213> ORGANISM: Homo sapiens

<400> SEQUENCE: 27

Met Glu Thr Asp Thr Leu Leu Leu Trp Val Leu Leu Leu Trp Val Pro
1               5                   10                  15

Gly Ser Thr Gly Asp
            20

<210> SEQ ID NO 28
<211> LENGTH: 14
<212> TYPE: PRT
<213> ORGANISM: Artificial Sequence
<220> FEATURE:
<223> OTHER INFORMATION: Synthetic Myc tag

<400> SEQUENCE: 28

Gly Gly Pro Glu Gln Lys Leu Ile Ser Glu Glu Asp Leu Asn
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Synthetic His tag

<400> SEQUENCE: 29

His His His His His His
1               5
```

CHIMERIC ANTIGEN RECEPTORS RECOGNIZING CANCER-SPECIFIC TN GLYCOPEPTIDE VARIANTS This application claims the priority benefit of provisional U.S. patent application No. 61/936,304, filed Feb. 5, 2014, which is incorporated herein by reference in its entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 48054A_SeqListing.txt; 14,971 bytes, created Feb. 4, 2015.

FIELD OF THE DISCLOSURE

The disclosure relates generally to the fields of cancer biology and to molecular antibody-receptor technology.

BACKGROUND

Cancer is a major threat to human and non-human animal health, leading to reduced quality of life and, in too many cases, death. The burden placed on national, regional and local healthcare organizations to treat and prevent the various forms of cancer is significant in terms of the resources and manpower required. One of the main weapons vertebrates, including humans, have to combat disease is a functioning immune system. A brief consideration of immunotherapies to treat or prevent cancer might lead one to conclude that the effort held out little hope of success because immune systems guard against foreign, or non-self, materials and cancer cells arise from within, i.e., they are self materials. Continued progress in our understanding of cancer and immunology is modifying that view, however.

Mutant antigens are powerful targets for tumor destruction, e.g., in mice, and tumor-infiltrating lymphocytes targeting these mutations cause durable tumor regression in patients. Nevertheless, non-mutant antigens have been presumed by many scientists to be cancer-specific or "relatively cancer-specific" and safe antigens for vaccine approaches. However, adoptively transferred T cells can be orders of magnitude more effective and destructive than vaccinations. As a result, targeting MAGE-A3, HER-2 or CEA with T cells has caused death or serious toxicity in clinical trials now halted (8-11). As was shown in 2002, cancer cells with extremely high or very low expression levels of a target antigen differ only in the induction of immune responses, but not at the effector phase (15).

A publication in 1995 (6) established that somatic tumor-specific mutations resulting in mutant peptides are the cause of unique antigens, which are recognized by tumor-specific T cells. This was subsequently confirmed by many independent laboratories in studies on human and mice (e.g., 23-25). There it was shown that the unique immunodominant antigen on the UV-induced tumor 8101 was caused by a single base-pair substitution in the p68 oncogenic RNA helicase, a critical microRNA regulator protein (26-28).

Non-mutant antigens can nevertheless be cancer-specific antigens and safe targets for adoptive T cell transfer, and this realization involves a shift in focus from previous work caused by the discovery that Tn-O-glycopeptides occur as cancer-specific antigens, as disclosed in Science in 2006 (16). Tn antigen (1, 2) is expressed by a majority of common cancers of diverse origin and it is one of the earliest antigens identified on human tumors (FIG. 4) (18-20). Importantly, the peptide sequence is not part of the Tn antigen and not recognized by anti-Tn antibodies (for review see (12)). Antibodies that specifically bind only Tn are usually IgM and of limited use, i.e., for histochemistry but probably not CARs (Table 2). Occasional IgG-class anti-Tn antibodies are of poor specificity and affinity, and may slightly delay the outgrowth of Tn-expressing transplanted cancer cells when used in animals (54, 55).

It is likely that about 70-90% of common human cancers, such as breast, colon, prostate, ovary, lung, bladder and cervix cancers, express Tn (12). Conflicting data on the magnitude of expression of Tn on human tumors (56) can be largely explained by differences in affinities of the large number of different antibodies that have been experimentally produced most of them of very poor quality (with very few exceptions such as the IgM 5F4). Apparently, it is difficult for the epitope binding site of antibodies to bind the single sugar molecule with high affinity and specificity. While TF antigen (FIG. 1) is an oncofetal antigen highly expressed in the embryo and fetus (57), there is less evidence that Tn is also an oncofetal antigen (12), even though Tn antigens have been reported to be expressed perinatally in the brain but rapidly declining after birth (58). Most adults naturally have anti-Tn as well as anti-TF antibodies, probably due to antigenic stimulation by Tn and TF antigens expressed on the bacterial flora (13, 14); Tn antigen is also expressed on HIV-1 and pathogenic parasites (12).

Even though Tn was discovered by Dausset half a century ago (2) and Tn-expression on cancer cells over 40 years ago (18-21), technological advances that allowed the sophistication and rapid expansion of glyco-chemistry and glycobiology were only made in the last decade. There are still huge defects in our understanding of this field. As a further point on specificity, there is longstanding evidence for tolerance to many cancer testis antigens, HER-2 and CEA, indicating their expression on normal tissues and ultimately absence of true cancer specificity. By contrast, Tn-O-glycopeptides consistently have given the opposite result.

Most human cancers lack specific antigens that are predictably present and serve as effective targets for eradication by T cells. Every cancer cell type harbors a unique set of mutations causing different tumor-specific antigens. Identifying an effective unique antigen and isolating an appropriate TCR for transduction of autologous T cells for adoptive immunotherapy is still difficult despite the enormous technological progress being made. Adoptive immunotherapy using antibodies or T cells is clinically as well as experimentally the most effective immunotherapy, at least when clinically relevant cancers are considered (22). The remarkable success of adoptive immunotherapy with chimeric antibody receptors (CARs) and bispecific T cell engaging proteins (BiTEs) is, however, largely restricted to those specific for CD19/CD20-eradicating B cell malignancies and normal B cells in patients, i.e., hematopoietic cancers. Thus, there is a need to identify shared, yet tumor-specific, antigens on a wide range of solid tumors, and a concomitant need to develop prophylactics and therapeutics that can diagnose, prevent, treat or ameliorate a symptom of these cancers, along with methods for diagnosing, preventing and treating various cancers.

SUMMARY

The disclosure captures the tumor specificity of glycopeptide variants by providing protein binding partners specific for cancer-specific moieties. In addition, the disclosure provides a polynucleotide encoding one of these cancer-specific Tn glycopeptide binding partners, including polynucleotides comprising codon-optimized coding regions for binding partners specific for an epitope of one of these variant glycopeptides, which are not found at detectable levels in the wild-type counterpart to the variant glycopeptide. Expressly contemplated are fusion proteins or chimeras that comprise a binding partner as defined above in operable linkage to a peptide providing a second function, such as a signaling function of the signaling domain of a T cell signaling protein, a peptide modulator of T cell activation or an enzymatic component of a labeling system. Exemplary T cell signaling proteins include 4-1BB, CD3ζ, and fusion peptides, e.g., CD28-CD3ζ and 4-1BB-CD3ə. 4-1BB, or CD137, is a co-stimulatory receptor of T cells; CD3ζ is a signal-transduction component of the T-cell antigen receptor. The peptide providing a second function may provide a modulator of T cell activation, such as IL-15, IL-15Rα, of an IL-15/IL-15Rα fusion, or it may encode a label or an enzymatic component of a labeling system useful in monitoring the extent and/or location of binding, in vivo or in vitro. Constructs encoding these prophylactically and therapeutically active biomolecules placed in the context of T cells, such as autologous T cells, provide a powerful platform for recruiting adoptively transferred T cells to prevent or treat a variety of cancers in some embodiments of the disclosure. Codon optimization of the coding regions for binding partners specific for epitopes found on cancer cells provides an efficient approach to delivery of the diagnostic, prophylactic, and/or therapeutic proteins disclosed herein.

In one aspect, the disclosure provides a cancer-specific Tn glycopeptide binding partner that binds a cancer-specific Tn glycopeptide, such as MUC1, the binding partner comprising the antibody heavy chain variable fragment (VH) sequence set forth in SEQ ID NO:19 and/or the antibody light chain variable fragment (VL) sequence set forth in SEQ ID NO:20. In some embodiments, the Tn glycopeptide is MUC1. In some embodiments, the binding partner comprises a sequence that is at least 95%, 98%, 99%, or 99.5% identical to SEQ ID NOs:19 or 20. In some embodiments, the binding partner comprises the antibody heavy chain variable fragment (VH) of SEQ ID NO:19 or a humanized derivative thereof and the antibody light chain variable fragment (VL) of SEQ ID NO:20 or a humanized derivative thereof. This aspect of the disclosure contemplates any of the above-described binding partners wherein the binding partner is a single-chain variable fragment (scFv). An exemplary scFv comprises the heavy chain variable fragment N-terminal to the light chain variable fragment. In some embodiments, the scFv heavy chain variable fragment and light chain variable fragment are covalently bound to a linker sequence of 4-15 amino acids. In some embodiments, the scFv heavy chain variable fragment comprises SEQ ID NO:19 and the light chain variable fragment comprises SEQ ID NO:20. In some embodiments, the single-chain variable fragment is contained within a bi-specific T-cell engager or within a chimeric antigen receptor (i.e., CAR).

Another aspect of the disclosure is drawn to a polynucleotide comprising a coding region for a cancer-specific Tn glycopeptide binding partner variable region as disclosed herein. In some embodiments of the polynucleotide according to the disclosure, the coding region is codon-optimized for expression in a human cell. Exemplary polynucleotides comprising codon-optimized coding regions include a polynucleotide wherein the coding region for the heavy chain variable fragment is set forth in SEQ ID NO:9 and the coding region for the light chain variable fragment is set forth in SEQ ID NO:11. In some embodiments, the polynucleotide encodes a cancer-specific Tn glycopeptide binding partner selected from the group consisting of a single-chain variable fragment, a multimer of a single-chain variable fragment, a bi-specific single-chain variable fragment and a multimer of a bi-specific single-chain variable fragment. In some embodiments, the multimer of a single-chain variable fragment is selected from the group consisting of a divalent single-chain variable fragment, a tribody and a tetrabody. In some of these embodiments, the multimer of a bi-specific single-chain variable fragment is a bi-specific T-cell engager.

In some embodiments, the polynucleotide according to the disclosure further comprises a coding region for a peptide selected from the group consisting of a peptide signaling domain of a T cell signaling protein, a peptide modulator of T cell activation, and an enzymatic component of a labeling system. In some embodiments, the peptide signaling domain of a T cell signaling protein is selected from the group consisting of a 4-1BB cytosolic signaling domain, a CD3ζ cytosolic signaling domain, a cytosolic domain of CD28-CD3ζ fusion and a cytosolic domain of a 4-1BB-CD3ζ. fusion. In some embodiments, the peptide modulator of T cell activation is selected from the group consisting of IL15, IL15Rα and an IL15/IL15Rα fusion peptide.

The polynucleotide according to the disclosure may further comprise a coding region for a linker peptide, such as a codon-optimized linker coding region as set forth in SEQ ID NO:14. In some embodiments, the polynucleotide further comprises a coding region for a signal peptide, such as a codon-optimized signal peptide coding region as set forth in SEQ ID NO:1 or SEQ ID NO:8. In some embodiments, the polynucleotide further comprises a sequence encoding a transmembrane domain, such as the transmembrane domain of CD28.

Another aspect of the disclosure is directed to a vector comprising the polynucleotide disclosed herein. In some embodiments, the vector is a viral vector. In some embodiments, the viral vector is a lentiviral vector. A related aspect of the disclosure provides a host cell comprising a polynucleotide or vector according to the disclosure.

Yet another aspect of the disclosure is a pharmaceutical composition comprising the polynucleotide, vector or host cell according to the disclosure, and a physiologically suitable buffer, adjuvant or diluent.

Still another aspect of the disclosure is a method of making a chimeric antigen receptor comprising incubating a cell comprising a polynucleotide or a vector according to the disclosure, under conditions suitable for expression of the coding region and collecting the chimeric antigen receptor.

Another aspect of the disclosure is a method of preventing, treating or ameliorating a symptom of a cancer comprising administering a prophylactically or therapeutically effective amount of a polynucleotide or vector according to the disclosure to a subject in need.

Other features and advantages of the present disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWING

FIG. 9. Vessel destruction in large solid tumors following T cell transfer. Activated 2C T cells were adoptively transferred into 18 day established MC57-SIY-EGFP-bearing DsRed-$Rag^{-/-}$ hosts. The same tumor area was imaged at the indicated time points (day 2-5 post T cell transfer). Antigen-positive cancer cells are green, 2C T cells yellow (EYFP) and antigen-negative MC57 cells (18% of the inoculum) cerulean-blue as model of variants. The blue "variants" die inside the necrotizing tumor due to stromal antigen cross-presentation. Similar variant destruction is not expected in the $Kb^{-/-}$ $Db^{-/-}$ mice in which variants, when present, escape treatment of MC57-mp68-EGFP tumors with 1D9TCR-transduced T cells.

FIG. 10. Adoptive transfer of Rag1$^{-/-}$ bone marrow (BM) cells prevents cancer development and can also eradicate established M-IL-15 tumors. A. Recipient Rag2$^{-/-}$ γc$^{-/-}$ mice received BM from Rag1$^{-/-}$ donors 2 months before challenge with M-IL-15 cells. B. Rag2$^{-/-}$ γc$^{-/-}$ mice were challenged s.c. with M-control (black) or M-IL-15 (red) cells. Mice were injected with Rag1$^{-/-}$ BM cells i.v. at day 12 to 14. Numbers indicate eradicated tumors per number of tumors treated (P<0.02). C. Infiltrates of densely granulated leukocytes resembling uterine NK cells are found in M-IL-15 tumors in Rag2$^{-/-}$ γc$^{-/-}$ mice that received Rag1$^{-/-}$ BM. Tumor sections were stained with PAS and diastase. For comparison, an untreated M-IL-15 tumor grown in a Rag2$^{-/-}$ γc$^{-/-}$ mouse is shown. Scale bar, 100 µm. Adapted from (7).

FIG. 12. 237-superfusion protein is functional in vitro. A. Schematic diagrams of the superfusion proteins guided to cancer cells by the 237 receptor or by transduction and secretion. The lower construct is cleaved while being translated; IL15/IL15Rα is secreted due to the Ig-κ leader while EGFP is retained in the cytoplasm. B. 237-superfusion was produced in HEK-293F cells and purified by size exclusion. Purification pools were tested by ELISA using immobilized OTS8 glycopeptide and detecting IL15Rα. C. 237-superfusion competes 237 antibody binding on AG104A cells. Superfusion was incubated 30 min on ice, then 237 antibody was added and incubated for additional 90 min. 237 was detected using an Alexa Fluor 647 labeled anti-mouse secondary antibody. Black: secondary only, red: 237, blue: 237+1 µM superfusion, green: 237+5 µM superfusion. A control superfusion could not compete 237 binding. D. Specific binding of 237-superfusion to Jurkat transduced with OTS8 (JOE). E. 237 superfusion stimulated IL15-dependent CTLL-2 cell proliferation more potently than recombinant murine.

FIG. 13. Superfusion constructs are functional in vivo. A IL-15Rα deficient cancer cells secreting the transduced (TR) superfusion do not grow in Rag$^{-/-}$ mice while non-transduced cancer cells grow out. B Splenocytes expressing TR-superfusion expand in vivo. Wild-type splenocytes were transduced to express the TR-superfusion or a mock protein and transferred in Rag$^{-/-}$ mice. After 29 days spleens were analyzed regarding numbers on CD4$^+$, CD8$^+$ and NK cells. C-E 237-superfusion induces densely granulated NK cells in vivo. C3H mice received an osmotic pump delivering 237-superfusion or PBS s.c. (150 µg/kg per day) and an inoculum of AG104A two days later. Tumors formed in both mice but induction of highly granulated NK cells was detected in the skin surrounding the pump outlet (C, D) and in the tumor (green arrows, E) of the mouse receiving 237-superfusion.

DETAILED DESCRIPTION

Figure 1:
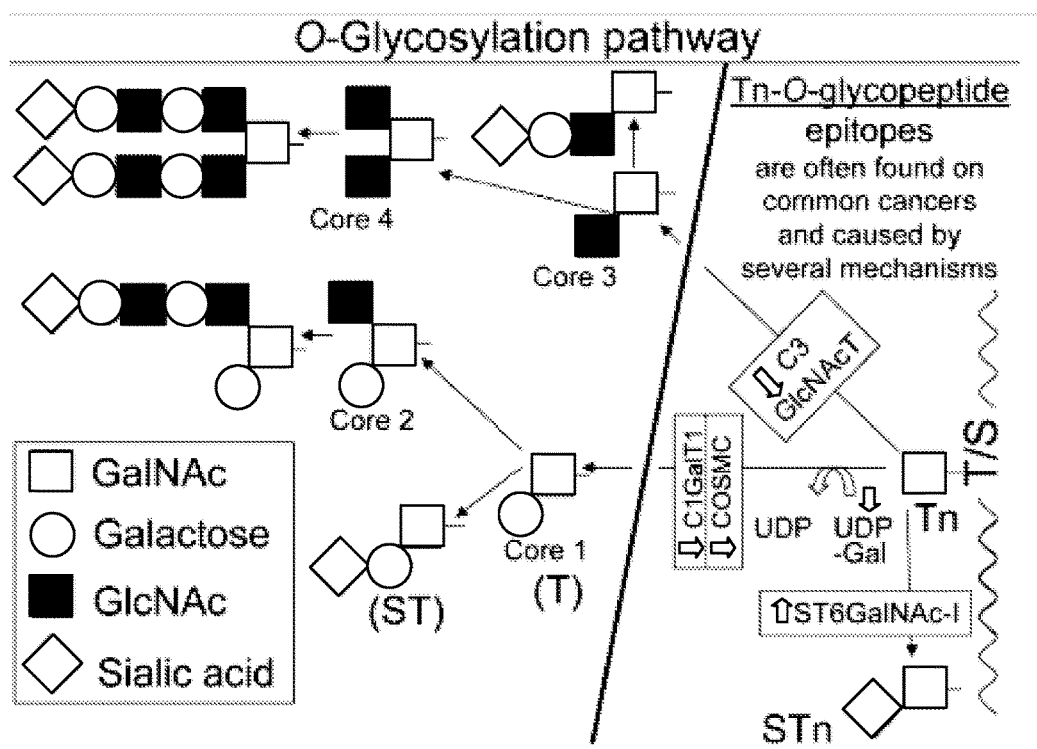
FIG. 1. Tn-expression is a transient stage in intracellular biosynthesis of any glycopeptide when GalNAc is linked to the nascent polypeptide chain. This step is differentially regulated by 20 distinct polypeptide GalNAc transferases that are selectivity expressed in certain cell-types and have different specificity for proteins and sites of glycosylation. Tn will, however, be exposed on the cell surface if the extension of Tn is inhibited: through, as indicated by purple arrows (i) dysfunctional single pathway/single gene transferases: Core1 β1,3-galactosyltransferase (C1GalT or T synthase) and/or Core3 β1,3-N-acetylglucosaminyltransferase (C3GlcNAcT), (ii) dysfunctional chaperone Cosmc that prevents degradation of C1GalT by endoplasmic reticulum-associated degradation (ERAD), (iii) low levels of the substrate UDP-Gal and (iv) higher activity of the ST6 N-acetylgalactosaminide a-2,6-sialyltransferase 1 (ST6GalNAc-I).

The disclosure provides protein binding partners specific for glycopeptide variants associated with cancers, e.g., tumors. In addition, the disclosure provides a polynucleotide encoding one of these cancer-specific Tn glycopeptide binding partners, including polynucleotides comprising codon-optimized coding regions for binding partners specific for an epitope of one of these variant glycopeptides, which are not found at detectable levels in the wild-type counterpart to the variant glycopeptide. The disclosure provides binding partners specific for a cancer-specific Tn glycopeptide, such as MUC1, as well as polynucleotides encoding such binding partners, including codon-optimized polynucleotides. The polynucleotides of the disclosure encode bi-functional polypeptides of the disclosure useful in preventing, treating, or ameliorating a symptom of cancer, such as any of a variety of human cancers, including those forming solid tumors.

Some embodiments of the disclosure provide an unexpected variation on codon optimization in slower-growing higher eukaryotes such as vertebrates, e.g., humans, that is focused on translation optimization (maximizing high-fidelity translation rates) rather than the typical codon optimization used in such organisms, which is designed to accommodate mutational bias and thereby minimize mutation. Also disclosed are the methods of diagnosing, treating or ameliorating a symptom of a cancer. Schematically described, the polynucleotides comprise a codon-optimized coding region for an antigen receptor specifically recognizing a tumor-specific Tn-O-glycopeptide epitope linked to any one of the following: a coding region for a T cell signaling domain involved in T cell activation, a gene product that affects or modulates an immunological response to cancer cells such as an IL15/IL15Rα fusion, or a labeling component such as an enzymatic component of a labeling system. The linked coding regions result in polynucleotides encoding chimeric antigen receptors, or CARs.

The terms used throughout this disclosure are given their ordinary and accustomed meanings in the art, unless a different meaning is made clear from the text when considered in the context of the disclosure as a whole.

The technology addresses the most serious obstacle to progress in immunotherapy, i.e., the virtual absence of defined, truly tumor-specific antigens that can be predictably found on at least a larger subgroup of human cancers and that can serve as effective targets for cancer eradication. Finding such antigens would move the field beyond the methods for treating CD19/CD20-expressing B cell malignancies.

The disclosure is based, at least in part, on the discovery that a tumor-specific defect in O-linked glycosylation in spontaneous human as well as murine cancers converts a wild-type protein into a tumor-specific antigen, e.g., a Tn-O-linked glycopeptide recognized by high-affinity IgG antibody 237. This prototype antigen is used as a target in experiments disclosed herein. Also disclosed is evidence that analogous tumor-specific Tn-O-glycopeptide epitopes are expressed on common human cancers, which are Tn-positive due to deglycosylation, essential for aggressive malignant growth and caused by several independent mechanisms (including, but not dependent on, Cosmc mutations). The VL and VH variable regions of the 237 antibody have been engineered into a single chain (sc) variable fragment (scFv) to generate chimeric antigen receptors (i.e., CARs) for introduction into T cells for adoptive transfer. Thus, CAR-transduced T cells are expected to target a tumor-specific Tn-O-glycopeptide epitope, leading to eradication of solid non-hematopoietic tumors in a syngeneic mouse model. It is believed that CAR-transduced T cells recognizing Tn-O-glycopeptide epitopes will destroy large solid non-hematopoietic tumors. CAR-transduced T cells, however, target cancer cells only directly and antigen-negative cancer cells may escape. Disclosed herein is evidence that, under certain conditions, exquisitely antigen-specific TCR-transduced T cells eliminate antigen-negative cancer cells as bystanders, even in the absence of cross-presentation. It is expected that CAR-transduced T cells will be equally effective in eliminating antigen-negative cancer cells via the bystander effect. Moreover, it is expected that fusion proteins bearing the coding regions for IL15 linked to IL15Rα can be delivered to large solid tumors in order to activate T cells and NK cells. We show that NK cells alone, i.e., without T cells, can eradicate large solid tumors when they are activated by IL15 presented by IL15Rα in the tumor rim.

The developments disclosed herein include the discovery that a mutant chaperone, Cosmc, converts a wild-type protein into a truly tumor-specific Tn-O-glycopeptide antigen on a murine tumor. Cosmc mutations are found in other spontaneous tumors, not only from mice but also humans (leukemia and solid cancers). Other mechanisms also frequently cause Tn-glycopeptide epitopes that are recognized by the 5E5 or 3H4 monoclonal antibodies on common human cancers.

Important to the anti-cancer effects of the gene products encoded by the polynucleotides of the disclosure is the ability of the encoded bivalent binding proteins to specifically bind to cancer-specific epitopes, such as the Tn-O-glycopeptide epitopes detectably unique to cancer cells. Facilitating presentation of Tn-O-glycopeptide epitopes on cancer cells are mutant Cosmc (core 1 β3-Gal-T-specific molecular chaperone), a chaperone protein required for core 1 β3-galactosyltransferase (C1β3Gal-T) activity. C1β3Gal-T catalyzes formation of the T antigen (core 1 O-glycan Galβ1-3GalNAcα1-Ser/Thr). Cosmc mutations, however, are only one of several mechanisms causing the frequent appearance of Tn-O-glycopeptide epitopes on human cancers (FIG. 1). The disclosure provides compositions that bind specifically to Tn-O-glycopeptide epitopes unique to cancer cells, including but not limited to cancer cells lacking wild-type Cosmc function. Such cancer-specific epitopes have been found on the human protein MUC1 and are expected to exist on homologous proteins in other vertebrate cells, including mammalian cells like mouse cells.

As noted above, the chaperone, Cosmc (Core1 β1,3-galactosyl-transferase-specific molecular chaperone), is essential for the function of the Core1 β1,3-galactosyl-transferase (C1GalT or T-synthase) (FIG. 1)(32). Mutations in Cosmc are also found in other spontaneous tumors in mice (16) and humans (leukemia and solid tumors) (17) and in premalignant crypts in ulcerative colitis patients (33). Thus, the inference is that defined, truly tumor-specific antigens are predictably found on at least the subgroup of common human cancers that lack Cosmc function due to mutations. While there is no reliable information on how frequently human tumors have mutational loss of Cosmc/C1GalT function, lower levels of Tn-O-glycopeptide antigens are frequently expressed in many common cancer cells due to impaired regulation of glycosylation pathways (FIG. 1). Therefore, other changes in cancer appear to "substitute" for a mutational loss of Cosmc. For example, the high affinity Tn-O-glycopeptide antibody 5E5 binds to over 80% of human breast cancers and over 85% of human ovarian cancers. Knocking out Cosmc from cancer cells strongly up-regulates the expression of Tn-O-glycopeptide epitopes. Furthermore, cancer cells lacking Cosmc are highly immunogenic and can elicit cancer-specific antibodies (16, 34). This observation led to the use of Cosmc gene-deleted cancer cells (SimpleCells) for immunization to induce monoclonal antibodies against Tn-O-glycopeptides that can be targeted by CARs. It is expected that antibodies identified by immunizing with Cosmc-negative cancer cells will also be useful for a majority of cancer cells that have other mechanisms of defective glycosylation leading to the expression of Tn. Certainly, the prototype epitope recognized by the 237 monoclonal is an exquisitely specific Tn-O-glycopeptide in position 77 of murine podoplanin/OTS8 (4, 16), but this epitope is always present in cancers if cancer cells are Tn-positive and express the specific protein providing the appropriate peptide sequence (e.g., murine OTS8/podoplanin).

The disclosure provides technology that incorporates recognition of, and binding to, highly specific Tn-O-glycopeptide epitopes. This includes, but is not restricted to, Tn-O-glycopeptide epitopes caused by Cosmc mutations that convert wild-type proteins in cancers to tumor-specific antigens, because Tn-O-glycopeptide epitopes are also found in common cancers lacking Cosmc mutations. It is expected that common solid cancers of diverse origin will share highly tumor-specific and molecularly predictable Tn-O-glycopeptide epitopes, which can be treated with CARs or fusion proteins specifically recognizing and binding to such epitopes.

The disclosure provides exquisitely cancer-as well as protein-specific antibody receptors incorporated into CARs as well as providing the binding specificity of fusion proteins. Tn alone is a poor target detected by IgM of low affinity, while Tn-glycopeptide epitopes are strong targets detected by high-affinity IgG antibodies. These IgG antibodies engulf the single sugar GalNAc and gain their affinity and specificity from "reading" the specific amino acid sequence of the protein surrounding the single sugar. Thus, Tn-O-glycopeptide epitopes can be targeted with exquisitely cancer—as well as protein-specific antibody receptors that can be used for making CARs as well as fusion proteins.

The various forms of bivalent binding proteins known in the art are contemplated by the disclosure. Exemplary bivalent binding proteins of the disclosure include chimeric antigen receptors (CARs), fusion proteins, including fusions comprising single-chain variable (antibody) fragment (scFv) multimers or scFv fusions to coding regions encoding products useful in treating cancer, e.g., IL-15, IL15Rα, or IL-15/IL15Rα constructs, diabodies, tribodies, tetrabodies, and bispecific bivalent scFvs, including bispecific tandem bivalent scFvs, also known as bispecific T cell engagers, or BiTEs. Any of these bivalent binding protein forms, moreover, may exhibit any of various relative structures, as it is known in the art that different domain orders (e.g., $H_2N$-VH-linker-VL-$CO_2H$ and $H_2N$-VL-linker-VH-$CO_2H$) are compatible with specific binding. Higher order forms of the bivalent binding proteins described herein are also contemplated, such as peptibodies comprising at least one form of the bivalent binding protein disclosed herein. The bivalent binding proteins of the disclosure specifically bind to a cancer-specific epitope (e.g., a glycopeptide) and the polynucleotides encoding them are codon-optimized, e.g., for maximal translation, for expression in the targeted cells (e.g., human or mouse cells). Codon optimization in the context of expressing the bivalent binding proteins of the disclosure, such as CARs, is important to ensuring that production of the protein is both efficient and robust enough to be useful as a source of therapeutic.

The disclosure also contemplates any one of these bivalent binding proteins linked to a peptide providing a second function such as a T cell signaling domain involved in T cell activation, a peptide that affects or modulates an immunological response to cancer cells, or an enzymatic component of a labeling system results in a CAR encoded by a polynucleotide according to the disclosure, if the coding region for the bivalent binding protein is codon-optimized for expression in a target cell.

In methods of preventing, treating or ameliorating a symptom of a cancer, the compositions of the disclosure are typically administered in the form of bivalent binding protein-transduced T cells, although administration of a vector comprising a polynucleotide of the disclosure or administration of a polynucleotide of the disclosure are also contemplated, depending on the functionalities of the bivalent binding protein. Combining a polynucleotide, vector or host cell of the disclosure with a physiologically suitable buffer, adjuvant or diluent yields a pharmaceutical composition according to the disclosure, and these pharmaceutical compositions are suitable for administration to diagnose, prevent, treat, or ameliorate a symptom of, a cancer.

CARs targeting Tn-O-glycopeptide epitopes on human cancers with normal or mutant Cosmc genes are also expected to yield additional antibodies. It is expected that Tn-O-glycopeptide epitopes are tumor-specific when detected on human cancers that have normal Cosmc function but aberrant glycosylation, as is frequently seen in common human cancers. All such antibodies, regardless of the engineered form (e.g., a CAR), are examined for toxicity to normal tissues using mice expressing the human target.

An anti-Tn glycopeptide CAR receptor has been constructed and inserted into a lentiviral vector for transduction into human T cells to be tested in vitro and in human xenograft mouse models, to confirm that the composition could be used to effectively treat common human cancers of the breast or ovary. Undiminished high expression levels of Tn-O-glycopeptide antigen were demonstrated in cancer cells isolated from repeated relapses in an ovarian cancer patient who does not have a Cosmc mutation, consistent with such mutations not being crucial for Tn expression.

A fusion protein composed of the scFv-receptor 237 for the Tn-O-glycopeptide epitope fused to IL15-IL15Rα also has been constructed. It is expected that the fusion protein will eliminate clinical size tumors or only incipient and microdisseminated cancer cells, that the microenvironment of established tumors prevents T cell activation by the fusion protein, and that the fusion protein causes the appearance of densely granulated NK cells in and around tumors and rescues tolerant tumor-infiltrating T cells.

Studies with newly generated tumor lines from IL-15Rα KO mice showed that this construct will likely be effective in treating or preventing human cancers, many of which may lack IL15Rα. A second monoclonal antibody has been made against a surface Tn-O-glycopeptide that is also expressed in several ovarian and other human cancers. Simultaneous targeting of independently expressed Tn-O-glycopeptides by CARs should reduce the chance of escape of a cancer subpopulation, which provides a strong reason for identifying additional Tn-O-glycopeptide targets.

The disclosure further contemplates the simultaneous targeting of two independent Tn-O-glycopeptide epitopes on a human cancer, which may be essential for preventing escape from CAR treatment, as noted above. Therefore, human cancer cells lacking Cosmc function will be used as highly effective inducers of Tn-O-glycopeptide-specific antibodies to select for Tn-O-glycopeptide epitopes on proteins of common human cancer cells.

The technology moves the field forward on three fronts by: (i) translating knowledge of how to destroy large, solid, non-hematopoietic tumors with TCR-transduced T cells to optimize the design and use of CAR-transduced T cells using the very same tumors, (ii) expanding the usage of Tn-O-glycopeptide antigens caused by Cosmc mutations to Tn-O-glycopeptide epitopes caused by other mechanisms and commonly observed in a variety of cancers, including breast, ovarian, colon and pancreatic cancers, and (iii) generating new antibodies (e.g., monoclonal antibodies) that recognize Tn-O-glycopeptide epitopes that are either Cosmc-mutation-dependent or caused by other mechanisms. For this effort, a panel of isogenic Cosmc-KO cell lines from common human cancers is used. These are highly immunogenic and are used for immunization, while techniques exploiting genetics, proteomics and glycomics are used for screening and analysis of the target structure as well as its genetic origin.

Consistent with the spirit of the foregoing, the following provides a description of the materials and methods provided herein.

In exemplary embodiments, the binding agent provided herein comprises a constant region of a heavy chain and/or a constant region of a light chain of an immunoglobulin. Sequences for heavy and light chain constant regions are publically available. For example, the National Center of Biotechnology Information (NCBI) nucleotide database provides a sequence of the constant region of the IgG1 kappa light chain. See GenBank Accession No. DQ381549.1, incorporated herein by reference. Also, the NCBI nucleotide database provides a sequence of the constant region of the *Mus musculus* IgG1. See GenBank Accession No. DQ381544.1.

In exemplary aspects, the Tn glycopeptide binding agent is an antibody, or an antigen-binding fragment thereof. In exemplary aspects, a linker comprising a short amino acid sequence of about 5 to about 25 amino acids, e.g., about 10 to about 20 amino acids, is provided. In exemplary aspects, the linker comprises the amino acid sequence of EEGEFSEAR (SEQ ID NO 25). In exemplary aspects, the linker comprises the amino acid sequence of AKTTPPKLEEGEFSEARV (SEQ ID NO: 26).

In exemplary aspects, the antibody can be any type of immunoglobulin that is known in the art. For instance, the antibody can be of any isotype, e.g., IgA, IgD, IgE, IgG, IgM. The antibody can be monoclonal or polyclonal. The antibody can be a naturally occurring antibody, i.e., an antibody isolated and/or purified from a mammal, e.g., mouse, rabbit, goat, horse, chicken, hamster, human, and the like. In this regard, the antibody may be considered to be a mammalian antibody, e.g., a mouse antibody, rabbit antibody, goat antibody, horse antibody, chicken antibody, hamster antibody, human antibody, and the like. The term "isolated" as used herein means having been removed from its natural environment. The term "purified," as used herein relates to the isolation of a molecule or compound in a form that is substantially free of contaminants normally associated with the molecule or compound in a native or natural environment and means having been increased in purity as a result of being separated from other components of the original composition. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In exemplary aspects, the antibody comprises a constant region of an IgG. In exemplary aspects, the antibody comprises a constant region of an $IgG_1$. In exemplary aspects, the antibody comprises a constant region of an IgG kappa light chain.

In exemplary aspects, the antibody comprises a constant region of a Mus musculus $IgG_1$.

The anti-Tn glycopeptide antibodies and fragments thereof of the disclosure can have any level of affinity or avidity for Tn glycopeptide. The dissociation constant ($K_D$) may be any of those exemplary dissociation constants described herein with regard to binding units. Binding constants, including dissociation constants, are determined by methods known in the art, including, for example, methods that utilize the principles of surface plasmon resonance, e.g., methods utilizing a Biacore™ system. In accordance with the foregoing, in some embodiments, the antibody is in monomeric form, while in other embodiments, the antibody is in polymeric form. In certain embodiments in which the antibody comprises two or more distinct antigen binding regions or fragments, the antibody is considered bispecific, trispecific, or multi-specific, or bivalent, trivalent, or multivalent, depending on the number of distinct epitopes that are recognized and bound by the binding agent.

In exemplary aspects, the $K_D$ of binding of Tn glycopeptide to a Tn glycopeptide binding agent is between about 0.0001 nM and about 100 nM. In some embodiments, the $K_D$ is at least or about 0.0001 nM, at least or about 0.001 nM, at least or about 0.01 nM, at least or about 0.1 nM, at least or about 1 nM, or at least or about 10 nM. In some embodiments, the $K_D$ is no more than or about 100 nM, no more than or about 75 nM, no more than or about 50 nM, or no more than or about 25 nM. In exemplary aspects, the antibody has a $K_D$ for human Tn glycopeptide that is no greater than about $1.39 \times 10^{-9}$ M.

In exemplary embodiments, the antibody is a genetically engineered antibody, e.g., a single chain antibody, a humanized antibody, a chimeric antibody, a CDR-grafted antibody, an antibody that includes portions of CDR sequences specific for Tn glycopeptide (e.g., an antibody that includes the six CDR sequences of an anti-Tn glycopeptide antibody, a humaneered or humanized antibody, a bispecific antibody, a trispecific antibody, and the like, as defined in greater detail herein. Genetic engineering techniques also provide the ability to make fully human antibodies in a non-human.

In some aspects, the antibody is a chimeric antibody. The term "chimeric antibody" is used herein to refer to an antibody containing constant domains from one species and the variable domains from a second, or more generally, containing stretches of amino acid sequence from at least two species.

In some aspects, the antibody is a humanized antibody. The term "humanized" when used in relation to antibodies, is used to refer to antibodies having at least CDR regions from a nonhuman source that are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence, as would be known in the art.

Use of the terms "chimeric or humanized" herein is not meant to be mutually exclusive; rather, is meant to encompass chimeric antibodies, humanized antibodies, and chimeric antibodies that have been further humanized. Except where context otherwise indicates, statements about (properties of, uses of, testing, and the like) chimeric antibodies apply to humanized antibodies, and statements about humanized antibodies pertain also to chimeric antibodies. Likewise, except where context dictates, such statements also should be understood to be applicable to antibodies and antigen binding fragments of such antibodies.

In some aspects of the disclosure, the binding agent is an antigen binding fragment of an antibody that specifically binds to an Tn glycopeptide in accordance with the disclosure. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like. Antibody fragments of the invention, however, are not limited to these exemplary types of antibody fragments.

In exemplary aspects, the Tn glycopeptide binding agent is an antigen binding fragment. In exemplary aspects, the antigen binding fragment is a single-chain antibody fragment such as an scFv. Such aspects embrace the further inclusion of a linker that comprises a short amino acid sequence of about 5 to about 25 amino acids, e.g., about 10 to about 20 amino acids. In exemplary aspects, the linker comprises the amino acid sequence of EEGEFSEAR (SEQ ID NO: 25). In exemplary aspects, the linker comprises the amino acid sequence of AKTTPPKLEEGEFSEARV (SEQ ID NO: 26).

In exemplary aspects, the antigen binding fragment comprises a leader sequence. Optionally, the leader sequence, in some aspects, is located N-terminal to the heavy chain variable region. In exemplary aspects, the antigen binding fragment comprises an Ig kappa leader sequence. Suitable leader sequences are known in the art, and include, for example, an Ig kappa leader sequence of METDTLLLWV-LLLWVPGSTGD (SEQ ID NO: 27).

In exemplary aspects, an antigen binding fragment comprises one more tag sequences. Tag sequences may assist in the production and characterization of the manufactured antigen binding fragment. In exemplary aspects, the antigen binding fragment comprises one or more tag sequences C-terminal to the light chain variable region. Suitable tag sequences are known in the art and include, but are not limited to, Myc tags, His tags, and the like. In exemplary aspects, an antigen binding fragment comprises a Myc tag of GGPEQKLISEEDLN (SEQ ID NO: 28). In exemplary aspects, an antigen binding fragment comprises a His tag sequence of HHHHHH (SEQ ID NO: 29).

In exemplary aspects, the antigen binding fragment of the disclosures comprises, from the N- to the C-terminus, a leader sequence, a heavy chain variable region, a linker sequence, a light chain variable region, a Myc tag (e.g., SEQ ID NO: 28), and a His tag (e.g., SEQ ID NO: 29).

In exemplary aspects, the antigen binding fragment is a domain antibody. A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth the weight of a full antibody. Domain antibodies may be derived from full antibodies, such as those described herein. The antigen binding fragments in some embodiments are monomeric or polymeric, bispecific or trispecific, and bivalent or trivalent.

Antibody fragments that contain the antigen binding, or idiotope, of the antibody molecule share a common idiotype and are contemplated by the disclosure. Such antibody fragments may be generated by techniques known in the art and include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent.

In exemplary aspects, the binding agent provided herein is a single-chain variable region fragment (scFv) antibody fragment. An scFv may consist of a truncated Fab fragment comprising the variable (V) domain of an antibody heavy chain linked to a V domain of an antibody light chain via a synthetic peptide, and it can be generated using routine recombinant DNA technology techniques (see, e.g., Janeway et al., Immunobiology, $2^{nd}$ Edition, Garland Publishing, New York, (1996)). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs of the disclosure, can also be engineered to assemble into stable multimeric oligomers of high binding avidity and specificity to different target antigens. Such diabodies (dimers), triabodies (trimers) or tetrabodies (tetramers) are well known in the art. See e.g., Kortt et al., Biomol Eng. 2001 18:95-108, (2001) and Todorovska et al., J Immunol Methods. 248:47-66, (2001).

In exemplary aspects, the binding agent is a bispecific antibody (bscAb). Bispecific antibodies are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNAs obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both of which are incorporated herein by reference in their entireties.

In exemplary aspects, the binding agent is a bispecific T-cell engaging antibody (BiTE) containing two scFvs produced as a single polypeptide chain. Methods of making and using BiTE antibodies are described in the art. See, e.g., Cioffi et al., Clin Cancer Res 18: 465, Brischwein et al., Mol Immunol 43:1129-43 (2006); Amann M et al., Cancer Res 68:143-51 (2008); Schlereth et al., Cancer Res 65: 2882-2889 (2005); and Schlereth et al., Cancer Immunol Immunother 55:785-796 (2006).

In exemplary aspects, the binding agent is a dual affinity re-targeting antibody (DART). DARTs are produced as separate polypeptides joined by a stabilizing interchain disulfide bond. Methods of making and using DART antibodies are described in the art. See, e.g., Rossi et al., MAbs 6: 381-91 (2014); Fournier and Schirrmacher, BioDrugs 27:35-53 (2013); Johnson et al., J Mol Biol 399:436-449 (2010); Brien et al., J Virol 87: 7747-7753 (2013); and Moore et al., Blood 117:4542 (2011).

In exemplary aspects, the binding agent is a tetravalent tandem diabody (TandAbs) in which an antibody fragment is produced as a non-covalent homodimer folder in a head-to-tail arrangement. TandAbs are known in the art. See, e.g., McAleese et al., Future Oncol 8: 687-695 (2012); Portner et al., Cancer Immunol Immunother 61:1869-1875 (2012); and Reusch et al., MAbs 6:728 (2014).

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, $5^{th}$ Ed., Garland Publishing, New York, N.Y. (2001)).

Monoclonal antibodies for use in the invention may be prepared using any technique that provides for the production of antibody molecules by continuous cell lines in culture. These include, but are not limited to, the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, a polyclonal antibody is prepared by immunizing an animal with an immunogen comprising a polypeptide of the present invention and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit, in some exemplary aspects, is a preferred choice for production of polyclonal antibodies. In an exemplary method for generating a polyclonal antisera immunoreactive with the chosen Tn glycopeptide epitope, 50 µg of Tn glycopeptide antigen is emulsified in Freund's Complete Adjuvant for immunization of rabbits. At intervals of, for example, 21 days, 50 µg of epitope are emulsified in Freund's Incomplete Adjuvant for boosts. Polyclonal antisera may be obtained, after allowing time for antibody generation, simply by bleeding the animal and preparing serum samples from the whole blood.

Briefly, to generate monoclonal antibodies, a mouse is injected periodically with recombinant Tn glycopeptide against which the antibody is to be raised (e.g., 10-20 µg Tn glycopeptide emulsified in Freund's Complete Adjuvant). The mouse is given a final pre-fusion boost of a Tn glycopeptide polypeptide containing the epitope that allows specific recognition of lymphatic endothelial cells in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1\times10^8$) are combined with $2.0\times10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5\times10^6$ splenocytes/ml and plated into 10 Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to Tn glycopeptide as follows. Immulon 4 plates (Dynatech, Cambridge, Mass.) are coated for 2 hours at 37° C. with 100 ng/well of Tn glycopeptide diluted in 25 mM Tris, pH 7.5. The coating solution is aspirated and 200 µl/well of blocking solution (0.5% fish skin gelatin (Sigma) diluted in CMF-PBS) is added and incubated for 30 minutes at 37° C. Plates are washed three times with PBS containing 0.05% Tween 20 (PBST) and 50 µl culture supernatant is added. After incubation at 37° C. for 30 minutes, and washing as above, 50 µl of horseradish peroxidase-conjugated goat anti-mouse IgG(Fc) (Jackson ImmunoResearch, West Grove, Pa.) diluted 1:3500 in PBST is added. Plates are incubated as above, washed four times with PBST, and 100 µl substrate, consisting of 1 mg/ml o-phenylene diamine (Sigma) and 0.1 µl/ml 30% $H_2O_2$ in 100 mM citrate, pH 4.5, are added. The color reaction is stopped after 5 minutes with the addition of 50 µl of 15% $H_2SO_4$. The $A_{490}$ absorbance is determined using a plate reader (Dynatech).

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media that support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and 5194/15XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be compositions of the disclosure.

Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) that are known in the art may be used. Further, methods of producing antibodies in non-human animals are described in, e.g., U.S. Pat. Nos. 5,545,806, 5,569,825, and 5,714,352, and U.S. Patent Application Publication No. 2002/0197266 A1), each incorporated herein by reference.

Antibodies may also be produced by inducing in vivo production in the lymphocyte population or by screening recombinant immunoglobulin libraries or panels of highly specific binding reagents as disclosed in Orlandi et al. (Proc. Natl. Acad. Sci. 86: 3833-3837; 1989), and Winter and Milstein (Nature 349: 293-299, 1991), each incorporated herein by reference.

Furthermore, phage display can be used to generate an antibody of the disclosure. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, $3^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403,484; 5,571,698; 5,837, 500; and 5,702,892. The techniques described in U.S. Pat. Nos. 5,780,279; 5,821,047; 5,824,520; 5,855,885; 5,858, 657; 5,871,907; 5,969,108; 6,057,098; and 6,225,447, are also contemplated as useful in preparing antibodies according to the disclosure.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539; 5,585,089; and 5,693,761; European Patent No. 0239400 B1; and United Kingdom Patent No. 2188638. Humanized antibodies can also be generated using the antibody resurfacing technology described in U.S. Pat. No. 5,639,641 and Pedersen et al., J. Mol. Biol., 235:959-973 (1994).

Techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81: 6851-6855, 1984; Neuberger et al., Nature 312: 604-608, 1984; and Takeda et al., Nature 314: 452-454; 1985). Alternatively, techniques described for the production of single-chain antibodies (U.S. Pat. No. 4,946,778) can be adapted to produce Tn glycopeptide-specific single chain antibodies.

A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693, 762). Generally, a humanized antibody has one or more amino acid residues introduced into a CDR region and/or into its framework region from a source which is non-human. Humanization can be performed, for example, using methods described in Jones et al. (*Nature* 321: 522-525, 1986), Riechmann et al., (*Nature*, 332: 323-327, 1988) and Verhoeyen et al. (*Science* 239:1534-1536, 1988), by substituting at least a portion of a rodent complementarity-determining region (CDR) for the corresponding region of a human antibody. Numerous techniques for preparing engineered antibodies are described, e.g., in Owens and Young, *J. Immunol. Meth.*, 168:149-165 (1994). Further changes can then be introduced into the antibody framework to modulate affinity or immunogenicity.

Consistent with the foregoing description, compositions comprising CDRs may be generated using, at least in part, techniques known in the art to isolate CDRs. Complementarity-determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions [Janeway et al., supra]. The murine CDRs also are found at approximately these amino acid residues. It is understood in the art that CDR regions may be found within several amino acids of the approximated amino acid positions set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. Polypeptide compositions comprising one, two, three, four, five and/or six complementarity-determining regions of an antibody are also contemplated. Using the conserved framework sequences surrounding the CDRs, PCR primers complementary to these consensus framework sequences are generated to amplify the CDR sequence located between the primer regions. Techniques for cloning and expressing nucleotide and polypeptide sequences are well-established in the art [see e.g., Sambrook et al., *Molecular Cloning: A Laboratory Manual*, $2^{nd}$ Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

It is contemplated that modified polypeptide compositions comprising one, two, three, four, five, or six CDRs of a heavy or light chain of an antibody according to the disclosure are generated, wherein a CDR is altered to provide increased specificity or affinity or avidity to the target Tn glycopeptide. Sites at locations in the CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site.

Framework regions (FR) of a murine antibody are humanized by substituting compatible human framework regions chosen from a large database of human antibody variable sequences, including over twelve hundred human $V_H$ sequences and over one thousand $V_L$ sequences. The database of antibody sequences used for comparison is downloaded from Andrew C. R. Martin's KabatMan web page (http://www.rubic.rdg.ac.uk/abs/). The Kabat method for identifying CDRs provides a means for delineating the approximate CDR and framework regions of any human antibody and comparing the sequence of a murine antibody for similarity to determine the CDRs and FRs. Best matched human $V_H$ and $V_L$ sequences are chosen on the basis of high overall framework matching, similar CDR length, and minimal mismatching of canonical and $V_H/V_L$ contact residues. Human framework regions most similar to the murine sequence are inserted between the murine CDRs. Alternatively, the murine framework region may be modified by making amino acid substitutions of all or part of the native framework region that more closely resemble a framework region of a human antibody.

"Conservative" amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). "Insertions" or "deletions" are preferably in the range of about 1 to 20 amino acids, more preferably 1 to 10 amino acids. The variation may be introduced by systematically making substitutions of amino acids in a polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for expressing polypeptide compositions useful in the invention are described in greater detail below.

Additionally, another useful technique for generating antibodies for use in the methods of the disclosure may be one which uses a rational design-type approach. The goal of rational design is to produce structural analogs of biologically active polypeptides or compounds with which they interact (agonists, antagonists, inhibitors, peptidomimetics, binding partners, and the like). By creating such analogs, it is possible to fashion additional antibodies that are more immunoreactive than the native or natural molecule. In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout a molecule with alanine, and the resulting effect on function is determined.

It also is possible to solve the crystal structure of the specific antibodies. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype antibody is expected to be an analog of the original antigen. The anti-idiotype antibody is then be used to identify and isolate additional antibodies from banks of chemically- or biologically-produced peptides.

Chemically synthesized bispecific antibodies may be prepared by chemically cross-linking heterologous Fab or $F(ab')_2$ fragments by means of chemicals such as heterobifunctional reagent succinimidyl-3-(2-pyridyldithiol)-propionate (SPDP, Pierce Chemicals, Rockford, Ill.). The Fab and $F(ab')_2$ fragments can be obtained from intact antibody by digesting it with papain or pepsin, respectively (Karpovsky et al., J. Exp. Med. 160:1686-701, 1984; Titus et al., J. Immunol., 138:4018-22, 1987).

Methods of testing antibodies for the ability to bind to the epitope of the Tn glycopeptide, regardless of how the antibodies are produced, are known in the art and include any antibody-antigen binding assay such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Selection of antibodies from an antibody population for purposes herein also include using blood vessel endothelial cells to "subtract" those antibodies that cross-react with epitopes on such cells other than Tn glycopeptide epitopes. The remaining antibody population is enriched in antibodies preferential for Tn glycopeptide epitopes.

Aptamers

Recent advances in the field of combinatorial sciences have identified short polymer sequences (e.g., oligonucleic acid or peptide molecules) with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds, and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of aptamers, which often utilize hairpin loops created from short regions without complementary base pairing, naturally derived antibodies that utilize combinatorial arrangement of looped hypervariable regions and new phage-display libraries utilizing cyclic peptides that have shown improved results when compared to linear peptide phage display results. Thus, sufficient evidence has been generated to indicate that high affinity ligands can be created and identified by combinatorial molecular evolution techniques. For the present disclosure, molecular evolution techniques can be used to isolate binding agents specific for a Tn glycopeptide disclosed herein. For more on aptamers, see generally, Gold, L., Singer, B., He, Y. Y., Brody. E., "Aptamers As Therapeutic And Diagnostic Agents," J. Biotechnol. 74:5-13 (2000). Relevant techniques for generating aptamers are found in U.S. Pat. No. 6,699,843, which is incorporated herein by reference in its entirety.

In some embodiments, the aptamer is generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is identified. Nucleic acids may be screened to select for molecules that bind to more than one target. Binding more than one target can refer to binding more than one simultaneously or competitively. In some embodiments, a binding agent comprises at least one aptamer, wherein a first binding unit binds a first epitope of an Tn glycopeptide and a second binding unit binds a second epitope of the Tn glycopeptide.

As used herein, the term "reduce" as well as like terms, e.g., "inhibit," do not necessarily imply 100% or a complete reduction or inhibition. Rather, there are varying degrees of reduction or inhibition of which one of ordinary skill in the art recognizes as having a potential benefit or therapeutic effect Chimeric Antigen Receptors (CARs)

In exemplary aspects, the effector domain is a T-cell signaling domain. In exemplary aspects, the conjugate is a chimeric antigen receptor (CAR). Chimeric antigen receptors (CARs) are engineered transmembrane proteins that combine the specificity of an antigen-specific antibody with a T-cell receptor's function. In general, CARs comprise an ectodomain, a transmembrane domain, and an endodomain. The ectodomain of a CAR in exemplary aspects comprises an antigen recognition region, which may be an scFV of an antigen-specific antibody. The ectodomain also in some embodiments comprises a signal peptide which directs the nascent protein into the endoplasmic reticulum. In exemplary aspects, the ectodomain comprises a spacer which links the antigen recognition region to the transmembrane domain. The transmembrane (TM) domain is the portion of the CAR which traverses the cell membrane. In exemplary aspects, the TM domain comprises a hydrophobic alpha helix. In exemplary aspects, the TM domain comprises all or a portion of the TM domain of CD28. In exemplary aspects, the TM domain comprises all or a portion of the TM domain of CD8α. The endodomain of a CAR comprises one or more signaling domains. In exemplary aspects, the endodomain comprises the zeta chain of CD3, which comprises three copies of the Immunoreceptor Tyrosine-based Activation Motif (ITAM). An ITAM generally comprises a Tyr residue separated by two amino acids from a Leu or Ile. In the case of immune cell receptors, e.g., the T cell receptor and the B cell receptor, the ITAMs occur in multiples (at least two) and each ITAM is separated from another by 6-8 amino acids. The endodomain of CARs may also comprises additional signaling domains, e.g., portions of proteins that are important for downstream signal transduction. In exemplary aspects, the endodomain comprises signaling domains from one or more of CD28, 41BB or 4-1BB (CD137), ICOS, CD27, CD40, OX40 (CD134), or Myd88. Methods of making CARs, expressing them in cells, e.g., T-cells, and utilizing the CAR-expressing T-cells in therapy, are known in the art. See, e.g., International Patent Application Publication Nos. WO2014/208760, WO2014/190273, WO2014/186469, WO2014/184143, WO2014180306, WO2014/179759, WO2014/153270, U.S. Application Publication Nos. US20140369977, US20140322212, US20140322275, US20140322183, US20140301993, US20140286973, US20140271582, US20140271635, US20140274909, European Application Publication No. 2814846, each of which are incorporated by reference in their entirety.

In exemplary aspects, the conjugate of the disclosure is a Tn glycopeptide-specific chimeric antigen receptor (CAR) comprising a Tn glycopeptide binding agent described herein, a hinge region, and an endodomain comprising a signaling domain of a CD3 zeta chain and a signaling domain of CD28, CD134, and/or CD137. In exemplary aspects, the CAR further comprises a transmembrane (TM) domain based on the TM domain of CD28. In exemplary aspects, the CAR further comprises a transmembrane (TM) domain based on the TM domain of CD8α.

In exemplary aspects, the endodomain further comprises a signaling domain of one or more of: CD137, CD134, CD27, CD40, ICOS, and Myd88. For example, the disclosure contemplates a sequence comprising a CD27 signaling domain, a sequence comprising a CD40 signaling domain, a sequence comprising a CD134 signaling domain, a sequence comprising a CD137 signaling domain, a sequence comprising an ICOS signaling domain, and/or a sequence comprising a Myd88 signaling domain, respectively.

In exemplary aspects, the CAR comprises (A) a Tn glycopeptide binding agent sequence, (B) a hinge region; (C) an endodomain comprising a signaling domain of a CD3 zeta chain and a signaling domain of CD28 and at least one other signaling domain. In exemplary aspects, the CAR comprises an endodomain comprising a signaling domain of 41BB (CD137). In exemplary aspects, the CD137 signaling is N-terminal to a CD3 zeta chain signaling chain.

In exemplary aspects, the CAR comprises an endodomain comprising a signaling domain of OX40 (CD134). In exemplary aspects, the CD137 signaling is N-terminal to a CD3 zeta chain signaling chain.

In exemplary aspects, the CAR comprises (A) a Tn glycopeptide binding agent sequence, (B) a hinge region; (C) a transmembrane domain of CD8α chain, and (D) an endodomain comprising a signaling domain of a CD3 zeta chain, and, optionally, at least one other signaling domain. In exemplary aspects, the CAR further comprises a CD137 signaling domain and a CD3 zeta chain signaling domain.

Nucleic Acids, Vectors, Host Cells

Further provided by the disclosures is a nucleic acid comprising a nucleotide sequence encoding any of the binding agents and conjugates (e.g., chimeric proteins, fusion proteins, CARs) described herein. The nucleic acid may comprise any nucleotide sequence which encodes any of the binding agents or conjugates described herein.

By "nucleic acid" as used herein includes "polynucleotide," "oligonucleotide," and "nucleic acid molecule," and generally means a polymer of DNA or RNA, which may be single-stranded or double-stranded, synthesized or obtained (e.g., isolated and/or purified) from natural sources, which may contain natural, non-natural or altered nucleotides, and which may contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In exemplary aspects, the nucleic acids of the disclosures are recombinant. As used herein, the term "recombinant" refers to (i) molecules that are constructed outside living cells by joining natural or synthetic nucleic acid segments to nucleic acid molecules that may replicate in a living cell, or (ii) molecules that result from the replication of those described in (i) above. For purposes herein, the replication may be in vitro replication or in vivo replication.

The nucleic acids in exemplary aspects are constructed based on chemical synthesis and/or enzymatic ligation reactions using procedures known in the art. See, for example, Sambrook et al., supra, and Ausubel et al., supra. For example, a nucleic acid may be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that may be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the disclosures may be purchased from companies, such as Macromolecular Resources (Fort Collins, Colo.) and Synthegen (Houston, Tex.).

The nucleic acids of the disclosures in exemplary aspects are incorporated into a recombinant expression vector. In this regard, the disclosures provides recombinant expression vectors comprising any of the nucleic acids of the disclosures. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the disclosures are not naturally occurring as a whole. Parts of the vectors, however, may be naturally occurring. The recombinant expression vectors of the disclosure may comprise any type of nucleotides, including, but not limited to DNA and RNA, which may be single-stranded or double-stranded, synthesized or obtained in part from natural sources, and which may contain natural, non-natural or altered nucleotides. The recombinant expression vectors may comprise naturally occurring or non-naturally occurring internucleotide linkages, or both types of linkages. In exemplary aspects, the altered nucleotides or non-naturally occurring internucleotide linkages do not hinder the transcription or replication of the vector.

The recombinant expression vector of the disclosure may be any suitable recombinant expression vector, and may be used to transform or transfect any suitable host. Suitable vectors include those designed for propagation and expansion or for expression or both, such as plasmids and viruses. The vector may be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT1 1, λZapII (Stratagene), λEMBL4, and λNM1 149, also may be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector.

The recombinant expression vectors of the disclosures may be prepared using standard recombinant DNA techniques described in, for example, Sambrook et al., supra, and Ausubel et al., supra. Constructs of expression vectors, which are circular or linear, may be prepared to contain a replication system functional in a prokaryotic or eukaryotic host cell. Replication systems may be derived, e.g., from ColEl, 2μ plasmid, λ, SV40, bovine papilloma virus, and the like.

In exemplary aspects, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector may include one or more marker coding regions, which allow for selection of transformed or transfected hosts. Marker coding regions include biocide resistance, e.g., resistance to antibiotics, heavy metals, and the like, complementation in an auxotrophic host to provide prototrophy, and the like. Suitable marker coding regions for the expression vectors of the disclosure include, for instance, neomycin/G418 resistance coding regions, hygromycin resistance coding regions, histidinol resistance coding regions, tetracycline resistance coding regions, and ampicillin resistance coding regions.

The recombinant expression vector may comprise a native or normative promoter operably linked to the nucleotide sequence encoding the binding agent or conjugate or to the nucleotide sequence which is complementary to or which hybridizes to the nucleotide sequence encoding the binding agent or conjugate. The selection of promoters, e.g., strong, weak, inducible, tissue-specific and developmental-specific, is within the ordinary skill of the artisan.

Similarly, the combining of a nucleotide sequence with a promoter is also within the skill of the artisan. The promoter may be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors may be designed for either transient expression, for stable expression, or for both. Also, the recombinant expression vectors may be made for constitutive expression or for inducible expression. Further, the recombinant expression vectors may be made to include a suicide gene or coding region.

As used herein, the term "suicide gene" refers to a gene that causes the cell expressing the suicide gene to die. The suicide gene may be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Maycer Research UK Centre for Maycer Therapeutics at the Institute of Maycer Research, Sutton, Surrey, UK), Humana Press, 2004) and include, for example, the Herpes Simplex Virus (HSV) thymidine kinase (TK) gene, cytosine deaminase, purine nucleoside phosphorylase, and nitroreductase. The description of the characteristics, properties, and behavior of suicide genes also applies to the use of suicide coding regions.

The disclosures further provides a host cell comprising any of the nucleic acids or vectors described herein. As used herein, the term "host cell" refers to any type of cell that may contain the nucleic acid or vector described herein. In exemplary aspects, the host cell is a eukaryotic cell, e.g., plant, animal, fungi, or algae, or may be a prokaryotic cell, e.g., bacterium or protozoan. In exemplary aspects, the host cell is a cell originating or obtained from a subject, as described herein. In exemplary aspects, the host cell originates from or is obtained from a mammal. As used herein, the term "mammal" refers to any mammal, including, but not limited to, mammals of the order Rodentia, such as mice and hamsters, and mammals of the order Lagomorpha, such as rabbits. The mammals may be from the order Carnivora, including Felines (cats) and Canines (dogs). Alternatively, the mammals are from the order Artiodactyla, including bovine (cow) and swine (pig) or of the order Perssodactyla, including equine (horse). Other alternatives include mammals of the order Primates, Ceboids, or Simoids (monkeys) or of the order Anthropoids (humans and apes). An especially preferred mammal is the human.

In exemplary aspects, the host cell is a cultured cell or a primary cell, such as a cell isolated directly from an organism, e.g., a human. The host cell in exemplary aspects is an adherent cell or a suspended cell, i.e., a cell that grows in suspension. Suitable host cells are known in the art and include, for instance, DH5α E. coli cells, Chinese hamster ovarian (CHO) cells, monkey VERO cells, T293 cells, COS cells, HEK293 cells, and the like. For purposes of amplifying or replicating the recombinant expression vector, the host cell is preferably a prokaryotic cell, e.g., a DH5α cell. For purposes of producing a binding agent or a conjugate, the host cell is in some aspects a mammalian cell. In exemplary aspects, the host cell is a human cell. While the host cell may be of any cell type, the host cell may originate from any type of tissue, and may be of any developmental stage. In exemplary aspects, the host cell is a hematopoietic stem cell or progenitor cell. See, e.g., Nakamura De Oliveira et al., *Human Gene Therapy* 24:824-839 (2013). The host cell in exemplary aspects is a peripheral blood lymphocyte (PBL). In exemplary aspects, the host cell is a natural killer cell. In exemplary aspects, the host cell is a T cell.

For purposes herein, the T cell may be any T cell, such as a cultured T cell, e.g., a primary T cell, or a T cell from a cultured T cell line, e.g., Jurkat, SupT1, or a T cell obtained from a mammal. If obtained from a mammal, the T cell may be obtained from numerous sources, including but not limited to blood, bone marrow, lymph node, the thymus, or other tissues or fluids. T cells may also be enriched for or purified. The T cell may be obtained by maturing hematopoietic stem cells, either in vitro or in vivo, into T cells. In exemplary aspects, the T cell is a human T cell. In exemplary aspects, the T cell is a T cell isolated from a human. The T cell may be any type of T cell or a NK cell, and may be of any developmental stage, including but not limited to, CD4+/CD8+ double positive T or NK cells, CDA+ helper T cells, e.g., Th1 and Th2 cells, CD8+ T cells (e.g., cytotoxic T cells), peripheral blood mononuclear cells (PBMCs), peripheral blood leukocytes (PBLs), tumor infiltrating cells (TILs), memory T cells, naive T cells, and the like. Preferably, the T or NK cell is a CD8+ T cell or a CD4+ T cell.

Also provided by the disclosures is a population of cells comprising at least one host cell described herein. The population of cells may be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, and the like. Alternatively, the population of cells may be a substantially homogeneous population, in which the population comprises mainly host cells comprising the recombinant expression vector. The population also may be a clonal population of cells, in which all cells of the population are clones of a single host cell comprising a recombinant expression vector, such that all cells of the population comprise the recombinant expression vector. In exemplary embodiments of the disclosures, the population of cells is a clonal population comprising host cells expressing a nucleic acid or a vector described herein.

Pharmaceutical Compositions and Routes of Administration

In some embodiments of the disclosure, the binding agents, conjugates, nucleic acids, vectors, host cells, or populations of cells, are admixed with a pharmaceutically acceptable carrier. Accordingly, pharmaceutical compositions comprising any of the binding agents, conjugates, nucleic acids, vectors, host cells, or populations of cells described herein and comprising a pharmaceutically acceptable carrier, diluent, or excipient are contemplated.

The pharmaceutically acceptable carrier is any of those conventionally used and is limited only by physico-chemical considerations, such as solubility and lack of reactivity with the active binding agent(s), and by the route of administration. The pharmaceutically acceptable carriers described herein, for example, vehicles, adjuvants, excipients, and diluents, are well-known to those skilled in the art and are readily available to the public. In one aspect the pharmaceutically acceptable carrier is one that is chemically inert to the active ingredient(s) of the pharmaceutical composition, e.g., the first binding agent and the second binding agent, and one which has no detrimental side effects or toxicity under the conditions of use. The carrier in some embodiments does not produce adverse, allergic, or other untoward reactions when administered to an animal or a human. The pharmaceutical composition in some aspects is free of pyrogens, as well as other impurities that could be harmful to humans or animals. Pharmaceutically acceptable carriers include any and all solvents, dispersion media, coatings, antibacterial and antifungal agents, isotonic and absorption delaying agents and the like; the use of which are well known in the art.

Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Therapeutic formulations of the compositions useful for practicing the methods disclosed herein, such as polypeptides, polynucleotides, or binding agents such as antibodies, CARs, BiTEs and the like, may be prepared for storage by mixing the selected composition having the desired degree of purity with optional physiologically and pharmaceutically acceptable carriers, excipients, or stabilizers (Remington's Pharmaceutical Sciences, 18th edition, A. R. Gennaro, ed., Mack Publishing Company (1990)) in the form of a lyophilized cake or an aqueous solution. Pharmaceutical compositions may be produced by admixing with one or more suitable carriers or adjuvants such as water, mineral oil, polyethylene glycol, starch, talcum, lactose, thickeners, stabilizers, suspending agents, and the like. Such compositions may be in the form of solutions, suspensions, tablets, capsules, creams, salves, ointments, or other conventional forms.

Non-living compositions of the disclosure to be used for in vivo administration should be sterile. This is readily accomplished by filtration through sterile filtration membranes, prior to or following lyophilization and reconstitution. Such therapeutic compositions generally are placed into a container having a sterile access port, for example, an intravenous solution bag or vial having a stopper pierceable by a hypodermic injection needle. The pharmaceutical forms suitable for injectable use include sterile aqueous solutions or dispersions and sterile powders for the extemporaneous preparation of sterile injectable solutions or dispersions. In some cases the form should be sterile and should be fluid to the extent that easy syringability exists. It should be stable under the conditions of manufacture and storage and should be preserved against the contaminating action of microorganisms, such as bacteria and fungi. The composition for parenteral administration ordinarily will be stored in lyophilized form or in solution. For living compositions according to the disclosure, such as CARs expressed in a host cell such as a T cell, the above-described technologies are adapted to the characteristics of a living therapeutic. For example, sterilization would not be relevant and the use of techniques to preserve compositions against microorganisms would be adjusted or avoided.

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the inclusion in the compositions of agents delaying absorption, for example, aluminum monostearate and gelatin.

The choice of carrier will be determined in part by the particular type of binding agents of the pharmaceutical composition, as well as by the particular route used to administer the pharmaceutical composition. Accordingly, there are a variety of suitable formulations of the pharmaceutical composition.

The pharmaceutical composition of the present disclosures can comprise any pharmaceutically acceptable ingredient including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution-enhancing agents, dyes, emollients, emulsifying agents, emulsion stabilizers, fillers, film-forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiologically compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, and others known in the art.

In some embodiments, the pharmaceutical composition comprising the binding agents described herein is formulated for parenteral administration, subcutaneous administration, intravenous administration, intramuscular administration, intraarterial administration, intrathecal administration, or intraperitoneal administration. In other embodiments, the pharmaceutical composition is administered via nasal, spray, oral, aerosol, rectal, or vaginal administration. The compositions may be administered by infusion, bolus injection or by implantation device.

The following discussion on routes of administration is merely provided to illustrate exemplary embodiments and should not be construed as limiting the scope of the disclosed subject matter.

Formulations suitable for oral administration can consist of (a) liquid solutions, such as an effective amount of the composition of the disclosure dissolved in diluents, such as water, saline, a beverage such as coffee, tea, milk, soda, or fruit juice, a biocompatible buffer; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid or other excipients, as well as colorants, diluents, buffering agents, disintegrating agents, moistening agents, preservatives, flavoring agents, and other pharmacologically compatible excipients. Lozenge forms can comprise a composition of the disclosure in a flavor, usually sucrose and acacia or tragacanth, as well as pastilles comprising a composition of the disclosure in an inert base, such as gelatin and glycerin, or sucrose and acacia, emulsions, gels, and the like, optionally also containing such excipients as are known in the art.

The compositions of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressurized preparations, such as in a nebulizer or an atomizer. Such spray formulations also may be used to spray mucosa. In some embodiments, the composition is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Topical formulations are well-known to those of skill in the art. Such formulations are particularly suitable in the context of the disclosure for application to the skin.

In some embodiments, the pharmaceutical composition described herein is formulated for parenteral administration. For purposes herein, parenteral administration includes, but is not limited to, intravenous, intraarterial, intramuscular, intracerebral, intracerebroventricular, intracardiac, subcutaneous, intraosseous, intradermal, intrathecal, intraperitoneal, retrobulbar, intrapulmonary, intravesical, and intracavernosal injections or infusions. Administration by surgical implantation at a particular site is contemplated as well.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous delivery. The composition of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,5,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, a suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

The parenteral formulations in some embodiments contain preservatives or buffers. In order to minimize or eliminate irritation at the site of injection, such compositions optionally contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example water, immediately prior to use. Extemporaneous injection solutions and suspensions can be prepared from sterile powders, granules, and tablets of the kind previously described and known in the art.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

It will be appreciated by one of skill in the art that, in addition to the above-described pharmaceutical compositions, the composition of the disclosure can be formulated as inclusion complexes, such as cyclodextrin inclusion complexes, or liposomes.

Dose

For purposes herein, the amount or dose of the pharmaceutical composition administered is sufficient to effect, e.g., a therapeutic or prophylactic response or symptom amelioration, in the subject or animal, over a reasonable time frame. For example, the dose of the pharmaceutical composition is sufficient to treat or prevent a disease or medical condition in a period of from about 12 hours, about 18 hours, about 1 to 4 days or longer, e.g., 5 days, 6 days, 1 week, 10 days, 2 weeks, 16 to 20 days, or more, from the time of administration. In certain embodiments, the time period is even longer. The dose is determined by the efficacy and toxicity of the particular pharmaceutical composition and the condition of the animal (e.g., human), as well as the body weight of the animal (e.g., human) to be treated.

The dose of the pharmaceutical composition also will be determined by toxicity, as shown by the existence, nature and extent of any adverse side effects that might accompany the administration of a particular pharmaceutical composition. Typically, the attending physician will decide the dosage of the pharmaceutical composition with which to treat each individual patient, taking into consideration a variety of factors, such as age, body weight, general health, diet, sex, binding agents of the pharmaceutical composition to be administered, route of administration, and the severity of the condition being treated.

By way of example, the dose of the binding agent can be about 0.0001 to about 1 g/kg body weight of the subject being treated/day, from about 0.0001 to about 0.001 g/kg body weight/day, or about 0.01 mg to about 1 g/kg body weight/day. The pharmaceutical composition in some aspects comprises the binding agent at a concentration of at least A, wherein A is about 0.001 mg/ml, about 0.01 mg/ml, about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the binding agent at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an analog at a concentration range of A to B mg/ml, for example, about 0.001 to about 30.0 mg/ml.

Additional dosing guidance can be gauged from other antibody therapeutics, such as bevacizumab (Avastin™ Genentech); Cetuximab (Exbitux™ Imclone), Panitumumab (Vectibix™ Amgen), and Trastuzumab (Herceptin™ Genentech).

Timing of Administration

The disclosed pharmaceutical formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data, and initially gauged based on timing used for other antibody therapeutics.

Controlled Release Formulations

The pharmaceutical composition is in certain aspects modified into a depot form, such that the manner in which the active ingredients of the pharmaceutical composition (e.g., a binding agent) is released into the body to which it is administered is controlled with respect to time and location within the body (see, for example, U.S. Pat. No. 4,450,150). Depot forms in various aspects include, for example, an implantable composition comprising a porous or non-porous material, such as a polymer, wherein the binding agents are encapsulated by, or diffused throughout, the material and/or degradation of the non-porous material. The depot is then implanted into the desired location within the body and the binding agent is released from the implant at a predetermined rate.

Accordingly, the pharmaceutical composition in certain aspects is modified to have any type of in vivo release profile. In some aspects, the pharmaceutical composition is an immediate release, controlled release, sustained release, extended release, delayed release, or bi-phasic release formulation. Methods of formulating peptides (e.g., peptide binding agents) for controlled release are known in the art. See, for example, Qian et al., *J Pharm* 374: 46-52 (2009) and International Patent Application Publication Nos. WO 2008/130158, WO2004/033036; WO2000/032218; and WO 1999/040942. Suitable examples of sustained-release preparations include semi-permeable polymer matrices in the form of shaped articles, e.g., films, or microcapsules. Sustained-release matrices include polyesters, hydrogels, polylactides (U.S. Pat. No. 3,773,919, EP 58,481), copolymers of L-glutamic acid and gamma ethyl-L-glutamate (Sidman, et al., Biopolymers, 22: 547-556 (1983)), poly (2-hydroxyethyl-methacrylate) (Langer, et al., J. Biomed. Mater. Res., 15:167-277 (1981) and Langer, Chem. Tech., 12:98-105 (1982)), ethylene vinyl acetate (Langer, et al, supra) or poly-D(−)-3-hydroxybutyric acid (EP 133,988). Sustained-release compositions also may include liposomes, which can be prepared by any of several methods known in the art (e.g., DE 3,218,121; Epstein, et al., Proc. Natl.

Combinations

The compositions of the disclosures may be employed alone, or in combination with other agents. In some embodiments, more than one type of binding agent is administered. For example, the administered composition, e.g., pharmaceutical composition, may comprise an antibody as well as an scFv. In some embodiments, the compositions of the disclosure are administered together with another therapeutic agent or diagnostic agent, including any of those described herein. Certain diseases, e.g., cancers, or patients may lend themselves to a treatment of combined agents to achieve an additive or even a synergistic effect compared to the use of any one therapy alone.

Uses

Based in part on the data provided herein, the binding agents, conjugates, host cells, populations of cells, and pharmaceutical compositions are useful for treating a neoplasm, tumor, or a cancer.

For purposes of the present disclosure, the term "treat" and "prevent" as well as words stemming therefrom, as used herein, do not necessarily imply 100% or complete treatment (e.g., cure) or prevention. Rather, there are varying degrees of treatment or prevention that one of ordinary skill in the art recognizes as having a benefit or therapeutic effect. In this respect, the methods of the present disclosures can provide any amount or any level of treatment or prevention of a cancer in a patient, e.g., a human. Furthermore, the treatment or prevention provided by the method disclosed herein can include treatment or prevention of one or more conditions or symptoms of the disease, e.g., cancer, being treated or prevented. Also, for purposes herein, "prevention" can encompass delaying the onset of the disease, or a symptom or condition thereof.

The materials and methods described herein are especially useful for inhibiting neoplastic cell growth or spread; particularly neoplastic cell growth for which the Tn glycopeptide targeted by a binding agent of the disclosure plays a role.

Neoplasms treatable by the binding agents, conjugates, host cells, populations of cells, and pharmaceutical compositions of the disclosures include solid tumors, for example, carcinomas and sarcomas. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, and variously localized cancers and variations are contemplated targets. Cancers are grouped by embryonic origin (e.g., carcinoma, lymphomas, and sarcomas), by organ or physiological system, or by miscellaneous grouping. Particular cancers may overlap in their classification, and their listing in one group does not exclude them from another.

Carcinomas that may be targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocellular, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibrosum, follicular cancer of thyroid gland, gastric, gelatinoform, gelatinous, giant cell, giant cell cancer of thyroid gland, cancer gigantocellulare, glandular, granulose cell, hepatocellular, Hurthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, cancer molle, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's disease of the bone or breast, papillary, papillary cancer of thyroid gland, periampullary, preinvasive, prickle cell, primary intraosseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, Kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-Kaposi, reticulum cell, reticulum cell sarcoma of the brain, rhabdomyosarcoma, Rous, soft tissue, spindle cell, synovial, telangiectatic, sarcoma (osteosarcoma)/malignant fibrous histiocytoma of bone, and soft tissue sarcomas.

Lymphomas that may targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large non-cleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small non-cleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity-based), thymic lymphoma, and cutaneous T cell lymphomas.

Leukemias and other blood cell malignancies that may be targeted include acute lymphoblastic, acute myeloid, lymphocytic, chronic myelogenous, hairy cell, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, prolymphocytic, micromyeloblastic, megakaryoblastic, megakaryoctytic, Rieder cell, bovine, aleukemic, mast cell, myelocytic, plasma cell, subleukemic, multiple myeloma, nonlymphocytic, and chronic myelocytic leukemias.

Brain and central nervous system (CNS) cancers and tumors that may be targeted include astrocytomas (including cerebellar and cerebral), gliomas (including malignant gliomas, glioblastomas, brain stem gliomas, visual pathway and hypothalamic gliomas), brain tumors, ependymoma, medulloblastoma, supratentorial primitive neuroectodermal tumors, primary central nervous system lymphoma, extracranial germ cell tumor, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, and metastatic tumor cell invasion in the central nervous system.

Gastrointestinal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia. A discussion of colorectal cancer is described in Barderas et al., *Cancer Research* 72: 2780-2790 (2012).

Bone cancers that may be targeted include osteosarcoma and malignant fibrous histiocytomas, bone marrow cancers, bone metastases, osteosarcoma/malignant fibrous histiocytoma of bone, and osteomas and osteosarcomas. Breast cancers that may be targeted include small cell carcinoma and ductal carcinoma.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis, and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer a deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchial) Castleman's disease chronic myeloproliferative disorders, clear cell sarcoma of tendon sheaths, Ewing's family of tumors, head and neck cancer, lip and oral cavity cancer, Waldenstrom's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, Sezary syndrome, supratentorial primitive neuroectodermal tumors, unknown primary site, peritoneal effusion, malignant pleural effusion, trophoblastic neoplasms, and hemangiopericytoma.

In exemplary aspects, the cancer is any one of the foregoing cancers in which Tn glycopeptide is expressed on the cells of the cancer. In exemplary aspects, the method of treating cancer in a subject in need thereof comprises administering to the subject any of the binding agents, conjugates, nucleic acids, vectors, host cells, cell populations, or pharmaceutical compositions described herein, in an amount effective to treat the cancer. In exemplary aspects, the method comprises administering a conjugate described herein. In exemplary aspects, the method comprises administering host cells of the disclosure wherein the host cells are autologous cells in relation to the subject being treated. In exemplary aspects, the method comprises administering host cells of the disclosure wherein the host cells are cells obtained from the subject being treated. In exemplary aspects, the cells are T-lymphocytes. In alternative aspects, the cells are natural killer cells.

The disclosure provides materials and methods that are adaptable and can serve as the basis for a platform technology with considerable growth potential. The cancer-specific nature of Tn-glycopeptides are expected to provide targets for cancer prophylactics and therapeutics that offer major advantages over previously and presently used targets.

The disclosure also provides a method of glycoengineering cancer cells by knocking out Cosmc using zinc-finger nucleases (SimpleCells). The same cancer cells are used in direct comparative analyses of TCR- and CAR-transduced T cells targeting peptide-MHC and Tn-glycopeptides, respectively. In addition, Tn-glycopeptide-specific CARs are tested for toxicity to normal tissues in fully syngeneic systems. Further, a panel of isogenic Cosmc-deleted cell lines from common human cancers are used for generating important new sets of monoclonal antibodies to human cancers, including those that are deficiently glycosylated due to mechanisms other than Cosmc mutation. These antibodies are used for making new CARs and fusion proteins for human therapy. As disclosed herein, high local levels of IL15/IL15Rα at the tumor margin and around the tumor vessels empower NK cells to eradicate large, solid, long-established tumors by delivering an scFv-IL15/IL15Rα fusion protein into and around the tumor.

Figure 8:
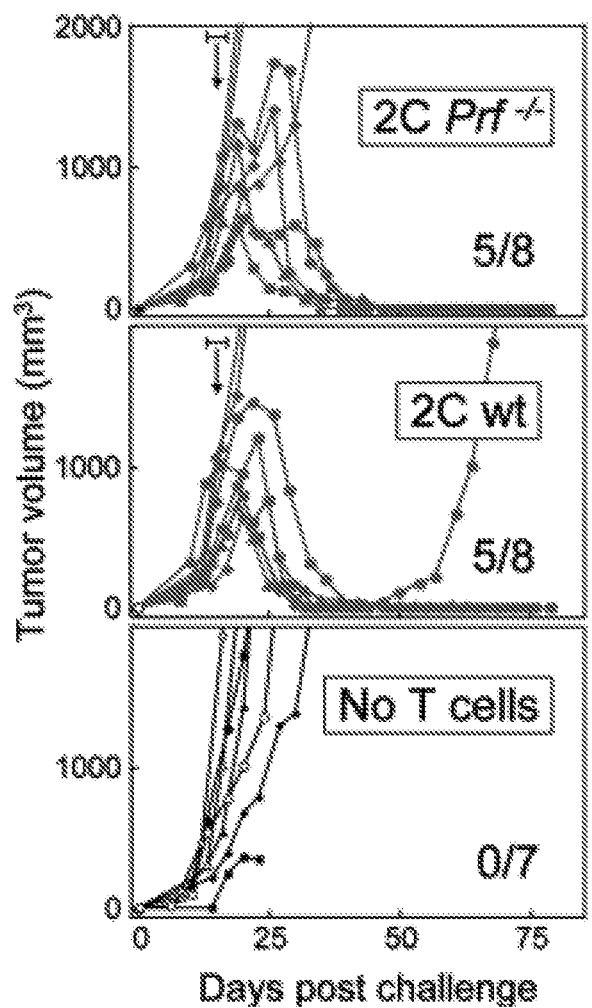
FIG. 8. Perforin is not needed for the rejection of established tumors in normal mice. 2C $Prf^{-/-}$ or 2C wt T cells activated in vitro, were adoptively transferred into MC57-SIY tumor bearing mice when tumors reached about 500 mm$^3$ (between days 13-17 as indicated by the horizontal bars). The number of rejected tumors per total number of tumors is indicated. Data are pooled from 5 independent experiments.

Additional data disclosed herein establish the role of stromal cells in cancer eradication, the mechanism of destruction of antigen-loss variants, and whether cross-presentation of tumor antigen by vessels is essential for tumor destruction. The results establish a coherent picture: stromal cross-presentation, including cross-presentation by vessels or other stromal components, is not required for eradication of large solid tumors when using TCR-transduced CD8+ T cells that target cancer cells only directly. These results provide strong basis for expecting CAR-transduced T cells to also target cancer cells directly. But for eradication, it is necessary that cancers not escape by loss of antigen. When cancers do contain antigen-loss, or epitope-loss (used synonymously with antigen-loss in this context), variants, the situation is different. Now, cross-presentation of the tumor antigen by tumor stroma (both hematopoietic and sessile compartments) becomes important. Furthermore, these stromal cells must express the cross-presenting MHC Class I molecule, as well as the receptors for IFNγ and TNF. Surprisingly, the transferred T cells must produce TNF and IFNγ, while perforin production is not required for tumor eradication by these T cells (see FIG. 8).

An example of the tumor specificity that can be achieved via mutation is presented by the cloned mutant p68 (mp68)-specific TCR (1D9). The peptide binds with sub-nanomolar affinity to the MHC Class I molecule $K^b$ expressed by the cancer cells (29). T cells transduced with this TCR are extremely powerful (FIG. 2) and eradicate large solid tumors expressing the $K^b$-restricted mutant p68 peptide through direct recognition of the cancer cells in the absence of any cross-presentation. Because the antigenic structure that anti-Tn-O-glycopeptide CARs recognize is destroyed when cross-presented on the MHC of host antigen-presenting cells (3, 30, 31), T cells transduced with such CARs must also eradicate tumors by direct recognition only. Thus, 1D9-transduced T cells are used as a guide for what is needed to make T cells transduced with CARs equally effective in eradicating the same tumor. As briefly noted above, one approach to expanding the collection of tumor-specific antigens is based on the mutational loss-of-function of a chaperone that converts a wild-type protein into a tumor-specific Tn-O-glycopeptide antigen on a murine tumor (16).

Figure 4:
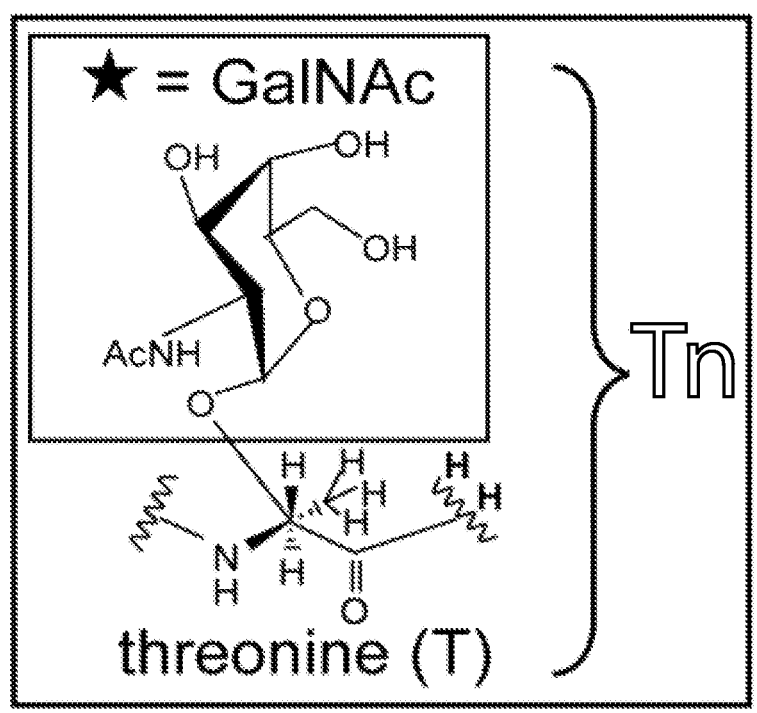
FIG. 4. Many common cancers express Tn antigen (1, 2). Tn antigen is one of the earliest identified on human tumors. Chemically, Tn is N-acetylgalactosamine (GalNAc) linked by an (α1-O—) linkage to threonine or serine on the peptide chain of any protein. Importantly, the peptide sequence is not part of the Tn antigen and not recognized by anti-Tn antibodies. Unlike 237 or 5E5 antibodies binding Tn-O-glycopeptide epitopes, these anti-Tn antibodies (FIG. 3) bind only to the linked sugar without recognizing any neighboring amino acid and are regularly of very low affinity. Nevertheless, it is very likely that, as originally found by Georg Springer, ~70-90% of common human cancers breast, colon, prostate, ovary, lung, bladder and cervix express Tn antigen (12). Tn antigen is also on the bacterial flora, HIV-1 and pathogenic parasites (13, 14).

CAR-transduced T cells have eradicated large solid tumors in humans and mice (49-52), But all of these CARs were specific for antigens also expressed on normal human cells and tissues (CD19/CD20, HER2, CEA, mesothelin) and, without exception, caused destruction (CD19+B cells (49, 50)), serious toxicity (9), or death (8) (unless, experimentally tested in mice lacking expression of the targeted antigen on normal tissues, e.g., human HER2 or human mesothelin (51-53)). Basically, all Tn-O-glycopeptide epitopes, whether caused by loss of Cosmc/C1GalT function or not, are chemically the same (FIG. 4). Also any cell, with or without Cosmc/C1GalT function, synthesizes these structures as an intermediate step of further glycosylation. Thus, even Tn-O-glycopeptide epitopes dependent on loss of Cosmc/C1GalT function are not strictly tumor-specific because they must exist as intermediate stages in the Golgi apparatus of healthy/non-tumor cells. However, this stage must be so transient and/or so inaccessible to the immune system that it is neither detected by antibodies nor responsible for inducing tolerance.

The disclosure will be more fully understood by reference to the following examples, which detail exemplary embodiments of the disclosure. The examples should not, however, be construed as limiting the scope of the disclosure.

Example 1

Materials and Methods

Female or male mice 6-10 weeks old are used. Regular and Rag1$^{-/-}$ C67BL/6 mice, OT1 and 2C TCR-transgenic mice on Rag1$^{-/-}$ or regular B6 background and C3H/HeN (wild-type and Rag2$^{-/-}$) and C3B6F1 mice are used for tumor experiments, the derivation of immune cells and as a source of T cells for transduction with CARs and TCRs. Furthermore, Perforin$^{-/-}$, IFNγ $^{-/-}$, TNF$^{-/-}$, and FasL$^{-/-}$ (Fasl gld) mice are used for transfer experiments. DsRed, EYFP, IFNγ-EYFP "Yeti" and NKp46 iCre R26R eYFP mice are used for in vivo imaging experiments. C57BL/6 MUC1-transgenic mice and PymT MUC1-transgenic mice are used for 5E5-CAR-treated MC38 tumor grafts and autochthonous mammary carcinomas. BALB/c mice will be used for immunizations.

A longitudinal optical imaging approach was used that allows us to follow the localization and action of CAR-transduced T cells and fusion proteins in solid tumors in situ. Using the conditions that previously allowed direct targeting by T cells to cause bystander elimination of potential escape variants in the absence of cross-presentation, guides and aids the construction of CAR vectors, as well as developing methods of transducing CARs and activating CAR-transduced T cells. Also the design of fusion proteins and the mode of administration to achieve optimal efficacy are evaluated by imaging.

The statistics disclosed herein vary by type of experiment. Experiment type I: The frequency of tumor eradication, i.e., the percentage of animals tumor- or metastasis-free for 6 months in CAR- or fusion protein (FUSION)-treated versus control mice is compared using Fisher's exact test. Assuming a rate in the control group of 10%, N=16 animals per group provides 80% power to detect an increase to 61% in treated animals, based on a two-sided test at the alpha=0.05 significance level. Experiment type II: Average tumor size at 4 weeks after treatment with CAR/FUSION versus control mice is compared using a two-sample t-test. N=16 animals per group provides 80% power (alpha=0.05) to detect a 1.0 standard deviation (SD) difference in means. For normally distributed data, this effect size would correspond to 84% of the animals in the treated group having final tumor volumes below the median of the controls. Tumor eradication rates in mice deficient in effector molecules versus normal mice is compared using Fisher's exact test; N=16 animals per group is evaluated. Experiment type III: Imaging experiments are performed using N=10 mice per group (CAR/FUSION versus control) with 3 spatial points evaluated per mouse. Outcome measures are quantitative in nature and are analyzed using a mixed effects analysis of variance model to account for the potential within-animal correlation across spatial regions. For count data (e.g., number of YFP+ cells per optical field and number of T cells killing more than one target per field), a square root transformation is applied, if required, to stabilize variances. The sample size will provide 80% power (alpha=0.05) to detect a 0.9 SD difference in means if the within animal correlation, p, is 0.25 (Donner, et al., Am J Epidemiology 114:906-914, 1981). If the correlation is higher, p=0.50, the detectable effect size is 1.1 SD.

Example 2

Figure 6A:
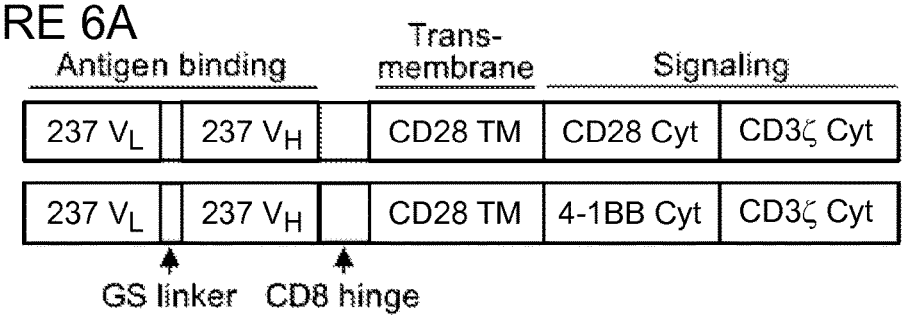
FIG. 6. 237 CAR-expressing CD8$^+$ T cells kill cancer cells expressing the Cosmc-dependent Tn-O-glycopeptide target. (A) Diagram of two variants of second-generation CAR vectors. TM, trans-membrane; Cyt, cytoplasmic domain. (B) 2C TCR-transgenic T cells transduced to express the 237 CAR kill AG104A cancer cells, unless they have (wt) Cosmc activity. As expected, transduced and non-transduced 2C T cells killed AG104A cells expressing $K^b$ and SIY.
Figure 6B:
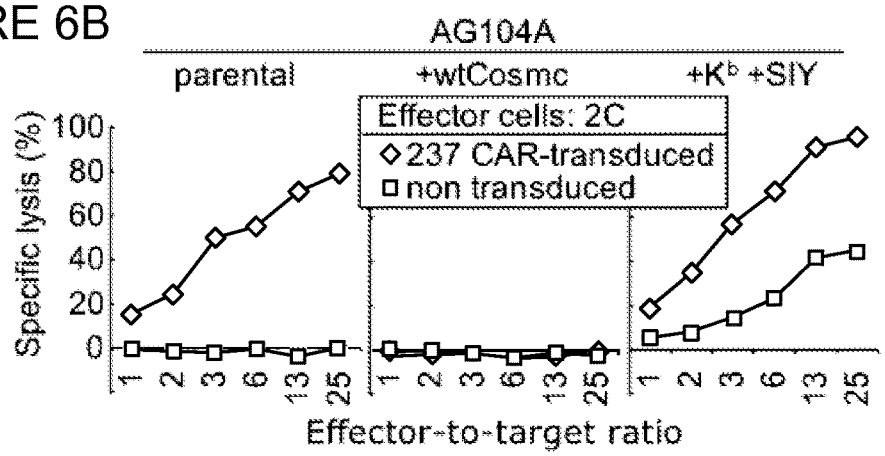
Figure 7:
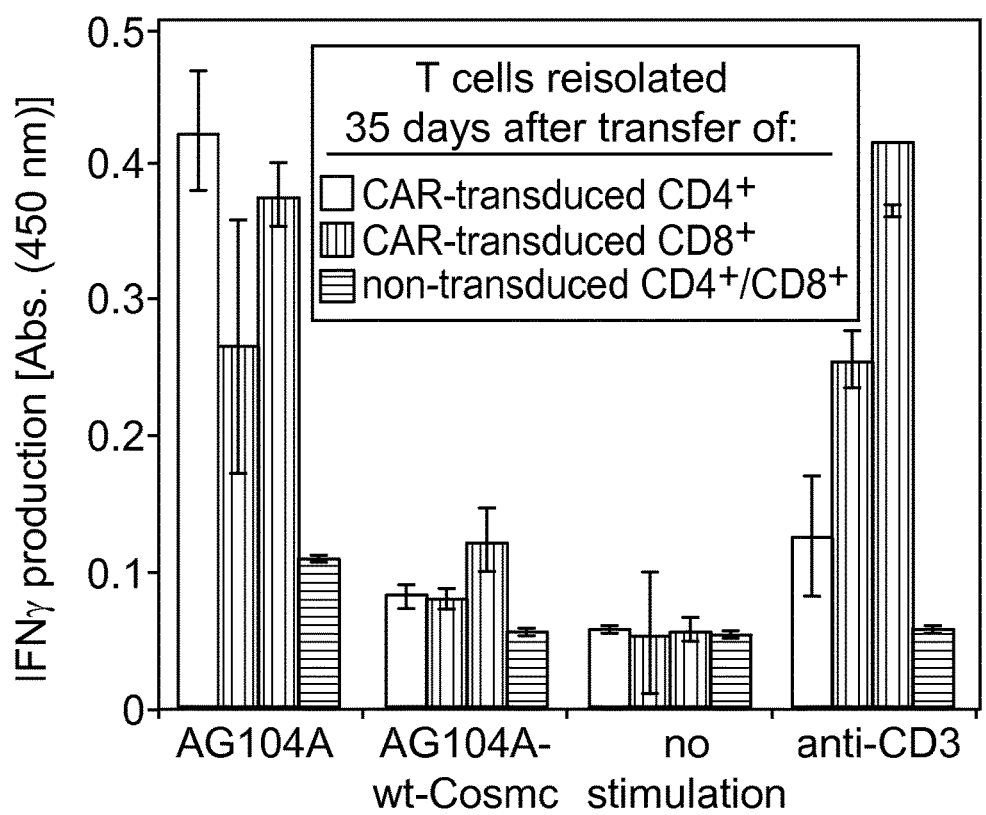
FIG. 7. CAR-transduced T cells survive in vivo and maintain 237 CAR-mediated specificity. $Rag^{-/-}$ mice received 237 CAR-transduced CD4$^+$ or CD8$^+$ T cells of B6 mice. T cells were isolated 35 days after transfer and cultured with different stimuli. IFNγ secretion was measured after 24 hours.

CAR-Transduced T Cells Target a Tumor-Specific Tn-O-Glycopeptide Epitope to Eradicate Solid Non-Hematopoietic Tumors For this experiment, a completely syngeneic model of clinical-size tumors was used. AG104A is an osteosarcoma that developed spontaneously in an old mouse and naturally expresses the tumor-specific Tn-O-glycopeptide, which is targeted with CARs (16). The tumor grows aggressively in normal syngeneic mice and metastasizes spontaneously, i.e., seeds from the primary tumor to the lungs and other organs without intravenous inoculation of cancer cells. The "237 CAR" (59) (FIG. 6A) is based on the syngeneic antibody PW237, derived from B cells of a syngeneic mouse immunized with irradiated AG104A cancer cells (60). 237 CAR-transduced peripheral CD8+ T cells killed very effectively the parental AG104A cancer cells at very low effector to target cell ratios (FIG. 6B and (59)). Repair of the Cosmc mutation completely abrogated the killing (FIG. 6B, middle panel). The 237 CAR-transduced (CAR+) T cells survived long-term after adoptive transfer and maintained function (FIG. 7). T cells that express CARs with a 4-1BB signaling domain (FIG. 6A lower construct) have been used clinically to eradicate large bulky B cell malignancies (49, 50) and have been found to survive better in vivo than CARs lacking this domain (61) (for review see (62)). Thus, this CAR is expected to have advantages over the CD28-containing CAR (FIG. 6A).

The 4-1BB CAR is being generated to test its efficacy in the syngeneic tumor model. $1 \times 10^5$ AG104A cancer cells are injected s.c. into normal C3H mice. AG104A-wtCosmc (AG104A with the repaired mutation) is injected into the control group. Once tumors have reached 500 mm³, mice are treated with lymphodepleting irradiation (4.5 Gy), a dose that has no measurable effect on tumor growth.

Figure 2:
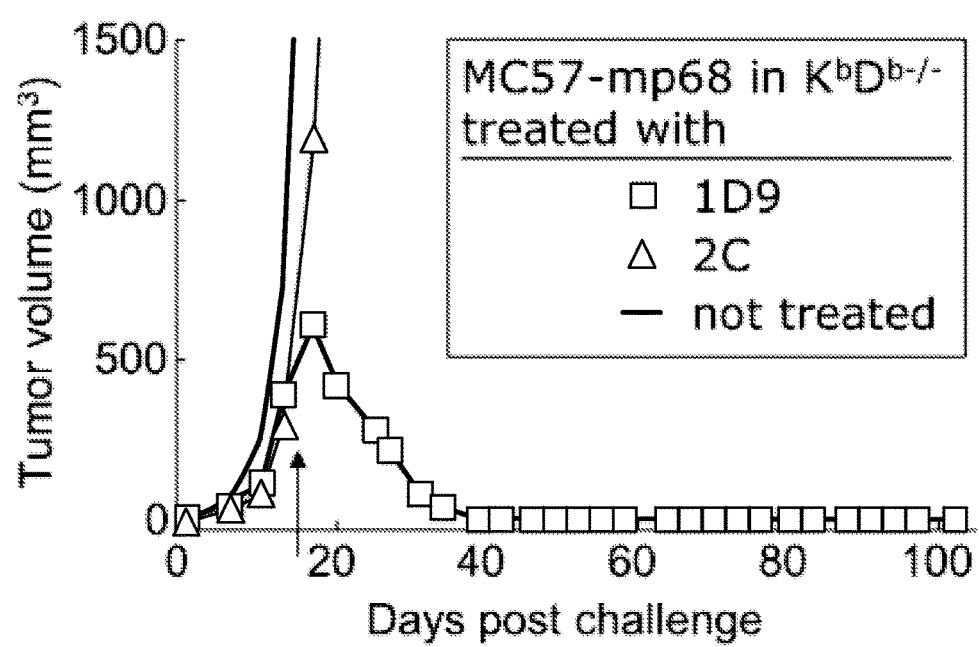
FIG. 2. Large, established tumors are eradicated in the absence of any cross-presentation by the host. MC57-mp68-Hi cancer cells were grown in $Rag^{-/-}$ $K^{b-/-}$ $D^{b-/-}$ mice (that lack MHC Class I molecules needed for cross-presentation) and treated on day 15 (arrow) with cognate (1D9-transduced OT-1) or non-cognate (2C-transduced) T cells, or left untreated.

Fefer and coworkers found that lymphodepletion is important for effective expansion and function of transferred T cells in mice (63). 24 hours after lymphodepletion, $5 \times 10^6$ 237 CAR-transduced sorted CD8+ wild-type C3H T cells are transferred. Tumor size is monitored every three to four days after adoptive T cell transfer. Data on TCR-transduced T cells show that CD8+ cells alone eradicated large solid tumors, if the tumors contain no antigen-loss variants (FIG. 2). The splenic T cells that were transduced contain CD8+ as well as CD4+ T cells. This is expected to be important because CAR-transduced CD8+ T cells may not succeed in rejecting AG104A tumors without help from CAR-transduced CD4+ T cells. CD4+ T cells may provide help to CD8+ T cells or collaborate in the effector phase (64, 65). Rejection of MC57 tumors by adoptive transfer of TCR-transgenic T cells did not require perforin but IFNγ and TNFα were necessary (FIG. 8 and (66)). It has been shown that CAR-transduced T cells express high amounts of perforin (67).

In order to understand mechanistically the basis of rejection, CARs are transduced into T cells of several knockout mice to determine the effector molecules required (e.g., perforin, IFNγ, TNFα and FasL). Should tumors be rejected, mice will be kept for at least 3 additional months, and if no relapse occurs, at least one cage of mice will be monitored for at least one year. With the other mice, the existence of the CAR+ memory T cells will be examined by secondary challenge with AG104A tumors. Repeated attempts to isolate 237-negative variants for the AG104A tumor by stringent sorting have been unsuccessful in the past.

Microdisseminated AG104A cancer cells are expected to be more susceptible to $CAR^P$ T cells than cancer cells in solid AG104A tumors in which tumor-induced immunosuppression may be stronger.

Studies on adoptive transfer of 237 CAR-transduced CD8+ and CD4+ T cells revealed no graft versus host disease (GVHD). Any normal cell must express the 237 CAR-targeted epitope during biosynthesis of normal OTS8/podoplanin. This, however, should not be detected by 237 CAR+ T cells because expression will be transient and intracellular. As one measure of GVHD, body weight was monitored daily for each treated mouse in which tumors were being eradicated by the 237 CAR+ T cells. Furthermore, histological analyses of skin and gut is performed at one month after T cell transfer, at the end of the experiment, and/or when mice should become moribund.

An AG104A line transduced to express $K^b$ as well as mp68 provided the opportunity to compare both mp68-specific 1D9TCR-transduced T cells and 237 CAR-transduced T cells using the exact same model. It is already known that adoptive transfer of T cells transduced with the SIYRYYGL-specific TCR 2C (SEQ ID NO:22) can destroy large solid $K^b$/SIYRYYGL expressing AG104A tumors growing in Rag1$^{-/-}$ C57BL/6 mice. To obtain detailed information on differences in the kinetics of T cell infiltration, target cell engagement, vascular and cancer cell destruction, longitudinal high-resolution optical imaging of the AG104A tumor growing behind a dorsal skin fold glass window was used (71). This technology allowed us to follow the precise sequence of destruction of a long-established solid tumor for weeks. In this, the transfer of T cells to tumor destruction, eradication or relapse was followed. Continuous analysis of the same tumor and even localization of the same spot of the tumor was made possible by a specially engineered frame/stage holder and computerized coordinates, and by improved imaging and anesthesia conditions (for example, see FIG. 9). Imaging was done continuously for many hours a day without noticeable effects of photobleaching/phototoxicity.

Thus, 237 CAR-transduced or 1D9 TCR-transduced $CD8^+$ EYFP B6C3F1 T cells will be transferred into DsRed B6C3F1 $Rag^{-/-}$ hosts bearing AG104A-$K^b$-mp68-Cerulean tumors. In both settings, measurements will be taken of (i) when and where the T cells start to infiltrate (day/hour after transfer and number of cells/area) and (ii) the sequence of destruction of cancer, vascular and stromal cells. As a second cancer model, MC57 fibrosarcoma will be used, which can be eradicated by transfer of cancer-specific T cells (FIG. 1). The cell line will be transduced to express mp68 and the 237 epitope (expression of OTS8 and disruption of Cosmc by zinc-finger nuclease (68)). While tumor eradication by 1D9-transduced T cells seems to be relatively unaffected by the type of T cell transduced, the $CAR^+$ T cells might only be effective in localizing and/or functioning if central or effector memory T cells are transduced (72).

Figure 3:
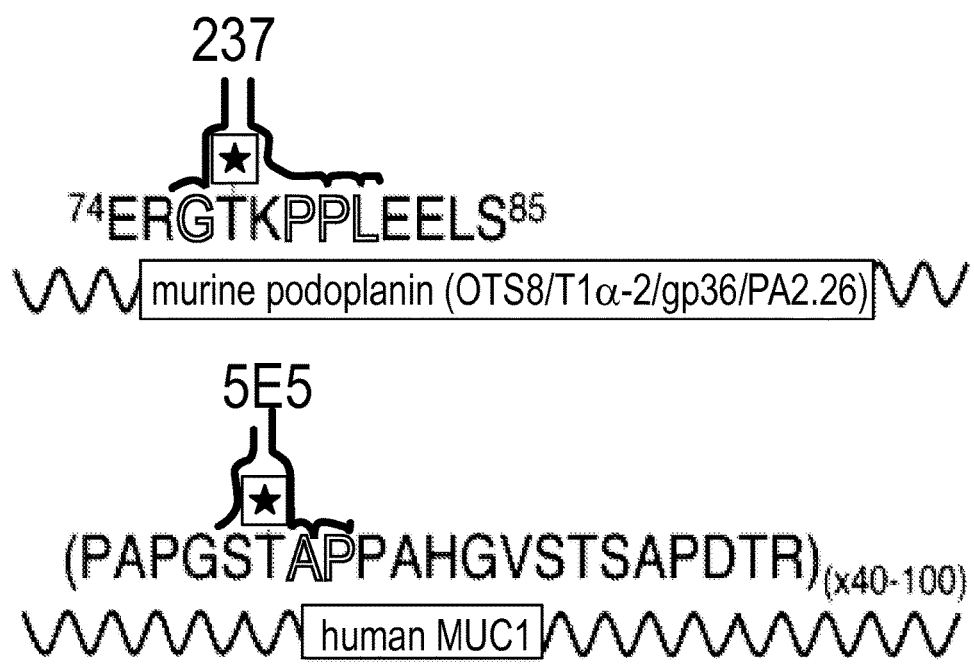
FIG. 3. The Tn-O-Glycopeptide antigen recognized by the high affinity 237 IgG2a antibody contains the Tn hapten, but the antibody does not bind Tn alone (3). Tn (yellow box with black star; T nouvelle (1, 2)) is N-acetylgalactosamine (GalNAc) linked by an (α1-O—) linkage to threonine or serine on the peptide chain of any protein (see FIG. 4). By contrast, the Tn-glycopeptide epitope is highly defined as N-acetylgalactosamine (GalNAc) at position 77 and the specific amino acid of murine podoplanin/OTS8 surrounding this position (4). X-ray crystallography shows that the antibody completely engulfs the carbohydrate moiety itself while interacting with the unique sequence of the peptide moiety in a shallow groove (3). The relevant amino acid contact residues were identified by X-ray crystallography (green letters, (3)). Appearance of the antigen in the AG104A cancer is caused by a tumor-specific somatic mutation that destroys the chaperone Cosmc, essential for functioning of the Core1 β1,3-galactosyl-transferase, (C1GalTor T-synthase) (see FIG. 1). Like 237, the anti-human MUC1 antibody 5E5 (U.S. Pat. No. 8,440,798, incorporated herein by reference) also lacks demonstrable reactivity with the naked MUC1 peptide. However, the 5E5 antibody-recognized antigen is also expressed by human OVCAR-3 ovarian, NNP4 ovarian and MCF-7 breast cancer cells, and the like, that have normal Cosmc/C1GalT function. Thus, the appearance of this epitope has a different mechanism (see FIG. 1). The minimal epitope of 5E5 was characterized by alanine replacement scans (green letters, (5)). 5E5 and 237 are being developed into CARs and bispecific fusion proteins.

The two Tn-O-glycopeptide-specific antibodies used in the studies disclosed herein, 237 and 5E5, are high affinity antibodies recognizing defined Tn-O-glycopeptide epitopes on cancers (FIG. 3). Importantly, the Tn-O-glycopeptide epitope 5E5 is widely expressed on several common types of human cancers without requiring them to have lost Cosmc function. Also, no reactivity to normal tissues has been shown for 5E5 (FIG. 5) (35-38). Mutational deletion of Cosmc (39) or C1GalT (40) is embryonically lethal, and it is expected that CARs targeting Tn-O-glycopeptides in cancers cause no toxicity in normal tissues of the host. Furthermore it is unlikely that there is neonatal or peripheral tolerance to Tn-O-glycopeptide epitopes before the host is exposed to them following somatic mutational loss of Cosmc or C1GalT function (41). Consistent with this notion, the "Tn syndrome" (1, 2) caused by a somatic Cosmc mutation in bone marrow stem cells (42) is a spontaneous hemolytic autoimmune disorder. Similarly, deletion of the Cosmc/C1GalT gene in intestinal mucosa causes spontaneous immune responses and spontaneous severe ulcerative type colitis in mice (33). Consistent with this finding, patients with ulcerative colitis harbor spontaneous somatic loss mutations of Cosmc in affected colonic mucosa (33). This is in line with the tight linkage between inflammation and colon and many other types of cancers (43, 44). Indeed, mutational loss of Cosmc occurs in colon cancer, such as in the line LSC (17, 45). It is expected that the basis for mutational deletion of Cosmc/C1GalT causing such strong spontaneous immune responses is that the mutation leads to exposure of a vast number of Tn-peptide epitopes, with such epitopes being recognized by helper T cells (46, 47). Lack of tolerance to these epitopes (41) is consistent with the spontaneous anti-Tn-O-glycopeptide immune responses in cancer patients against the cancer-associated glycoforms of these proteins (48). Apparently, medullary thymic epithelial cells present only fully glycosylated forms of a protein, but not the cancer-associated forms of the protein (41).

Example 3

Fusion Proteins Specific for a Tumor-Specific Tn-O Glycopeptide Epitope that Also Express IL15/IL15Rα

Figure 11:
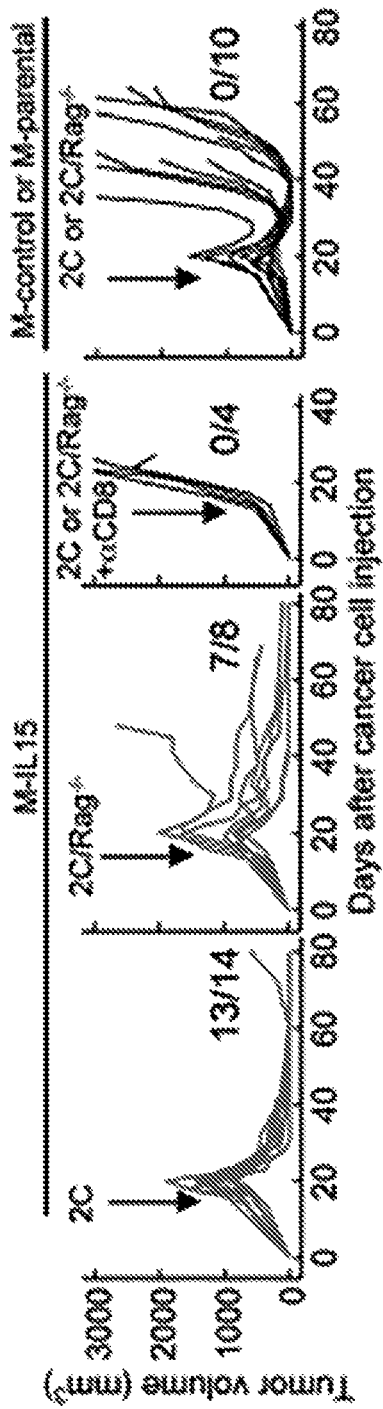
FIG. 11. IL15 can induce CD8$^+$ T cell-dependent eradication of tumors that lack cognate antigen. $Rag^{-/-}$ γC$^{-/-}$ mice received s.c. IL15-secreting, control vector-transduced or parental MC57 (M) cells, all lacking the SIY antigen recognized by adoptively transferred 2C or 2C/$Rag^{-/-}$ splenocytes. T cells rejected tumors that secreted IL15. Depletion with anti-CD8 abrogated this effect.

Cell-based therapies using T cells transduced with CARs or TCRs require ex vivo manipulation of autologous lymphocytes that must be isolated from each individual patient and transduced before re-infusion. Alternatively, fusion proteins that use specific epitope recognition domains from antibodies (73) or TCRs (74) can be given to patients as "off-the-shelf" drugs. Local expression of IL15 and IL15Rα in solid tumors induced the rejection of established tumors by densely granular NK cells in a T cell-free model (FIG. 10 and (7)). Further studies showed that high local levels of IL15 enabled adoptively transferred T cells to eradicate established solid tumors expressing IL15Rα in an antigen-independent fashion (FIG. 11). Therefore, a "BITE-like" superfusion protein, i.e., 237-IL15/IL15Rα, which uses IL15/IL15Rα instead of anti-CD3 to engage the effector cells, was constructed. The versatility (effects on T cells as well as NK cells) as well as the safety of IL15 makes this cytokine extraordinarily relevant therapeutically.

The 237-IL15/IL15Rα superfusion construct (237-superfusion) contains four folded domains: 237 VL, 237 VH, IL15Rα sushi domain, and IL15 (N- to C-terminus) linked by Gly-Ser-based linkers (FIG. 12). Existing studies provide evidence of the effects of two IL15/IL15Rα constructs in vitro as well as in vivo. In vitro, the 237-superfusion showed (i) specific binding to immobilized OTS8 glycopeptide, (ii) effective displacement of 237 antibody binding to AG104A cells in competition assays (by FACS), (iii) specific binding to Jurkat cells transduced with the OTS8 protein, and (iv) potent stimulation of proliferation of CTLL-2 cells when compared to soluble IL15 (FIG. 12). Thus, it is expected that delivery of IL15 and IL15Rα into the tumor by 237-superfusion proteins will strongly stimulate both adaptive and innate immune cells. In vivo, the IL15/IL15Rα superfusion protein overcomes the common problem of targeting cancers expressing little or no detectable IL15Rα (a recent study established that IL15Rα expression by the cancer is important for the tumor-destructive effects of IL15 by NK cells (7)). The 8215 cell line, a newly induced cancer line from IL15Rα-deficient mice, was eradicated when transduced to express the superfusion protein (FIG. 13A).

In addition, the superfusion construct causes substantial and durable in vivo expansion of T and NK cells in the spleen of mice that received superfusion-transduced spleen cells 29 days earlier (FIG. 13B). Yet another effect of the 237-superfusion construct is that delivery of IL15/L15Rα to the tumor led to the generation of densely granulated NK cells, such as those observed in tumors overexpressing IL15, including AG104A (FIG. 13E, and (7)). Additionally, subcutaneous implantation of an osmotic pump releasing the 237-superfusion protein caused massive local tissue-destructive densely granulated NK cell infiltrates similar to those that destroy very large established cancers (FIG. 13C, D and (7)). The main effect of the 237-superfusion protein was massive local tissue destruction at the site where the superfusion protein was released from the pump, causing rupture of the skin over the implanted pump and termination of the experiment. While there was no evidence for systemic toxicity, there was a systemic effect on the Tn-glycopeptide expressing AG104A tumor growing on the contralateral side relative to the pump (induction of granulated NK cells), and this effect is expected to increase dramatically when the fusion protein is released using an intravenous catheter in combination with the osmotic pump.

These in vivo and in vitro results have led to the design of experiments investigating the antitumoral effects of 237-IL15/IL15Rα superfusion in three AG104A tumor models: prevention of tumor outgrowth, treatment of established solid tumors, and microdisseminated disease. Experiments are performed to study the pharmacokinetics of the fusion protein to find the optimal dose that effectively prevents tumor outgrowth in immunocompetent C3H mice. Towards this end, 450, 150, 45, 15, and 5 µg/kg are tested in 2-week daily treatment courses. The most effective dose is used to treat established AG104A tumors and microdisseminated disease. Given the data on the in vivo effects of the fusion protein, anti-tumor effects are expected in each of the three models. Rag$^{-/-}$ mice (containing only NK cells) are used as hosts to distinguish between NK- and T cell-mediated effects. Groups of Rag$^{-/-}$ mice bearing AG104A are treated with: (i) 237-superfusion, (ii) T cells specific for an irrelevant antigen (2CRag$^{-/-}$), or (iii) 237-superfusion+ 2CRag$^{-/-}$ T cells. Because the delivery of IL15/IL15Rα to the tumor is already known to lead to the generation of densely granulated NK cells, optical imaging will be helpful to analyze the mechanisms and kinetics of T cell- and NK cell-mediated tumor destruction. The granulation of NK cells is visible in the transmitted light channel at high magnification (40×), so NK cells will be tracked using NKp46 iCre R26R eYFP NK-reporter mice (75). Thus, DsRed$^+$ 2 CRag$^{-/-}$ T cells will be transferred into NKp46 iCre R26R eYFP Rag$^{-/-}$ mice bearing AG104A-Cerulean tumors. YFP NK/DsRed T cell infiltration kinetics and cancer cell destruction are compared in 237-superfusion-treated versus untreated mice.

While the above experiments test a 237-IL15/IL15Rα superfusion protein targeting a murine Tn-O-glycopeptide, a IL15/IL15Rα fusion protein in which the 237 domain is replaced with the 5E5 receptor is also generated. It is expected that the results observed following administration of the 5E5-IL15/IL15Rα superfusion protein in humans will be analogous to the results seen upon administration of the 237-IL15/IL15Rα superfusion protein to mice.

Example 4

Figure 5:
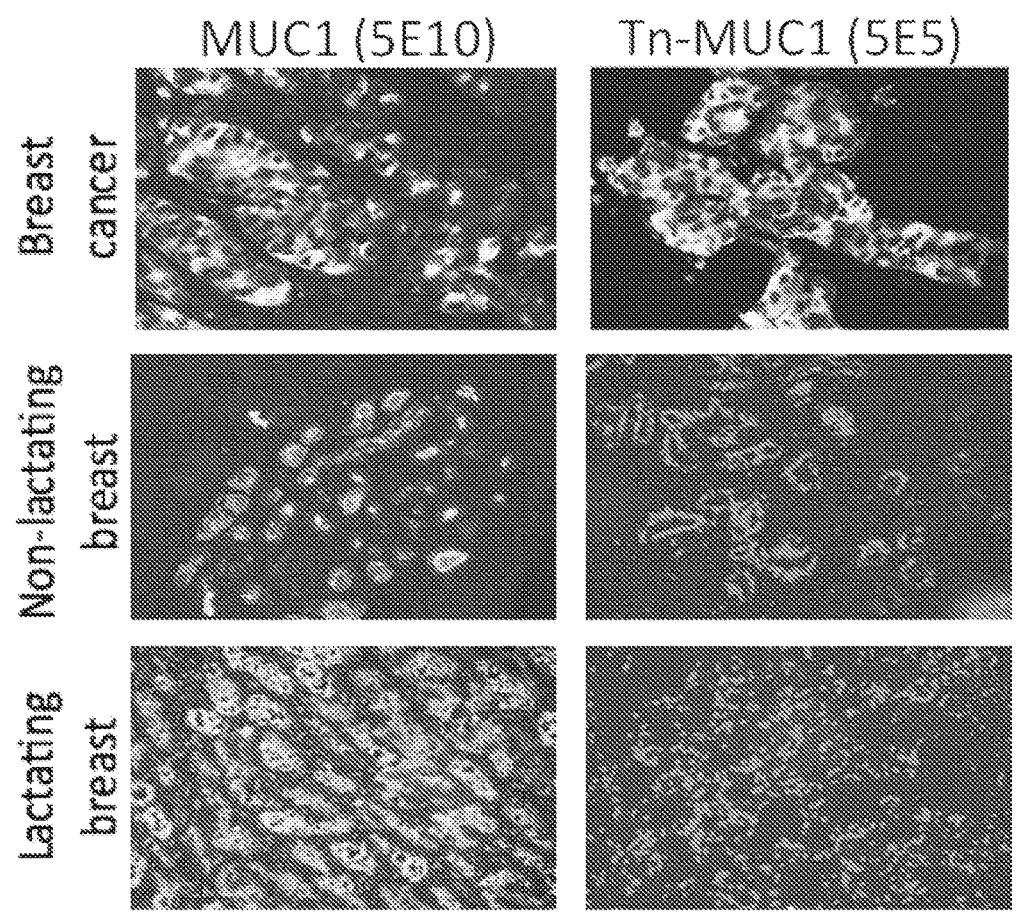
FIG. 5. The 5E5 Tn-MUC1 glycopeptide epitope is recognized in breast cancer but absent from normal breast tissue in which the 5E10 monoclonal antibody recognizes normal MUC1.

CARs Targeting Tn-O-Glycopeptide Epitopes on Human Cancers with Normal or Mutant Cosmc Genes The influence of Cosmc on the anti-cancer effects of CARs targeting Tn-O-glycopeptide epitopes on human cancer cells is assessed using wild-type, or normal, Cosmc competent to chaperone and mutant Cosmc lacking this capacity. Two complementary approaches are available. Data show that the 5E5 antibody recognizes human ovarian and breast cancers but neither non-lactating nor lactating normal human breast (FIG. 5).

The 5E5 anti-Tn-MUC1 antigen-receptor gene, optimized for expression (see Example 5) is ligated into a lentiviral vector for insertion into human T cells. The transduced T cells are then tested in standardized in vitro assays to provide required preclinical safety information. In addition, the in vivo efficacy of 5E5 CAR-transduced human T cells is examined following infusion of the transduced T cells into mice bearing human tumor xenografts.

The complementary approach uses a fully syngeneic model to test the efficacy and potential toxicities of the 5E5 CAR. Complementing the above xenograft testing (76) with a fully syngeneic system is important because xenograft models have been reported to pose problems (77), which include evidence from our data that infusing human T cells into mice can have not only graft-versus-tumor but also graft-versus-stroma (without evidence of weight loss) and systemic graft-versus-host effects. The latter often only occurs once the tumor xenograft has been rejected. The aim is to examine whether 5E5 CAR-transduced T cells can eradicate the cancer without causing toxicity to the host expressing the same, but fully glycosylated, protein on normal tissues. For the experiment, human MUC1-transgenic mice that express human MUC1 similarly to humans are used, which provide an important control to ensure the cancer-specificity of the 5E5 CARs. It has been shown that the C57BL/6-derived MC38 colon cancer transfected to express human MUC1 is deficiently glycosylated and will grow progressively in human MUC1-transgenic mice. Vaccination can be protective but is not therapeutic once tumors develop (78). To generate T cell effectors, the 5E5 receptor cloned, optimized for expression and verified, and a 5E5 CAR γ-retroviral vector is under construction. Thus, T cells from human MUC1-transgenic mice will be transduced to treat murine MC38 colon cancer transfected to express human MUC1.

In the first round of experiments, MC38 cells in which the Cosmc gene is deleted by zinc-finger targeting (68), are used. These cells, referred to as MC38sc (sc refers to SimpleCells), express Tn-glycopeptides at the highest levels, similar to human cancers with a tumor-specific mutational Cosmc deletion. Human MUC1 expression vectors allow the expression of (i) the wild-type form, which is largely transmembrane but partially shed, (ii) a secreted form that contains no transmembrane domain, and (iii) both wild-type and secreted forms. The separation between the form that is only secreted and the wild-type form facilitates determining whether expression of MUC1 on the cancer cell membrane is essential and also whether the secreted protein elicits tumor rejection (when expressed exclusively) or whether it has an inhibitory effect on tumor rejection (when co-expressed with the wild-type form). The results will guide the selection of the most appropriate Tn-glycopeptide epitopes (i.e., exclusively transmembrane and/or also secreted). In addition to the transplanted MC38 tumor model, established autochthonous mammary tumors developing in PymT/human MUC1-double transgenic mice will also be targeted to determine whether 5E5 CAR-transduced T cells destroy established autochthonous (non-transplanted) mammary tumors, as well as prevent their development. The autochthonous model will allow the use of immunocompetent mice that will be conditioned before T cell transfer.

Figure 14:
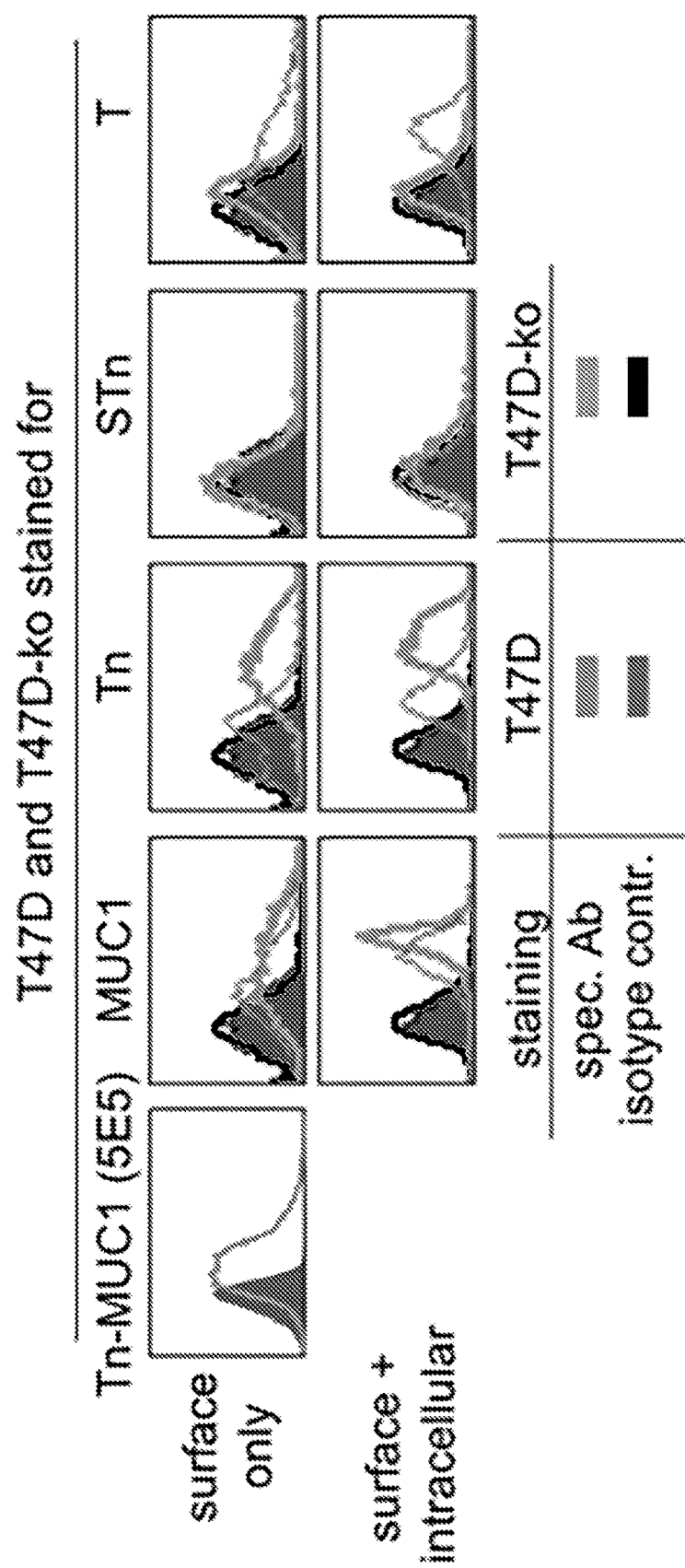
FIG. 14: Glycophenotype of wild-type (T47D, pink) and Cosmc-knockout T47D (T47D-ko, blue). Wild-type T47D cells express 5E5, and Tn on their surface (non-permeabilized; surface only), while more Tn is detectable when Cosmc is knocked out (T47D-ko). Permeabilization (surface+intracellular) of the cells exposes Tn and especially MUC1 epitopes. Flow cytometry analysis of wt and Cosmc-ko T47D cancer cells using antibodies for Tn-MUC1 (5E5), MUC1 (HMFG-2), Tn (5F4), STn (3F1) and T (3C9) with the respective isotype controls.
Figure 15:
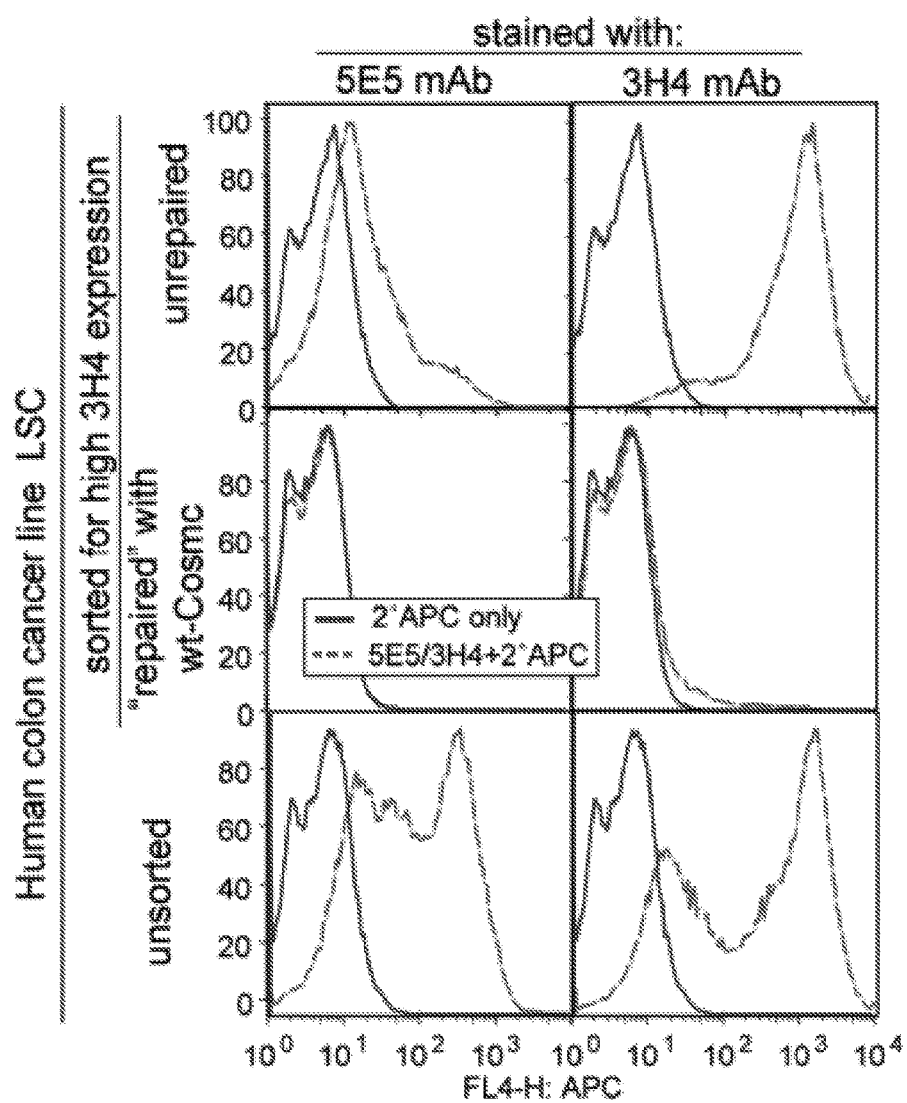
FIG. 15. Antibodies 5E5 and 3H4 detect epitopes on two independent proteins. Monoclonal antibodies were used to stain the human colon cancer line LSC (red lines). LSC was analyzed before (unsorted) or after a sort for cells expressing high levels of the 3H4 epitope. Sorted cells were additionally transduced to express wt-Cosmc, whereby both 5E5 and 3H4 binding is lost. Red tracing—experimental condition containing secondary APC-antibody and either 5E5 or 3H4 primary antibody; blue tracing—control containing secondary APC-antibody only.

Disclosed herein is the observation that immunization of mice with murine or human cancer cells that lack Cosmc is a highly effective way to induce Tn-O-glycopeptide-specific, cancer-specific antibodies (16, 34), because Tn-O-glycopeptide epitopes are strongly upregulated by deletion of Cosmc (FIG. 14). To induce such antibodies that are reactive with common cancers, we used three i.p. inoculations of viable human colon cancer LSC that lacks Cosmc (17). To prove that Tn-O-glycopeptides are being targeted, the positive staining by the antibody must be abrogated when the glycosylation defect of LSC has been "repaired" by transduction with wild-type Cosmc (wt Cosmc), see FIG. 15. This dependable indicator was already used in the initial screening and only wells whose positive staining reaction was fully abrogated were retained.

Figure 16:
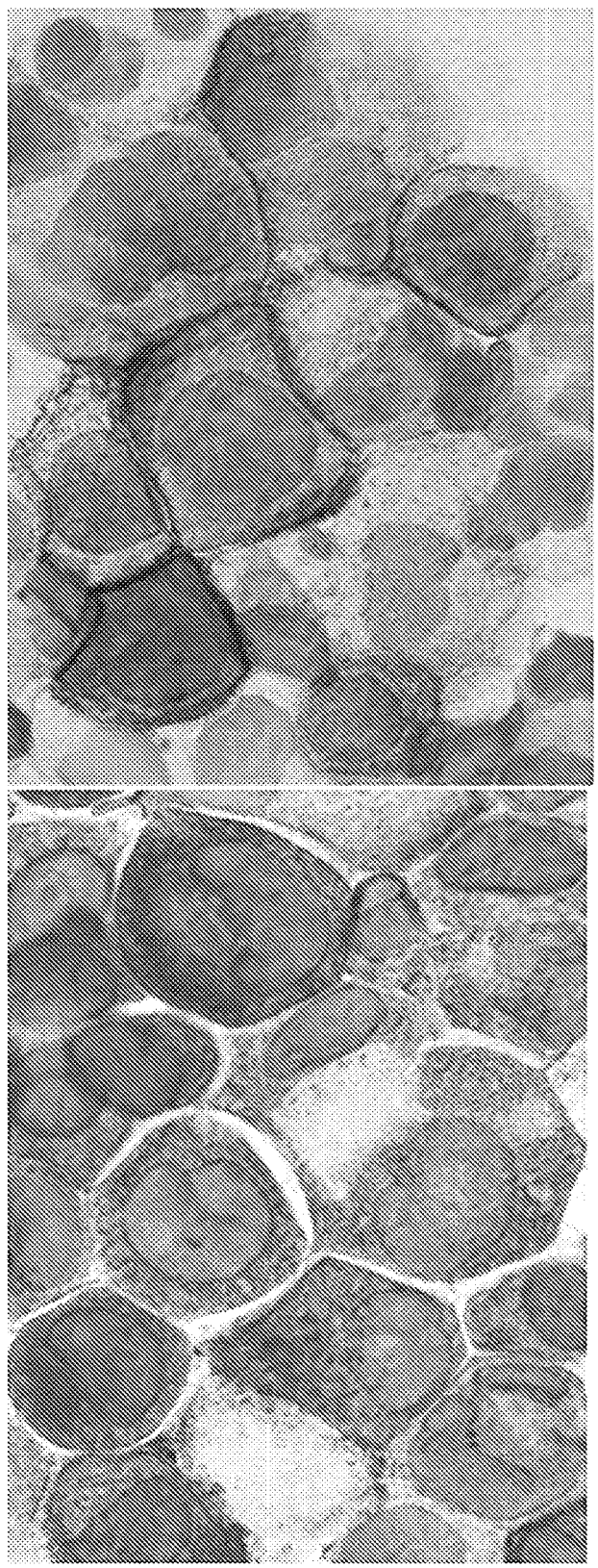
FIG. 16. Expression of two different Tn-glycopeptide antigens on human ovarian cancer cells isolated from an effusion. NNP4 cancer cells were isolated 2 years after diagnosis from the third relapse following various chemotherapies. Left panel—staining by 5E5 monoclonal antibody (mAb); right panel—staining by the 3H4 mAb (dark, granular staining). Nuclei are also labeled. Control stainings were negative.

Using this approach, the 3H4 monoclonal IgG antibody was recently selected. LSC cells sorted for high expression of 3H4 show no upregulation of 5E5 (FIG. 15), thereby indicating that 3H4 recognizes a Tn-O-glycopeptide epitope on a protein other than MUC1. 3H4 also binds to the human ovarian cancer cells NNP4 that do not have a Cosmc mutation (FIG. 16). The choice of targets will be extended to additional common cancers of other organs such as breast, ovary and prostate using the T47D, OVCAR-3 and LNCaP cell lines, respectively (68). Using the SimpleCell approach, variants of the three cancer cell lines with and without knocked-out Cosmc have been generated. Additional engineered KO-lines for pancreas (Capan-1) and colon (Colo205) are also available and contemplated for use in the methods according to the disclosure.

To get B cells expressing high levels of an anti-MUC1 monoclonal antibody, BALB/c mice are immunized with viable human Cosmc-mutant cancer cells of several histological origins and boosted twice. The spleen cells are then fused with SP2/O myeloma cells for generation of hybridomas. As done with 3H4, primary selection of antibodies is based on a strong differential reactivity between Cosmc-deficient and Cosmc-functional lines detected by flow cytometry (optional methods have been described (5, 34-36, 38)). Among the selected antibodies, we expect some antibodies that, like 3H4, also react with Tn-positive but Cosmc wild-type cancer cells. The next step of selection is based on reactivity with specific Tn-O-glycopeptides from extracts of SimpleCells by Western blot analysis (68). Antibodies without glycopeptide specificity will react with many or all glycopeptides expressing Tn.

Further selection is based on a requirement for Tn glycosylation. This will be tested as (i) lack of binding to non-glycosylated peptide, (ii) loss of binding after enzymatic extension of Tn on target glycopeptides by β1,3Gal (C1GalT) or α2,6NeuAc (ST6GalNAc-I) transferases (36) and (iii) loss of binding to the target Tn-glycopeptide after enzymatic removal of the Tn structure (exo-N-acetyl-galactosaminidase treatment) (79). Selection for Tn-glycopeptide specific antibodies is expected to eliminate a major fraction of self-reactive hybridomas lacking tumor-specificity. This will be followed by testing on various nonmalignant human cells and tissues by histo- and cytochemistry and flow cytometry. Once the bulk of unwanted hybridomas is excluded, the targeted proteins are identified by immunoprecipitation and amino acid micro-sequencing.

To pinpoint the Tn-O-glycopeptide epitopes for selected antibodies, two strategies are envisioned: 1) a one-bead-one-compound (OBOC) containing about 16,000 unique Tn peptides composed of randomized amino acids, which can define the minimum epitope and flexibility of the peptide sequence recognized, and 2) chemo-enzymatically produced glycopeptide scans for identified glycopeptide targets, which will allow specific assignment of the reactive glycopeptide epitope (5, 34, 48, 80). Initially, the focus is on Tn-O-glycopeptide epitopes shared and most highly expressed by several types of cancers. Ideally, the Tn-O-glycopeptide epitopes are also part of cell-surface glycopeptides that are essential for cell survival or malignancy, which reduces the ability of the cancer cells to escape CAR attack by losing the expression of the glycopeptide. Alternatively, simultaneous targeting of Tn-O-glycopeptide epitopes on two independent cell surface molecules, such as those recognized by 5E5 and 3H4, is expected to greatly reduce the rate of cancer escape from CAR therapy.

Example 5

CARs and Other Receptor Constructs Containing Codon-Optimized Coding Regions

CARs comprising the coding region for an a chimeric antigen receptor against cancer-specific Tn-glycopeptides were constructed using codons optimized for expression in humans or mouse (e.g., 5E5 CAR (SEQ ID NO:7) and 3H4 CAR (SEQ ID NO:13)). Optimization was aided by analytical software provided by GeneArt®. Codon optimization reflects a balance between accommodating mutational biases and facilitating the translational aspect of protein expression. In vertebrates such as man, mouse, domesticated animals and pets, the relatively slow rate of growth of the organisms has led to codon optimizations that largely reflect minimization of the probability of mutation. In faster growing organisms such as prokaryotes and lower eukaryotes (e.g., yeast), the rapid growth rates of the organisms has led to codon optimizations that maximize translation by selecting for codons recognized by the most abundant tRNAs.

This aspect of the disclosure contemplates codon optimizations reflecting any balance between accommodating mutational biases and facilitating protein translation. In some particular embodiments, the disclosure provides unexpected codon optimizations that facilitate translation in higher eukaryotes such as vertebrates, e.g., man, mouse, domesticated animals and pets. Optimizing codons in these animals by selecting codons on the basis of relative tRNA abundances involves a dramatic shift in the approach to codon optimization in higher eukaryotes, yielding a surprisingly beneficial effect on CAR expression and the associated anti-cancer effects of CAR proteins. Optimization of the codons encoding a CAR by any means is expected to improve translation efficiency and/or accuracy, thereby leading to greater production of high-quality CARs. An example of a codon-optimized construct, in which the target-binding variable regions of the CAR are codon-optimized to maximize translation, is provided below.

The codon-optimized coding regions were bounded by 5'-GCGGCCGCCACC-3' (SEQ ID NO:23) at the 5' end and 5'-CTCGAG-3' (SEQ ID NO:24) at the 3' end to provide a 5'-terminal NotI site and a 3'-terminal XhoI site to facilitate the cloning of the 5E5 polynucleotides according to the disclosure into lentiviral vectors known in the art. An exemplary lentiviral system suitable for such cloning is the ViraSafe™ Lentiviral Expression System (Cell Biolabs, Inc.). The lentiviral clones are suitable for use in transducing human or mouse T cells.

Given the variety of bivalent binding proteins disclosed herein and known in the art, it is useful to have codon-optimized polynucleotides encoding discrete elements of the coding region of such a protein. To facilitate the process of engineering such polynucleotides, the disclosure provides polynucleotides comprising the variable region of the heavy (gamma) chain of an antibody against a cancer-specific Tn-glycopeptide, codon-optimized for expression in human or mouse (SEQ ID NO:3 for the 5E5 VH; SEQ ID NO:9 for the 3H4 VH). Other polynucleotides comprise the variable region of the light (kappa) chain of an antibody against a cancer-specific Tn-glycopeptide, codon-optimized for expression in human or mouse (SEQ ID NO:5 for the 5E5 VL; SEQ ID NO:11 for the 3H4 VL). A linker suitable for joining these variable regions in scFvs comprises the codon-optimized sequence provided in SEQ ID NO:14, which is expected to be expressed without difficulty in most vertebrate animals, including humans. A signal peptide useful in maximizing the presentation of a bivalent binding protein by a transduced cell such as a T cell is the codon-optimized polynucleotide comprising SEQ ID NO:1 (the 5E5 CAR construct) or SEQ ID NO:8 (the 3H4 construct), which are expected to function in most vertebrate animals, including humans.

In one embodiment, the lentiviral clone comprising SEQ ID NO:7 (the 5E5 CAR construct) or SEQ ID NO:13 (the 3H4 construct) is transduced into autologous T cells obtained from a human patient suffering from cancer using conventional transduction methodologies. The transduced T cells are then cultured to allow expression of the CAR and to expand the transduced T cell population using conventional culturing techniques.

Autologous CAR-transduced T cells are administered to the patient, with the dosage being optimized for efficacy and non-toxicity on a case-by-case basis, as is routine in the medical arts. Effect on an existing cancer, e.g., a cancer forming a solid tumor, is monitored until the patient is in remission. Prophylactic doses of CAR-transduced T cells may be administered to patients in remission, or to human subjects at risk of developing cancer, such as a cancer forming solid tumors.

In an analogous manner, an anti-cancer-specific Tn glycopeptide CAR is constructed comprising SEQ ID NO:7 (the 5E5 CAR construct) or SEQ ID NO:13 (the 3H4 construct), with codons optimized for maximal translation in mouse cells. The codon-optimized polynucleotide of SEQ ID NO:7 (5E5) contains the coding region for a chimeric antigen receptor having the structure of NH$_2$-signal peptide-anti-Tn glycopeptide VH-linker-anti-Tn glycopeptide VL-CO$_2$H. The codon-optimized polynucleotide of SEQ ID NO:13 (3H4) contains the coding region for a chimeric antigen receptor having the structure of NH$_2$-signal peptide-anti-Tn glycopeptide VL-linker-anti-Tn glycopeptide VH-CO$_2$H. The polynucleotide of SEQ ID NO:13 may be bounded by a NotI site at the 5' end of the polynucleotide and by an XhoI site at the 3' end of the polynucleotide. These restriction endonuclease sites facilitate cloning the polynucleotide into a vector, and one of skill in the art could readily substitute adaptors providing other restriction sites compatible with cloning sites on a vector of choice. A comparison of the structure of the 5E5 and 3H4 CAR constructs reveals the flexible nature of the organization in terms of the relative positioning of variable regions. The VH can be N-terminal or C-terminal to the VL. Moreover, any linker or linkers known in the art are contemplated. These linkers may vary in length and/or sequence. As noted above, moreover, various signal peptides known in the art may be used in CAR constructs. More generally, any of the above-noted bispecific binding partner forms is contemplated by the disclosure.

The polynucleotide of SEQ ID NO:13, also containing terminal adaptors, is then cloned into a vector, e.g., a lentiviral vectors such as is found in the above-noted ViraSafe™ Lentiviral Expression System (Cell Biolabs, Inc.). The lentiviral clone comprising SEQ ID NO:13 is then transduced into mouse T cells and the CAR-transduced T cells are administered to mice harboring cancers, e.g., solid tumors, such as mouse tumors or human tumor xenografts.

In like manner, it becomes apparent that the compositions and methods of the disclosure are readily adaptable to any animal species with a functioning immune system, including humans, other mammals, and other vertebrates. Moreover, the specific binding of the bivalent binding protein, e.g., CAR, to Tn-O-glycopeptides unique to cancer cells, but not limited to particular types of cancer cells, establishes the versatility of the compositions and methods in treating, preventing, or ameliorating any of a wide variety of cancers. The disclosures herein establish the efficacy and specificity of the Tn-O-glycopeptide binding proteins, such as CARs or BiTEs, both in vitro and in vivo. There can be little doubt that CARs or BiTEs exemplified by the 5E5 and 3H4 CARs will be very useful in cancer therapy particularly in the treatment of cancers with a Cosmc mutation.

In addition, the specific binding of the bivalent binding protein, e.g., an anti-cancer-specific glycopeptide CAR, to the Tn-O-glycopeptide epitope characteristic of a cancer cell indicates that the compositions are useful in diagnosing cancer and in providing prognoses by monitoring cancer progression. Such diagnostic methods would involve administration of bivalent binding proteins that would typically contain a label or an enzymatic component of a labeling system.

LIST OF REFERENCES

1. Moreau, R. J. Dausset, J. Bernard, and J. Moullec. 1957. [Acquired hemolytic anemia with polyagglutinability of erythrocytes by a new factor present in normal blood]. Bull Mem Soc Med Hop Paris 73:569-587.
2. Dausset, J. J. Moullec, and J. Bernard. 1959. Acquired hemolytic anemia with polyagglutinability of red blood cells due to a new factor present in normal human serum (Anti-Tn). Blood 14:1079-1093.
3. Brooks, C. L. A. Schietinger, S. N. Borisova, P. Kufer, M. Okon, T. Hirama, C. R. Mackenzie, L. X. Wang, H. Schreiber, and S. V. Evans. 2010. Antibody recognition of a unique tumor-specific glycopeptide antigen. Proc Natl Acad Sci USA 107:10056-10061.
4. Steentoft, C. K. T. Schjoldager, E. Clo, U. Mandel, S. B. Levery, J. W. Pedersen, K. Jensen, O. Blixt, and H. Clausen. 2010. Characterization of an immunodominant cancer-specific O-glycopeptide epitope in murine podoplanin (OTS8). Glycoconj J 27:571-582.
5. Blixt, 0. E. Clo, A. S. Nudelman, K. K. Sorensen, T. Clausen, H. H. Wandall, P. O. Livingston, H. Clausen, and K. J. Jensen. 2010. A high-throughput O-glycopeptide discovery platform for seromic profiling. J Proteome Res 9:5250-5261.
6. Monach, P. A. S. C. Meredith, C. T. Siegel, and H. Schreiber. 1995. A unique tumor antigen produced by a single amino acid substitution. Immunity 2:45-59.
7. Liu, R. B. B. Engels, A. Arina, K. Schreiber, E. Hyjek, A. Schietinger, D. C. Binder, E. Butz, T. Krausz, D. A. Rowley, B. Jabri, and H. Schreiber. 2012. Densely Granulated Murine NK Cells Eradicate Large Solid Tumors. Cancer Res 72:1964-1974.
8. Morgan, R. A. J. C. Yang, M. Kitano, M. E. Dudley, C. M. Laurencot, and S. A. Rosenberg. 2010. Case report of a serious adverse event following the administration of T cells transduced with a chimeric antigen receptor recognizing ERBB2. Mol Ther 18:843-851.
9. Parkhurst, M. R. J. C. Yang, R. C. Langan, M. E. Dudley, D. A. Nathan, S. A. Feldman, J. L. Davis, R. A. Morgan, M. J. Merino, R. M. Sherry, M. S. Hughes, U. S. Kammula, G. Q. Phan, R. M. Lim, S. A. Wank, N. P. Restifo, P. F. Robbins, C. M. Laurencot, and S. A. Rosenberg. 2011. T cells targeting carcinoembryonic antigen can mediate regression of metastatic colorectal cancer but induce severe transient colitis. Mol Ther 19:620-626.
10. Fong, Y. 2012. Minutes of the Recombinant DNA Advisory Committee, 6/19/12. In Recombinant DNA Advisory Committee. U. S. DEPARTMENT OF HEALTH AND HUMAN SERVICES, National Institutes of Health, Bethesda, Md. 1-34.
11. Morgan, R. A. N. Chinnasamy, D. Abate-Daga, A. Gros, P. F. Robbins, Z. Zheng, M. E. Dudley, S. A. Feldman, J. C. Yang, R. M. Sherry, G. Q. Phan, M. S. Hughes, U. S. Kammula, A. D. Miller, C. J. Hessman, A. A. Stewart, N. P. Restifo, M. M. Quezado, M. Alimchandani, A. Z. Rosenberg, A. Nath, T. Wang, B. Bielekova, S. C. Wuest, N. Akula, F. J. McMahon, S. Wilde, B. Mosetter, D. J. Schendel, C. M. Laurencot, and S. A. Rosenberg. 2013. Cancer Regression and Neurological Toxicity Following Anti-MAGE-A3 TCR Gene Therapy. J Immunother 36:133-151.

12. Ju, T. V. I. Otto, and R. D. Cummings. 2011. The Tn antigen-structural simplicity and biological complexity. Angew Chem Int Ed Engl 50:1770-1791.
13. Springer, G. F. 1984. T and Tn, general carcinoma autoantigens. Science 224:1198-1206.
14. Springer, G. F. and H. Tegtmeyer. 1981. Origin of anti-Thomsen-Friedenreich (T) and Tn agglutinins in man and in White Leghorn chicks. Br J Haematol 47:453-460.
15. Spiotto, M. T. P. Yu, D. A. Rowley, M. I. Nishimura, S. C. Meredith, T. F. Gajewski, Y. X. Fu, and H. Schreiber. 2002. Increasing tumor antigen expression overcomes "ignorance" to solid tumors via crosspresentation by bone marrow-derived stromal cells. Immunity 17:737-747.
16. Schietinger, A. M. Philip, B. A. Yoshida, P. Azadi, H. Liu, S. C. Meredith, and H. Schreiber. 2006. A mutant chaperone converts a wild-type protein into a tumor-specific antigen. Science 314:304-308.
17. Ju, T. G. S. Lanneau, T. Gautam, Y. Wang, B. Xia, S. R. Stowell, M. T. Willard, W. Wang, J. Y. Xia, R. E. Zuna, Z. Laszik, D. M. Benbrook, M. H. Hanigan, and R. D. Cummings. 2008. Human tumor antigens Tn and sialyl Tn arise from mutations in Cosmc. Cancer Res 68:1636-1646.
18. Prokop, O. and G. Uhlenbruck. 1969. [N-acetyl-D-galactosamine in tumor cell membranes: demonstration by means of Helix agglutinins]. Med Welt 46:2515-2519.
19. Springer, G. F. P. R. Desai, and I. Banatwala. 1974. Blood group MN specific substances and precursors in normal and malignant human breast tissues. Naturwissenschaften 61:457-458.
20. Springer, G. F. P. R. Desai, and I. Banatwala. 1975. Blood group MN antigens and precursors in normal and malignant human breast glandular tissue. J Natl Cancer Inst 54:335-339.
21. Hirohashi, S. H. Clausen, T. Yamada, Y. Shimosato, and S. Hakomori. 1985. Blood group A cross-reacting epitope defined by monoclonal antibodies NCC-LU-35 and -81 expressed in cancer of blood group 0 or B individuals: its identification as Tn antigen. Proc Natl Acad Sci USA 82:7039-7043.
22. Wen, F. T. R. A. Thisted, D. A. Rowley, and H. Schreiber. 2012. A systematic analysis of experimental immunotherapies on tumors differing in size and duration of growth. Oncoimmunology 1:172-178.
23. Coulie, P. G. F. Lehmann, B. Lethe, J. Herman, C. Lurquin, M. Andrawiss, and T. Boon. 1995. A mutated intron sequence codes for an antigenic peptide recognized by cytolytic T lymphocytes on a human melanoma. Proc. Natl. Acad. Sci. U.S.A 92:7976-7980.
24. Wölfel, T. M. Hauer, J. Schneider, M. Serrano, C. Wolfel, E. Klehmann-Hieb, E. De Plaen, T. Hankeln, K. H. Meyer zum Buschenfelde, and D. Beach. 1995. A p16INK4a-insensitive CDK4 mutant targeted by cytolytic T lymphocytes in a human melanoma. Science 269:1281-1284.
25. Dubey, P. R. C. Hendrickson, S. C. Meredith, C. T. Siegel, J. Shabanowitz, J. C. Skipper, V. H. Engelhard, D. F. Hunt, and H. Schreiber. 1997. The immunodominant antigen of an ultraviolet-induced regressor tumor is generated by a somatic point mutation in the DEAD box helicase p68. J. Exp. Med. 185:695-705.
26. Yang, L. C. Lin, and Z. R. Liu. 2005. Phosphorylations of DEAD box p68 RNA helicase are associated with cancer development and cell proliferation. Mol Cancer Res 3:355-363.
27. Suzuki, H. I. K. Yamagata, K. Sugimoto, T. Iwamoto, S. Kato, and K. Miyazono. 2009. Modulation of microRNA processing by p53. Nature 460:529-533.
28. Fuller-Pace, F. V. 2006. DExD/H box RNA helicases: multifunctional proteins with important roles in transcriptional regulation. Nucleic Acids Res 34:4206-4215.
29. Schreiber, K. A. Arina, B. Engels, M. T. Spiotto, J. Sidney, A. Sette, T. Karrison, R. R. Weichselbaum, D. A. Rowley, and H. Schreiber. 2012. Spleen cells from young but not old immunized mice eradicate large established cancers. Clin Cancer Res 18:2526-2533.
30. Apostolopoulos, V. E. Yuriev, P. A. Ramsland, J. Halton, C. Osinski, W. Li, M. Plebanski, H. Paulsen, and I. F. McKenzie. 2003. A glycopeptide in complex with MHC class I uses the GalNAc residue as an anchor. Proc Natl Acad Sci USA 100:15029-15034.
31. Napoletano, C. A. Rughetti, M. P. Agervig Tarp, J. Coleman, E. P. Bennett, G. Picco, P. Sale, K. Denda-Nagai, T. Irimura, U. Mandel, H. Clausen, L. Frati, J. Taylor-Papadimitriou, J. Burchell, and M. Nuti. 2007. Tumor-associated Tn-MUC1 glycoform is internalized through the macrophage galactose-type C-type lectin and delivered to the HLA class I and II compartments in dendritic cells. Cancer Res 67:8358-8367.
32. Ju, T. and R. D. Cummings. 2002. A unique molecular chaperone Cosmc required for activity of the mammalian core 1 beta 3-galactosyltransferase. Proc Natl Acad Sci USA 99:16613-16618.
33. Fu, J. B. Wei, T. Wen, M. E. Johansson, X. Liu, E. Bradford, K. A. Thomsson, S. McGee, L. Mansour, M. Tong, J. M. McDaniel, T. J. Sferra, J. R. Turner, H. Chen, G. C. Hansson, J. Braun, and L. Xia. 2011. Loss of intestinal core 1-derived O-glycans causes spontaneous colitis in mice. J Clin Invest 121:1657-1666.
34. Blixt, O. O. I. Lavrova, D. V. Mazurov, E. Clo, S. K. Kracun, N. V. Bovin, and A. V. Filatov. 2012. Analysis of Tn antigenicity with a panel of new IgM and IgG1 monoclonal antibodies raised against leukemic cells. Glycobiology 22:529-542.
35. Sorensen, A. L. C. A. Reis, M. A. Tarp, U. Mandel, K. Ramachandran, V. Sankaranarayanan, T. Schwientek, R. Graham, J. Taylor-Papadimitriou, M. A. Hollingsworth, J. Burchell, and H. Clausen. 2006. Chemoenzymatically synthesized multimeric Tn/STn MUC1 glycopeptides elicit cancer-specific anti-MUC1 antibody responses and override tolerance. Glycobiology 16:96-107.
36. Tarp, M. A. A. L. Sorensen, U. Mandel, H. Paulsen, J. Burchell, J. Taylor-Papadimitriou, and H. Clausen. 2007. Identification of a novel cancer-specific immunodominant glycopeptide epitope in the MUC1 tandem repeat. Glycobiology 17:197-209.
37. Van Elssen, C. H. P. W. Frings, F. J. Bot, K. K. Van de Vijver, M. B. Huls, B. Meek, P. Hupperets, W. T. Germeraad, and G. M. Bos. 2010. Expression of aberrantly glycosylated Mucin-1 in ovarian cancer. Histopathology 57:597-606.
38. Blixt, O. D. Bueti, B. Burford, D. Allen, S. Julien, M. Hollingsworth, A. Gammerman, I. Fentiman, J. Taylor-Papadimitriou, and J. M. Burchell. 2011. Autoantibodies to aberrantly glycosylated MUC1 in early stage breast cancer are associated with a better prognosis. Breast Cancer Res 13:R25.
39. Wang, Y. T. Ju, X. Ding, B. Xia, W. Wang, L. Xia, M. He, and R. D. Cummings. 2010. Cosmc is an essential chaperone for correct protein O-glycosylation. Proc Natl Acad Sci USA 107:9228-9233.
40. Xia, L. T. Ju, A. Westmuckett, G. An, L. Ivanciu, J. M. McDaniel, F. Lupu, R. D. Cummings, and R. P. McEver.

2004. Defective angiogenesis and fatal embryonic hemorrhage in mice lacking core 1-derived O-glycans. J Cell Biol 164:451-459.
41. Cloosen, S. J. Arnold, M. Thio, G. M. Bos, B. Kyewski, and W. T. Germeraad. 2007. Expression of tumor-associated differentiation antigens, MUC1 glycoforms and CEA, in human thymic epithelial cells: implications for self-tolerance and tumor therapy. Cancer Res 67:3919-3926.
42. Ju, T. and R. D. Cummings. 2005. Protein glycosylation: chaperone mutation in Tn syndrome. Nature 437:1252.
43. Schreiber, H. and D. A. Rowley. 1999. Inflammation and Cancer. In Inflammation: Basic Principles and Clinical Correlates. J. I. Gallin, and R. Snyderman, editors. Lippincott Williams & Wilkins, Philadelphia. 1117-1129.
44. Philip, M. D. A. Rowley, and H. Schreiber. 2004. Inflammation as a tumor promoter in cancer induction. Semin Cancer Biol 14:433-439.
45. Kudo, T. T. Iwai, T. Kubota, H. Iwasaki, Y. Takayma, T. Hiruma, N. Inaba, Y. Zhang, M. Gotoh, A. Togayachi, and H. Narimatsu. 2002. Molecular cloning and characterization of a novel UDP-Gal:GalNAc(alpha) peptide beta 1,3-galactosyltransferase (C1Gal-T2), an enzyme synthesizing a core 1 structure of O-glycan. J Biol Chem 277:47724-47731.
46. Vlad, A. M. S. Muller, M. Cudic, H. Paulsen, L. Otvos, Jr. F. G. Hanisch, and O. J. Finn. 2002. Complex carbohydrates are not removed during processing of glycoproteins by dendritic cells: processing of tumor antigen MUC1 glycopeptides for presentation to major histocompatibility complex class II-restricted T cells. J Exp Med 196:1435-1446.
47. Ninkovic, T. L. Kinarsky, K. Engelmann, V. Pisarev, S. Sherman, O. J. Finn, and F. G. Hanisch. 2009. Identification of O-glycosylated decapeptides within the MUC1 repeat domain as potential MHC class I (A2) binding epitopes. Mol Immunol 47:131-140.
48. Wandall, H. H. O. Blixt, M. A. Tarp, J. W. Pedersen, E. P. Bennett, U. Mandel, G. Ragupathi, P. O. Livingston, M. A. Hollingsworth, J. Taylor-Papadimitriou, J. Burchell, and H. Clausen. 2010. Cancer biomarkers defined by autoantibody signatures to aberrant 0-glycopeptide epitopes. Cancer Res 70:1306-1313.
49. Kalos, M. B. L. Levine, D. L. Porter, S. Katz, S. A. Grupp, A. Bagg, and C. H. June. 2011. T cells with chimeric antigen receptors have potent antitumor effects and can establish memory in patients with advanced leukemia. Sci Transl Med 3:95ra73.
50. Porter, D. L. B. L. Levine, M. Kalos, A. Bagg, and C. H. June. 2011. Chimeric antigen receptor-modified T cells in chronic lymphoid leukemia. N Engl J Med 365:725-733.
51. Carpenito, C. M. C. Milone, R. Hassan, J. C. Simonet, M. Lakhal, M. M. Suhoski, A. Varela-Rohena, K. M. Haines, D. F. Heitjan, S. M. Albelda, R. G. Carroll, J. L. Riley, I. Pastan, and C. H. June. 2009. Control of large, established tumor xenografts with genetically retargeted human T cells containing CD28 and CD137 domains. Proc Natl Acad Sci USA 106:3360-3365.
52. Lanitis, E. M. Poussin, I. S. Hagemann, G. Coukos, R. Sandaltzopoulos, N. Scholler, and D. J. Powell, Jr. 2012. Redirected antitumor activity of primary human lymphocytes transduced with a fully human anti-mesothelin chimeric receptor. Mol Ther 20:633-643.
53. Zhao, Y. Q. J. Wang, S. Yang, J. N. Kochenderfer, Z. Zheng, X. Zhong, M. Sadelain, Z. Eshhar, S. A. Rosenberg, and R. A. Morgan. 2009. A herceptin-based chimeric antigen receptor with modified signaling domains leads to enhanced survival of transduced T lymphocytes and anti-tumor activity. J Immunol 183:5563-5574.
54. Ando, H. T. Matsushita, M. Wakitani, T. Sato, S. Kodama-Nishida, K. Shibata, K. Shitara, and S. Ohta. 2008. Mouse-human chimeric anti-Tn IgG1 induced antitumor activity against Jurkat cells in vitro and in vivo. Biol Pharm Bull 31:1739-1744.
55. Welinder, C. B. Baldetorp, C. Borrebaeck, B. M. Fredlund, and B. Jansson. 2011. A new murine IgG1 anti-Tn monoclonal antibody with in vivo anti-tumor activity. Glycobiology 21:1097-1107.
56. Li, Q. M. R. Anver, D. O. Butcher, and J. C. Gildersleeve. 2009. Resolving conflicting data on expression of the Tn antigen and implications for clinical trials with cancer vaccines. Mol Cancer Ther 8:971-979.
57. Yu, L. G. 2007. The oncofetal Thomsen-Friedenreich carbohydrate antigen in cancer progression. Glycoconj J 24:411-420.
58. Akita, K. S. Fushiki, T. Fujimoto, M. Inoue, K. Oguri, M. Okayama, I. Yamashina, and H. Nakada. 2001. Developmental expression of a unique carbohydrate antigen, Tn antigen, in mouse central nervous tissues. J Neurosci Res 65:595-603.
59. Stone, J. D. D. H. Aggen, A. Schietinger, H. Schreiber, and D. M. Kranz. 2012. A sensitivity scale for targeting T cells with chimeric antigen receptors (CARs) and bispecific T-cell Engagers (BiTEs). Oncoimmunology 1:863-873.
60. Ward, P. L. H. Koeppen, T. Hurteau, and H. Schreiber. 1989. Tumor antigens defined by cloned immunological probes are highly polymorphic and are not detected on autologous normal cells. J. Exp. Med. 170:217-232.
61. Milone, M. C. J. D. Fish, C. Carpenito, R. G. Carroll, G. K. Binder, D. Teachey, M. Samanta, M. Lakhal, B. Gloss, G. Danet-Desnoyers, D. Campana, J. L. Riley, S. A. Grupp, and C. H. June. 2009. Chimeric receptors containing CD137 signal transduction domains mediate enhanced survival of T cells and increased antileukemic efficacy in vivo. Mol Ther 17:1453-1464.
62. Sadelain, M. R. Brentjens, and I. Riviere. 2009. The promise and potential pitfalls of chimeric antigen receptors. Curr Opin Immunol 21:215-223.
63. Schreiber, H. 2013. Cancer Immunology. In Fundamental Immunology. W. E. Paul, editor Lippincott-Williams & Wilkins, Philadelphia, Pa. 1200-1234.
64. Schietinger, A. M. Philip, R. B. Liu, K. Schreiber, and H. Schreiber. 2010. Bystander killing of cancer requires the cooperation of CD4(+) and CD8(+) T cells during the effector phase. J Exp Med 207:2469-2477.
65. Bos, R. and L. A. Sherman. 2010. CD4+ T-cell help in the tumor milieu is required for recruitment and cytolytic function of CD8+ T lymphocytes. Cancer Res 70:8368-8377.
66. Zhang, B. T. Karrison, D. A. Rowley, and H. Schreiber. 2008. IFN-gamma- and TNF-dependent bystander eradication of antigen-loss variants in established mouse cancers. J Clin Invest 118:1398-1404.
67. Neeson, P. A. Shin, K. M. Tainton, P. Guru, H. M. Prince, S. J. Harrison, S. Peinert, M. J. Smyth, J. A. Trapani, M. H. Kershaw, P. K. Darcy, and D. S. Ritchie. 2010. Ex vivo culture of chimeric antigen receptor T cells generates functional CD8+ T cells with effector and central memory-like phenotype. Gene Ther 17:1105-1116.
68. Steentoft, C. S. Y. Vakhrushev, M. B. Vester-Christensen, K. T. Schjoldager, Y. Kong, E. P. Bennett, U. Mandel, H. Wandall, S. B. Levery, and H. Clausen. 2011. Mining the O-glycoproteome using zinc-finger nuclease-glycoengineered SimpleCell lines. Nat Methods 8:977-982.
69. Taupier, M. A. J. F. Kearney, P. J. Leibson, M. R. Loken, and H. Schreiber. 1983. Nonrandom escape of tumor cells from immune lysis due to intraclonal fluctuations in antigen expression. Cancer Res 43:4050-4056.
70. Gupta, P. B. C. M. Fillmore, G. Jiang, S. D. Shapira, K. Tao, C. Kuperwasser, and E. S. Lander. 2011. Stochastic state transitions give rise to phenotypic equilibrium in populations of cancer cells. Cell 146:633-644.
71. Guba, M. G. Cernaianu, G. Koehl, E. K. Geissler, K. W. Jauch, M. Anthuber, W. Falk, and M. Steinbauer. 2001. A primary tumor promotes dormancy of solitary tumor cells before inhibiting angiogenesis. Cancer Res 61:5575-5579.
72. Louis, C. U. B. Savoldo, G. Dotti, M. Pule, E. Yvon, G. D. Myers, C. Rossig, H. V. Russell, O. Diouf, E. Liu, H. Liu, M. F. Wu, A. P. Gee, Z. Mei, C. M. Rooney, H. E. Heslop, and M. K. Brenner. 2011. Antitumor activity and long-term fate of chimeric antigen receptor-positive T cells in patients with neuroblastoma. Blood 118:6050-6056.
73. Baeuerle, P. A. P. Kufer, and R. Bargou. 2009. BiTE: Teaching antibodies to engage T-cells for cancer therapy. Curr Opin Mol Ther 11:22-30.
74. Liddy, N. G. Bossi, K. J. Adams, A. Lissina, T. M. Mahon, N. J. Hassan, J. Gavarret, F. C. Bianchi, N. J. Pumphrey, K. Ladell, E. Gostick, A. K. Sewell, N. M. Lissin, N. E. Harwood, P. E. Molloy, Y. Li, B. J. Cameron, M. Sami, E. E. Baston, P. T. Todorov, S. J. Paston, R. E. Dennis, J. V. Harper, S. M. Dunn, R. Ashfield, A. Johnson, Y. McGrath, G. Plesa, C. H. June, M. Kalos, D. A. Price, A. Vuidepot, D. D. Williams, D. H. Sutton, and B. K. Jakobsen. 2012. Monoclonal TCR-redirected tumor cell killing. Nat Med
75. Narni-Mancinelli, E. J. Chaix, A. Fenis, Y. M. Kerdiles, N. Yessaad, A. Reynders, C. Gregoire, H. Luche, S. Ugolini, E. Tomasello, T. Walzer, and E. Vivier. 2011. Fate mapping analysis of lymphoid cells expressing the NKp46 cell surface receptor. Proc Natl Acad Sci USA 108:18324-18329.
76. Brentjens, R. J. J. B. Latouche, E. Santos, F. Marti, M. C. Gong, C. Lyddane, P. D. King, S. Larson, M. Weiss, I. Riviere, and M. Sadelain. 2003. Eradication of systemic B-cell tumors by genetically targeted human T lymphocytes co-stimulated by CD80 and interleukin-15. Nat Med 9:279-286.
77. Davila, M. L. R. Brentjens, X. Wang, I. Riviere, and M. Sadelain. 2012. How do CARs work?: Early insights from recent clinical studies targeting CD19. Oncoimmunology 1:1577-1583.
78. Mukherjee, P. L. B. Pathangey, J. B. Bradley, T. L. Tinder, G. D. Basu, E. T. Akporiaye, and S. J. Gendler. 2007. MUC1-specific immune therapy generates a strong anti-tumor response in a MUC1-tolerant colon cancer model. Vaccine 25:1607-1618.
79. Liu, Q. P. G. Sulzenbacher, H. Yuan, E. P. Bennett, G. Pietz, K. Saunders, J. Spence, E. Nudelman, S. B. Levery, T. White, J. M. Neveu, W. S. Lane, Y. Bourne, M. L. Olsson, B. Henrissat, and H. Clausen. 2007. Bacterial glycosidases for the production of universal red blood cells. Nat Biotechnol 25:454-464.
80. Pedersen, J. W. O. Blixt, E. P. Bennett, M. A. Tarp, I. Dar, U. Mandel, S. S. Poulsen, A. E. Pedersen, S. Rasmussen, P. Jess, H. Clausen, and H. H. Wandall. 2011. Seromic profiling of colorectal cancer patients with novel glycopeptide microarray. Int J Cancer 128:1860-1871.

Each of the references cited herein is incorporated by reference in its entirety or in relevant part as would be apparent from the context of its usage.

From the disclosure herein it will be appreciated that, although specific embodiments of the disclosure have been described herein for purposes of illustration, various modifications may be made without deviating from the spirit and scope of the disclosure.

What is claimed is:

1. A cancer-specific Tn glycopeptide binding partner that binds a cancer-specific Tn glycopeptide, wherein the binding partner comprises the antibody heavy chain variable fragment (VH) of SEQ ID NO:19 or a humanized derivative thereof, and the antibody light chain variable fragment (VL) of SEQ ID NO:20 or a humanized derivative thereof.

2. The cancer-specific Tn glycopeptide binding partner of claim 1 wherein the binding partner comprises the antibody heavy chain variable fragment (VH) of SEQ ID NO:19 and the antibody light chain variable fragment (VL) of SEQ ID NO:20.

3. The cancer-specific Tn glycopeptide binding partner of claim 1 wherein the binding partner is a single-chain variable fragment (scFv).

4. The cancer-specific Tn glycopeptide binding partner of claim 3 wherein the scFv comprises the heavy chain variable fragment N-terminal to the light chain variable fragment.

5. The cancer-specific Tn glycopeptide binding partner of claim 3 wherein the scFv heavy chain variable fragment and light chain variable fragment are covalently bound to a linker sequence of 4-15 amino acids.

6. The cancer-specific Tn glycopeptide binding partner of claim 3 wherein the single-chain variable fragment is contained within a bi-specific T-cell engager.

7. The cancer-specific Tn glycopeptide binding partner of claim 3 wherein the single-chain variable fragment is contained within a chimeric antigen receptor.

8. A polynucleotide comprising a coding region for a cancer-specific Tn glycopeptide binding partner heavy chain variable region and light chain variable region according to claim 1.

9. The polynucleotide according to claim 8, wherein the coding region is codon-optimized for expression in a human cell.

10. The polynucleotide according to claim 9 wherein the coding region for the heavy chain variable fragment is set forth in SEQ ID NO:9 and the coding region for the light chain variable fragment is set forth in SEQ ID NO:11.

11. The polynucleotide according to claim 8 wherein the polynucleotide encodes a cancer-specific Tn glycopeptide binding partner selected from the group consisting of a single-chain variable fragment, a multimer of a single-chain variable fragment, a bi-specific single-chain variable fragment and a multimer of a bi-specific single-chain variable fragment.

12. The polynucleotide according to claim 11 wherein the multimer of a single-chain variable fragment is selected from the group consisting of a divalent single-chain variable fragment, a tribody and a tetrabody.

13. The polynucleotide according to claim 11 wherein the multimer of a bi-specific single-chain variable fragment is a bi-specific T-cell engager.

14. The polynucleotide according to claim 8 further comprising a coding region for a peptide selected from the group consisting of a peptide signaling domain of a T cell signaling protein, a peptide modulator of T cell activation, and an enzymatic component of a labeling system.

15. The polynucleotide according to claim 14 wherein the peptide signaling domain of a T cell signaling protein is selected from the group consisting of a 4-1 BB cytosolic signaling domain, a CD3 cytosolic signaling domain, a cytosolic domain of CD28-CD3 fusion and a cytosolic domain of a 4-1 BB-CD3ζ fusion.

16. The polynucleotide according to claim 8 further comprising a peptide modulator of T cell activation selected from the group consisting of IL15, IL15Rα and an IL15/IL15Rα fusion peptide.

17. The polynucleotide according to claim 8 further comprising a coding region for a linker peptide comprising the sequence of SEQ ID NO:14.

18. The polynucleotide according to claim 8 further comprising a coding region for a signal peptide comprising the sequence of SEQ ID NO:8.

* * * * *

UNITED STATES PATENT AND TRADEMARK OFFICE
CERTIFICATE OF CORRECTION

PATENT NO. : 10,189,908 B2
APPLICATION NO. : 15/115536
DATED : January 29, 2019
INVENTOR(S) : Hans Schreiber et al.

Page 1 of 1

It is certified that error appears in the above-identified patent and that said Letters Patent is hereby corrected as shown below:

In the Claims

At Column 70, Line 24, "CD3 cytosolic" should be -- CD3ζ cytosolic --.

At Column 70, Line 25, "CD28-CD3 fusion" should be -- CD28-CD3ζ fusion --.

Signed and Sealed this
Twenty-eighth Day of May, 2019

Andrei Iancu
*Director of the United States Patent and Trademark Office*